(12) United States Patent
Sharma et al.

(10) Patent No.: US 10,842,548 B2
(45) Date of Patent: *Nov. 24, 2020

(54) VAPOR ABLATION SYSTEM WITH A CATHETER HAVING MORE THAN ONE POSITIONING ELEMENT

(71) Applicant: Santa Anna Tech LLC, Santa Ana, CA (US)

(72) Inventors: Virender K. Sharma, Paradise Valley, AZ (US); William Parks, Lawrenceville, GA (US)

(73) Assignee: Santa Anna Tech LLC, Santa Ana, CA (US)

( * ) Notice: Subject to any disclaimer, the term of this patent is extended or adjusted under 35 U.S.C. 154(b) by 953 days.

This patent is subject to a terminal disclaimer.

(21) Appl. No.: 15/386,229

(22) Filed: Dec. 21, 2016

(65) Prior Publication Data
US 2017/0231676 A1    Aug. 17, 2017

Related U.S. Application Data

(63) Continuation of application No. 13/486,980, filed on Jun. 1, 2012, now Pat. No. 9,561,066, and a
(Continued)

(51) Int. Cl.
*A61B 18/04*    (2006.01)
*A61B 5/107*    (2006.01)
(Continued)

(52) U.S. Cl.
CPC .......... *A61B 18/04* (2013.01); *A61B 5/1076* (2013.01); *A61B 5/6853* (2013.01); *A61B 17/24* (2013.01);
(Continued)

(58) Field of Classification Search
CPC .......... A61B 2018/00005; A61B 2018/00011; A61B 2018/00029; A61B 2018/044;
(Continued)

(56) References Cited

U.S. PATENT DOCUMENTS

| 408,899 A | 8/1889 | Small |
|---|---|---|
| 697,181 A | 4/1902 | Smith |

(Continued)

FOREIGN PATENT DOCUMENTS

| CN | 2757751 Y | 2/2006 |
|---|---|---|
| CN | 1803113 A | 7/2006 |

(Continued)

OTHER PUBLICATIONS

Office Action for CN2015100881831, dated Apr. 6, 2017.
(Continued)

*Primary Examiner* — Jaymi E Della
(74) *Attorney, Agent, or Firm* — Novel IP

(57) ABSTRACT

The present application discloses devices that ablate human tissue. The device comprises a catheter with a shaft through which an ablative agent can travel, a liquid reservoir and a heating component, which may comprise a length of coiled tubing contained within a heating element, wherein activation of said heating element causes said coiled tubing to increase from a first temperature to a second temperature and wherein the increase causes a conversion of liquid within the coiled tubing to vapor, a reusable cord connecting the outlet of the reservoir to the inlet of the heating component, and a single use cord connecting a pressure-resistant inlet port of a vapor based ablation device to the outlet of the heating component.

24 Claims, 35 Drawing Sheets

Related U.S. Application Data continuation-in-part of application No. 12/573,939, filed on Oct. 6, 2009, now abandoned.

(60) Provisional application No. 61/493,344, filed on Jun. 3, 2011, provisional application No. 61/102,885, filed on Oct. 6, 2008.

(51) Int. Cl.
| | | |
|---|---|---|
| *A61B 5/00* | (2006.01) | |
| *A61B 17/24* | (2006.01) | |
| *A61B 17/00* | (2006.01) | |
| *A61M 25/10* | (2013.01) | |
| *A61B 18/00* | (2006.01) | |
| *A61B 90/00* | (2016.01) | |
| *A61B 17/42* | (2006.01) | |
| *A61M 25/04* | (2006.01) | |

(52) U.S. Cl.
CPC ........... *A61B 2017/00084* (2013.01); *A61B 2017/00203* (2013.01); *A61B 2017/00809* (2013.01); *A61B 2017/00973* (2013.01); *A61B 2017/4216* (2013.01); *A61B 2018/00327* (2013.01); *A61B 2018/00488* (2013.01); *A61B 2018/00494* (2013.01); *A61B 2018/00541* (2013.01); *A61B 2018/00547* (2013.01); *A61B 2018/00559* (2013.01); *A61B 2018/00577* (2013.01); *A61B 2018/00642* (2013.01); *A61B 2018/00648* (2013.01); *A61B 2018/00714* (2013.01); *A61B 2018/00744* (2013.01); *A61B 2018/00791* (2013.01); *A61B 2018/048* (2013.01); *A61B 2090/064* (2016.02); *A61M 25/04* (2013.01); *A61M 25/1011* (2013.01); *A61M 2205/3368* (2013.01)

(58) Field of Classification Search
CPC ............ A61B 2018/046; A61B 18/04; A61B 2018/00273; A61B 2018/00279; A61B 2018/00285; A61B 5/6839; A61B 5/6882
See application file for complete search history.

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,470,308 A | 11/1995 | Edwards |
| 5,470,309 A | 11/1995 | Edwards |
| 5,484,400 A | 1/1996 | Edwards |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,803 A | 11/1996 | Cooper |
| 5,584,872 A | 12/1996 | LaFontaine |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,681,282 A | 10/1997 | Eggers |
| 5,683,366 A | 11/1997 | Eggers |
| 5,695,507 A | 12/1997 | Auth |

(56) References Cited

U.S. PATENT DOCUMENTS

| | | |
|---|---|---|
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,810,764 A | 9/1998 | Eggers |
| 5,820,580 A | 10/1998 | Edwards |
| 5,824,703 A | 10/1998 | Clark, Jr. |
| 5,827,268 A | 10/1998 | Laufer |
| 5,830,179 A | 11/1998 | Mikus |
| 5,836,906 A | 11/1998 | Edwards |
| 5,843,019 A | 12/1998 | Eggers |
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | McGaffigan |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,897,553 A | 4/1999 | Mulier |
| 5,902,272 A | 5/1999 | Eggers |
| 5,913,856 A | 6/1999 | Chia |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | McGaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwan, Jr. |
| 5,989,445 A | 11/1999 | Wise |
| 5,997,499 A | 12/1999 | Sussman |
| 6,015,406 A | 1/2000 | Goble |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,066,132 A | 5/2000 | Chen |
| 6,066,134 A | 5/2000 | Eggers |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | LaFleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,126,682 A | 10/2000 | Sharkey |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | LaFontaine |
| 6,174,308 B1 | 1/2001 | Goble |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 * | 5/2001 | Swartz ............... A61B 18/1492 606/45 |
| 6,238,389 B1 | 5/2001 | Paddock |
| 6,238,391 B1 | 5/2001 | Olsen |
| 6,241,702 B1 | 6/2001 | Lundquist |
| 6,254,597 B1 | 7/2001 | Rizoiu |
| 6,254,600 B1 | 7/2001 | Willink |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,277,112 B1 | 8/2001 | Underwood |
| 6,277,114 B1 | 8/2001 | Bullivant |
| 6,277,130 B1 | 8/2001 | Shadduck |
| 6,283,961 B1 | 9/2001 | Underwood |
| 6,283,989 B1 | 9/2001 | Laufer |
| 6,287,274 B1 | 9/2001 | Sussman |

(56) References Cited

U.S. PATENT DOCUMENTS

| | | |
|---|---|---|
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,620 B1 | 10/2001 | Shadduck |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,327,505 B1 | 12/2001 | Medhkour |
| 6,331,171 B1 | 12/2001 | Cohen |
| 6,355,032 B1 | 3/2002 | Hovda |
| 6,358,248 B1 | 3/2002 | Mulier |
| 6,363,937 B1 | 4/2002 | Hovda |
| 6,364,877 B1 | 4/2002 | Goble |
| 6,375,635 B1 | 4/2002 | Moutafis |
| 6,379,350 B1 | 4/2002 | Sharkey |
| 6,379,351 B1 | 4/2002 | Thapliyal |
| 6,391,025 B1 | 5/2002 | Weinstein |
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,507 B1 | 7/2002 | Eggers |
| 6,416,508 B1 | 7/2002 | Eggers |
| 6,416,509 B1 | 7/2002 | Goble |
| 6,419,673 B1 | 7/2002 | Edwards |
| 6,423,027 B1 | 7/2002 | Gonon |
| 6,432,103 B1 | 8/2002 | Ellsberry |
| 6,440,127 B2 | 8/2002 | McGovern |
| 6,458,231 B1 | 10/2002 | Wapner |
| 6,461,296 B1 | 10/2002 | Desai |
| 6,461,350 B1 | 10/2002 | Underwood |
| 6,461,354 B1 | 10/2002 | Olsen |
| 6,464,694 B1 | 10/2002 | Massengill |
| 6,464,695 B2 | 10/2002 | Hovda |
| 6,468,270 B1 | 10/2002 | Hovda |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,488,680 B1 | 12/2002 | Francischelli |
| 6,491,710 B2 | 12/2002 | Satake |
| 6,493,589 B1 | 12/2002 | Medhkour |
| 6,500,173 B2 | 12/2002 | Underwood |
| 6,508,816 B2 | 1/2003 | Shadduck |
| 6,510,854 B2 | 1/2003 | Goble |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | McGaffigan |
| 6,557,559 B1 | 5/2003 | Eggers |
| 6,558,314 B1 | 5/2003 | Adelman |
| 6,558,379 B1 | 5/2003 | Batchelor |
| 6,566,636 B1 | 5/2003 | Bentley |
| 6,569,146 B1 | 5/2003 | Werner |
| 6,575,929 B2 | 6/2003 | Sussman |
| 6,575,932 B1 | 6/2003 | OBrien |
| 6,575,968 B1 | 6/2003 | Eggers |
| 6,579,270 B2 | 6/2003 | Sussman |
| 6,582,423 B1 | 6/2003 | Thapliyal |
| 6,585,639 B1 | 7/2003 | Kotmel |
| 6,585,732 B2 | 7/2003 | Mulier |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,087 B2 | 8/2003 | Swartz |
| 6,607,529 B1 | 8/2003 | Jones |
| 6,610,043 B1 | 8/2003 | Ingenito |
| 6,620,130 B1 | 9/2003 | Ginsburg |
| 6,620,155 B2 | 9/2003 | Underwood |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,647,300 B1 | 11/2003 | Balasubramanian |
| 6,648,847 B2 | 11/2003 | Sussman |
| 6,652,594 B2 | 11/2003 | Francis |
| 6,653,525 B2 | 11/2003 | Ingenito |
| 6,659,106 B1 | 12/2003 | Hovda |
| 6,669,685 B1 | 12/2003 | Rizoiu |
| 6,669,694 B2 | 12/2003 | Shadduck |
| 6,673,071 B2 | 1/2004 | VanDusseldorp |
| 6,676,628 B2 | 1/2004 | Sussman |
| 6,676,629 B2 | 1/2004 | Andrew |
| 6,679,264 B1 | 1/2004 | Deem |
| 6,679,879 B2 | 1/2004 | Shadduck |
| 6,682,520 B2 | 1/2004 | Ingenito |
| 6,692,494 B1 | 2/2004 | Cooper |
| 6,695,839 B2 | 2/2004 | Sharkey |
| 6,699,244 B2 | 3/2004 | Carranza |
| 6,708,056 B2 | 3/2004 | Duchon |
| 6,712,811 B2 | 3/2004 | Underwood |
| 6,712,812 B2 | 3/2004 | Roschak |
| 6,716,252 B2 | 4/2004 | Lazarovitz |
| 6,719,738 B2 | 4/2004 | Mehier |
| 6,719,754 B2 | 4/2004 | Underwood |
| 6,719,755 B2 | 4/2004 | Sliwa, Jr. |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,740,082 B2 | 5/2004 | Shadduck |
| 6,746,447 B2 | 6/2004 | Davison |
| 6,749,604 B1 | 6/2004 | Eggers |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |

(56) References Cited

U.S. PATENT DOCUMENTS

| | | |
|---|---|---|
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,916,318 B2 | 7/2005 | Francischelli |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,949,098 B2 | 9/2005 | Mulier |
| 6,952,615 B2 | 10/2005 | Satake |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| 7,112,198 B2 | 9/2006 | Satake |
| 7,113,838 B2 | 9/2006 | Funk |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,166,105 B2 | 1/2007 | Mulier |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,364,579 B2 | 4/2008 | Mulier |
| 7,410,486 B2 | 8/2008 | Fuimaono |
| 7,419,500 B2 | 9/2008 | Marko |
| 7,422,588 B2 | 9/2008 | Mulier |
| 7,429,262 B2 | 9/2008 | Woloszko |
| 7,435,250 B2 | 10/2008 | Francischelli |
| 7,470,228 B2 | 12/2008 | Connors |
| 7,470,272 B2 | 12/2008 | Mulier |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,727,228 B2 | 6/2010 | Abboud |
| 7,753,871 B2 | 7/2010 | Mehier |
| 7,794,460 B2 | 9/2010 | Mulier |
| 7,831,133 B2 | 11/2010 | Vinegar |
| 7,892,229 B2 | 2/2011 | Shadduck |
| 7,913,698 B2 | 3/2011 | Barry |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,147,532 B2 | 4/2012 | Barry |
| 8,187,269 B2 | 5/2012 | Shadduck |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,251,985 B2 | 8/2012 | Hoey |
| 8,272,383 B2 | 9/2012 | Hoey |
| 8,273,079 B2 | 9/2012 | Hoey |
| 8,313,485 B2 | 11/2012 | Shadduck |
| 8,322,335 B2 | 12/2012 | Barry |
| 8,355,623 B2 | 1/2013 | Vinegar |
| 8,372,065 B2 | 2/2013 | Hoey |
| 8,388,611 B2 | 3/2013 | Shadduck |
| 8,419,723 B2 | 4/2013 | Shadduck |
| 8,437,870 B2 | 5/2013 | Tsai |
| 8,444,636 B2 | 5/2013 | Shadduck |
| 8,512,326 B2 | 8/2013 | Shadduck |
| 8,521,074 B2 | 8/2013 | Murakami |
| 8,574,226 B2 | 11/2013 | Shadduck |
| 8,579,888 B2 | 11/2013 | Hoey |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,632,530 B2 | 1/2014 | Hoey |
| 8,647,339 B2 | 2/2014 | Satake |
| 8,721,632 B2 | 5/2014 | Hoey |
| 8,734,380 B2 | 5/2014 | Barry |
| 8,758,341 B2 | 6/2014 | Shadduck |
| 8,761,626 B2 | 6/2014 | Seo |
| 8,801,702 B2 | 8/2014 | Hoey |
| 8,805,466 B2 | 8/2014 | Salahieh |
| 8,858,549 B2 | 10/2014 | Shadduck |
| 8,900,223 B2 | 12/2014 | Shadduck |
| 8,911,430 B2 | 12/2014 | Hoey |
| 9,113,858 B2 | 8/2015 | Barry |
| 9,113,944 B2 | 8/2015 | Shadduck |
| 9,125,667 B2 | 9/2015 | Stone |
| 9,161,801 B2 | 10/2015 | Hoey |
| 9,179,973 B2 | 11/2015 | Nabutovsky |
| 9,198,708 B2 | 12/2015 | Hoey |
| 9,204,889 B2 | 12/2015 | Shadduck |
| 9,345,507 B2 | 5/2016 | Hoey |
| 9,387,310 B2 | 7/2016 | Satake |

(56) References Cited

U.S. PATENT DOCUMENTS

| | | |
|---|---|---|
| 9,433,457 B2 | 9/2016 | Shadduck |
| 9,468,487 B2 | 10/2016 | Shadduck |
| 9,526,555 B2 | 12/2016 | Hoey |
| 9,615,875 B2 | 4/2017 | Shadduck |
| 9,757,535 B2 | 9/2017 | Rajagopalan |
| 9,844,641 B2 | 12/2017 | Rajagopalan |
| 9,907,599 B2 | 3/2018 | Hoey |
| 9,974,607 B2 | 5/2018 | Stone |
| 10,299,857 B2 | 5/2019 | Rajagopalan |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1* | 6/2002 | Shadduck ............... A61B 18/04 607/96 |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0156470 A1 | 10/2002 | Shadduck |
| 2002/0161326 A1 | 10/2002 | Sussman |
| 2002/0177846 A1* | 11/2002 | Mulier .................. A61B 18/04 606/27 |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | McGurk |
| 2006/0036237 A1 | 2/2006 | Davison |
| 2006/0041277 A1* | 2/2006 | Deem .................. A61N 1/0551 607/3 |
| 2006/0047291 A1 | 3/2006 | Barry |
| 2006/0085054 A1 | 4/2006 | Zikorus |
| 2006/0095032 A1* | 5/2006 | Jackson ............... A61B 5/0538 606/41 |
| 2006/0100619 A1 | 5/2006 | McClurken |
| 2006/0130830 A1 | 6/2006 | Barry |
| 2006/0135955 A1* | 6/2006 | Shadduck ............... A61B 18/04 606/27 |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0276871 A1 | 12/2006 | Lamson |
| 2007/0032785 A1 | 2/2007 | Diederich |
| 2007/0036417 A1 | 2/2007 | Argiro |
| 2007/0049920 A1 | 3/2007 | McClurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1* | 9/2007 | Ren ........................ A61F 2/013 606/200 |
| 2007/0239197 A1 | 10/2007 | Dubey |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | Lepivert |
| 2009/0018553 A1 | 1/2009 | McLean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0082837 A1 | 3/2009 | Gellman |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1* | 8/2009 | Hoey .................. A61B 18/082 606/27 |
| 2009/0221998 A1 | 9/2009 | Epstein |
| 2009/0227998 A1 | 9/2009 | Aljuri |
| 2009/0277457 A1 | 11/2009 | Hoey |

(56) References Cited

U.S. PATENT DOCUMENTS

| | | |
|---|---|---|
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1* | 3/2010 | Hoey ............... A61B 18/18 606/2 |
| 2010/0094270 A1 | 4/2010 | Sharma |
| 2010/0114082 A1 | 5/2010 | Sharma |
| 2010/0114083 A1 | 5/2010 | Sharma |
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0179416 A1 | 7/2010 | Hoey |
| 2010/0179528 A1 | 7/2010 | Shadduck |
| 2010/0204688 A1 | 8/2010 | Hoey |
| 2010/0262133 A1 | 10/2010 | Hoey |
| 2010/0274260 A1 | 10/2010 | DArpiany |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0172654 A1 | 7/2011 | Barry |
| 2011/0238144 A1 | 9/2011 | Hoey |
| 2011/0264090 A1 | 10/2011 | Shadduck |
| 2011/0276046 A1* | 11/2011 | Heimbecher ...... A61B 18/1492 606/35 |
| 2012/0065632 A1 | 3/2012 | Shadduck |
| 2012/0078078 A1 | 3/2012 | MacAdam |
| 2012/0101413 A1 | 4/2012 | Beetel |
| 2012/0116376 A1 | 5/2012 | Hoey |
| 2012/0232409 A1 | 9/2012 | Stahmann |
| 2012/0259271 A1 | 10/2012 | Shadduck |
| 2012/0323167 A1 | 12/2012 | Hoey |
| 2013/0006231 A1 | 1/2013 | Sharma |
| 2013/0074847 A1 | 3/2013 | Hoey |
| 2013/0079772 A1 | 3/2013 | Shadduck |
| 2013/0116683 A1 | 5/2013 | Shadduck |
| 2013/0172867 A1 | 7/2013 | Shadduck |
| 2013/0237978 A1 | 9/2013 | Shadduck |
| 2013/0267939 A1 | 10/2013 | Barry |
| 2013/0296837 A1 | 11/2013 | Burnett |
| 2013/0345670 A1 | 12/2013 | Rajagopalan |
| 2014/0025057 A1 | 1/2014 | Hoey |
| 2014/0031805 A1 | 1/2014 | Shadduck |
| 2014/0107637 A1 | 4/2014 | Hoey |
| 2014/0114306 A1 | 4/2014 | Harada |
| 2014/0200569 A1 | 7/2014 | Shadduck |
| 2014/0200570 A1 | 7/2014 | Hoey |
| 2014/0276713 A1 | 9/2014 | Hoey |
| 2014/0288543 A1 | 9/2014 | Hoey |
| 2014/0324037 A1 | 10/2014 | Hoey |
| 2014/0357956 A1 | 12/2014 | Salahieh |
| 2014/0371736 A1 | 12/2014 | Levin |
| 2015/0025515 A1 | 1/2015 | Hoey |
| 2015/0025516 A1 | 1/2015 | Hoey |
| 2015/0080883 A1 | 3/2015 | Haverkost |
| 2015/0126990 A1 | 5/2015 | Sharma |
| 2015/0265329 A1 | 9/2015 | Lalonde |

FOREIGN PATENT DOCUMENTS

| | | |
|---|---|---|
| CN | 102238920 | 9/2011 |
| EP | 1602338 B1 | 12/2005 |
| EP | 2341859 | 7/2011 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 | 4/2010 |
| WO | 2010042461 A1 | 4/2010 |
| WO | 2012167213 | 12/2012 |
| WO | 2012167213 A2 | 12/2012 |
| WO | 2013086461 A1 | 6/2013 |
| WO | 2013152119 A1 | 10/2013 |
| WO | 2014113724 | 7/2014 |
| WO | 2014113724 A2 | 7/2014 |
| WO | 2017201504 A1 | 11/2017 |

OTHER PUBLICATIONS

First Office Action for EP09819726.2, dated Oct. 28, 2015.
European Search Report for EP16205336, dated Feb. 10, 2017.
"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.
International Search Report for PCT/US2009/059609, dated Mar. 5, 2010.
International Search Report for PCT/US2012/040639, dated Dec. 18, 2012.
Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.
Van De Velde; Vapo-cauterization of the uterus; Amer. J. Med. Sci.; vol. CXVII; 1899.
Blacker; Vaporization of the uterus; J. Obstet. & Gyn.; pp. 488-511; 1901.
Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.
Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.
Sharma et al; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.
Sanfilippo et al; Update: Options in Endometrial Ablation; Supplement to OBG Management; Dec. 2009; pp. S1-S24; Dowden Health Media.
United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; her option office cryoablation therapy Resource Guide; 2007; pp. 1-29; American Medical Systems, Inc.. 10700 Bren Road West, Minnetonka, MN 55343 USA.
Boston Scientific; HTA System Endometrial Ablation System; 2006; BVU 1090 Rev. A 10M Sep. 2006-Sep. 2008; Boston Scientific Corporation, One Boston Scientific Place, Natick, MA 01760-1537.
Ethicon Women'S Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.

(56) References Cited

OTHER PUBLICATIONS

Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.
Carter; Endometrial Ablation: More Choices, More Options; The Female Patient; 2005; pp. 35-40; 30(12).
Thibeau; AW-06995-001; Text, Manual, Novasure, V1, EN, US; Aug. 26, 2011; pp. 1-23; Hologic, Inc.
Neuwirth et al.; The endometrial ablator: a new instrument; Obst. & Gyn.; vol. 83; No. 5; part 1; pp. 792-796; 1994.
Prior et al.; Treatment of mennorrhagia by radiofrequency heating; Int. J. Hyperthermia; vol. 7; No. 2; pp. 213-220; 1991.
International Search Report for PCT/US2014/012131, dated Jul. 30, 2014.
Office Action dated Sep. 19, 2016 for U.S. Appl. No. 14/062,054.
Office Action dated Mar. 7, 2017 for U.S. Appl. No. 14/062,054.
Office Action dated Jun. 13, 2016 for U.S. Appl. No. 14/158,687.
First Office Action for Chinese Patent Application No. CN201280027522.X, dated Sep. 2, 2015.
Office Action dated Dec. 26, 2014 for U.S. Appl. No. 12/573,946.
Office Action dated Dec. 3, 2015 for U.S. Appl. No. 12/573,946.
Office Action dated Feb. 20, 2015 for U.S. Appl. No. 13/486,980.
Office Action dated Sep. 10, 2015 for U.S. Appl. No. 13,486,980.
Office Action dated Mar. 4, 2015 for U.S. Appl. No. 14/594,444.
European Search Report, 12793307, Sharma, Virender K., dated Sep. 22, 2014.
Notice of Allowance dated Jan. 7, 2015 for U.S. Appl. No. 12/793,307.
Office Action dated Jul. 20, 2015 for U.S. Appl. No. 14/594,444.
Notice of Allowance dated May 23, 2016 for U.S. Appl. No. 12/573,946.
Office Action dated Sep. 27, 2016 for U.S. Appl. No. 14/158,687.
Notice of Allowance dated Oct. 3, 2016 for U.S. Appl. No. 14/594,444.
Office Action dated Nov. 4, 2016 for U.S. Appl. No. 13/486,980.
Notice of Allowance dated Apr. 5, 2017 for U.S. Appl. No. 12/573,946.
European Search Report for EP12793307, dated Apr. 10, 2017.
International Search Report for PCT/US2017/033693, dated Oct. 2, 2017.
Office Action dated Dec. 13, 2017 for U.S. Appl. No. 14/062,054; (pp. 1-15).
Extended European Search Report for EP14740240.8, dated Jul. 28, 2016.
International Search Report for PCT/US2016/012840, dated Aug. 18, 2016.

\* cited by examiner

VAPOR ABLATION SYSTEM WITH A CATHETER HAVING MORE THAN ONE POSITIONING ELEMENT

CROSS-REFERENCE TO RELATED APPLICATIONS

The present application is a continuation application of U.S. patent application Ser. No. 13/486,980, entitled "Method and Apparatus for Tissue Ablation",-filed on Jun. 1, 2012, and issued as U.S. Pat. No. 9,561,066 on Feb. 2, 2017, which is a continuation in-part application of U.S. patent application Ser. No. 12/573,939, filed on Oct. 6, 2009 and entitled "Method and Apparatus for Tissue Ablation", which relies on U.S. Provisional Patent Application No. 61/102,885, filed on Oct. 6, 2008, for priority, all of which are herein incorporated by reference in their entirety.

U.S. patent application Ser. No. 13/486,980 also relies on U.S. Provisional Patent Application No. 61/493,344, entitled "Method and Apparatus for Tissue Ablation", filed on Jun. 3, 2011, and assigned to the applicant of the present invention, for priority, which is herein incorporated by reference in its entirety.

FIELD OF THE INVENTION

The present invention relates to medical apparatus and procedures. More particularly, the present invention relates to a device for ablation of tissue comprising a centering or positioning attachment in order to position the device at a consistent distance from the tissue to be ablated.

BACKGROUND OF THE INVENTION

Colon polyps affect almost 25% of the population over the age of 50. While most polyps are detected on colonoscopy and easily removed using a snare, flat sessile polyps are hard to remove using the snare technique and carry a high risk of complications, such as bleeding and perforation. Recently, with improvement in imaging techniques, more flat polyps are being detected. Endoscopically unresectable polyps require surgical removal. Most colon cancer arises from colon polyps and, safe and complete resection of these polyps is imperative for the prevention of colon cancer.

Barrett's esophagus is a precancerous condition effecting 10-14% of the US population with gastro esophageal reflux disease (GERD) and is the proven precursor lesion of esophageal adenocarcinoma, the fastest rising cancer in the developed nations. The incidence of the cancer has risen over 6 fold in the last 2 decades and mortality has risen by 7 fold. The 5-year mortality from esophageal cancer is 85%. Ablation of Barrett's epithelium has shown to prevent its progression to esophageal cancer.

Dysfunctional uterine bleeding (DUB), or menorrhagia, affects 30% of women in reproductive age. The associated symptoms have considerable impact on a woman's health and quality of life. The condition is typically treated with endometrial ablation or a hysterectomy. The rates of surgical intervention in these women are high. Almost 30% of women in the US will undergo hysterectomy by the age of 60, with menorrhagia or DUB being the cause for surgery in 50-70% of these women. Endometrial ablation techniques have been FDA approved for women with abnormal uterine bleeding and with intramural fibroids less than 2 cm. The presence of submucosal uterine fibroids and a large uterus size have been shown to decrease the efficacy of standard endometrial ablation. Of the five FDA approved global ablation devices (namely, Thermachoice, hydrothermal ablation, Novasure, Her Option, and microwave ablation) only microwave ablation (MEA) has been approved for use where the submucosal fibroids are less than 3 cm and are not occluding the endometrial cavity and, additionally, for large uteri up to 14 cm.

The known ablation treatments for Barrett's esophagus include laser treatment (Ertan et al, Am. J. Gastro., 90:2201-2203 [1995]), ultrasonic ablation (Bremner et al, Gastro. Endo., 43:6 [1996]), photodynamic therapy (PDT) using photo-sensitizer drugs (Overholt et al, Semin. Surq. Oncol., 1:372-376 (1995), multipolar electrocoagulation, such as by use of a bicap probe (Sampliner et al,), argon plasma coagulation (APC;), radiofrequency ablation (Sharma et al. Gastrointest Endosc) and cryoablation (Johnston et al. Gastrointest Endosc). The treatments are delivered with the aid of an endoscope and devices passed through the channel of the endoscope or alongside the endoscope.

Conventional techniques have inherent limitations, however, and have not found widespread clinical applications. First, most of the hand held ablation devices (bicap probe, APC, cryoablation) are point and shoot devices that create small foci of ablation. This ablation mechanism is operator dependent, cumbersome and time consuming. Second, because the target tissue is moving due to patient movement, respiration movement, normal peristalsis and vascular pulsations, the depth of ablation of the target tissue is inconsistent and results in a non-uniform ablation. Superficial ablation results in incomplete ablation with residual neoplastic tissue left behind. Deeper ablation results in complications such as bleeding, stricture formation and perforation. All of these limitations and complications have been reported with conventional devices.

For example, radiofrequency ablation uses a rigid bipolar balloon based electrode and radiofrequency thermal energy. The thermal energy is delivered by direct contact of the electrode with the diseased Barrett's epithelium allowing for a relatively uniform, large area ablation. However, the rigid electrode does not accommodate for variations in esophageal size and is ineffective in ablating lesions within a tortuous esophagus, proximal esophageal lesions as an esophagus narrows toward the top, and lesions in the esophagus at the gastroesophageal junction due to changes in the esophageal diameter. Nodular disease in Barrett's esophagus also cannot be treated using the rigid bipolar RF electrode. Due to its size and rigidity, the electrode cannot be passed through the scope. In addition, sticking of sloughed tissue to the electrode impedes delivery of radiofrequency energy resulting in incomplete ablation. The electrode size is limited to 3 cm, thus requiring repeat applications to treat larger lengths of Barrett's esophagus.

Photodynamic therapy (PDT) is a two part procedure that involves injecting a photo-sensitizer that is absorbed and retained by the neoplastic and pre-neoplastic tissue. The tissue is then exposed to a selected wavelength of light which activates the photo-sensitizer and results in tissue destruction. PDT is associated with complications such as stricture formation and photo-sensitivity which has limited its use to the most advanced stages of the disease. In addition, patchy uptake of the photosensitizer results in incomplete ablation and residual neoplastic tissue.

Cryoablation of the esophageal tissues via direct contact with liquid nitrogen has been studied in both animal models and humans (Rodgers et al, Cryobiology, 22:86-92 (1985); Rodgers et al, Ann. Thorac. Surq. 55:52-7 [1983]) and has been used to treat Barrett's esophagus (Johnston et al. Gastrointest Endosc) and early esophageal cancer (Grana et al, Int. Surg., 66:295 [1981]). A spray catheter that directly sprays liquid $N_2$ or $CO_2$ (cryoablation) or argon (APC) to ablate Barrett's tissue in the esophagus has been described. These techniques suffer the shortcoming of the traditional hand-held devices. Treatment using this probe is cumbersome and requires operator control under direct endoscopic visualization. Continuous movement in the esophagus due to respiration or cardiac or aortic pulsations or movement causes an uneven distribution of the ablative agent and results in non-uniform and/or incomplete ablation. Close or direct contact of the catheter to the surface epithelium may cause deeper tissue injury, resulting in perforation, bleeding or stricture formation. Too distant a placement of the catheter due to esophageal movement will result in incomplete Barrett's ablation, requiring multiple treatment sessions or buried lesions with a continued risk of esophageal cancer. Expansion of cryogenic gas in the esophagus results in uncontrolled retching which may result in esophageal tear or perforation requiring continued suctioning of cryogen.

Colon polyps are usually resected using snare resection with or without the use of monopolar cautery. Flat polyps or residual polyps after snare resection have been treated with argon plasma coagulation or laser treatment. Both of these treatments are inadequate due to the previously mentioned limitations. Hence, most large flat polyps undergo surgical resection due to high risk of bleeding, perforation and residual disease using traditional endoscopic resection or ablation techniques.

Most of the conventional balloon catheters traditionally used for tissue ablation either heat or cool the balloon itself or a heating element such as radio frequency (RF) coils mounted on the balloon. This requires direct contact of the balloon catheter with the ablated surface. When the balloon catheter is deflated, the epithelium sticks to the catheter and sloughs off, thereby causing bleeding. Blood can interfere with the delivery of energy, and therefore acts as an energy sink. In addition, reapplication of energy will result in deeper burn in the area where superficial lining has sloughed. Further, balloon catheters cannot be employed for treatment in non-cylindrical organs, like the uterus or sinuses, and also do not provide non-circumferential or focal ablation in a hollow organ. Additionally, if used with cryogens as ablative agents, which expand exponentially upon being heated, balloon catheters may result in a closed cavity and trap the escape of cryogen, resulting in complications such as perforations and tears.

Accordingly, there is a need in the art for an improved method and system for delivering ablative agents to a tissue surface, for providing a consistent, controlled, and uniform ablation of the target tissue, and for minimizing the adverse side effects of introducing ablative agents into a patient.

SUMMARY OF THE INVENTION

In one embodiment, the present specification discloses a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said snare handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a predefined distance from the tissue to be ablated.

Optionally, the handle has one pressure-resistant port for the attachment of both an ablative agent inlet and an RF feed. The handle has one separate pressure-resistant port for the attachment of an ablative agent inlet and one separate port for the attachment of an RF feed or an electrical feed.

In another embodiment, the present specification discloses a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical field; an insulated catheter that attaches to said pressure-resistant port of said handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a predefined distance from the tissue to be ablated. Optionally, the distal end of said catheter is designed to puncture the target.

In another embodiment, the present specification discloses a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said esophageal probe, containing a shaft through which an ablative agent can travel and one or more ports along its length for the release of said ablative agent; and one or more inflatable positioning balloons at either end of said catheter positioned beyond said one or more ports, wherein said positioning balloons are configured to position said catheter at a predefined distance from the tissue to be ablated.

Optionally, the catheter is dual lumen, wherein a first lumen facilitates the transfer of ablative agent and a second lumen contains an electrode for RF ablation. The catheter has differential insulation along its length.

The present specification is also directed toward a tissue ablation device, comprising: a liquid reservoir, wherein said reservoir includes an outlet connector that can resist at least 1 atm of pressure for the attachment of a reusable cord; a heating component comprising: a length of coiled tubing contained within a heating element, wherein activation of said heating element causes said coiled tubing to increase from a first temperature to a second temperature and wherein said increase causes a conversion of liquid within said coiled tubing to vapor; and an inlet connected to said coiled tubing; an outlet connected to said coiled tubing; and at least one pressure-resistant connection attached to the inlet and/or outlet; a cord connecting the outlet of said reservoir to the inlet of the heating component; a single use cord connecting a pressure-resistant inlet port of a vapor based ablation device to the outlet of said heating component.

In one embodiment, the liquid reservoir is integrated within an operating room equipment generator. In one embodiment, the liquid is water and the vapor is steam.

In one embodiment, the pressure-resistant connections are luer lock connections. In one embodiment, the coiled tubing is copper.

In one embodiment, the tissue ablation device further comprises a foot pedal, wherein only when said foot pedal is pressed, vapor is generated and passed into said single use cord. In another embodiment, only when pressure is removed from said foot pedal, vapor is generated and passed into said single use cord.

In another embodiment, the present specification discloses a vapor ablation system used for supplying vapor to an ablation device, comprising; a single use sterile fluid container with attached compressible tubing used to connect the fluid source to a heating unit in the handle of a vapor ablation catheter. The tubing passes through a pump that delivers the fluid into the heating unit at a predetermined speed. There is present a mechanism such as a unidirectional valve between the fluid container and the heating unit to prevent the backflow of vapor from the heating unit. The heating unit is connected to the ablation catheter to deliver the vapor from the heating unit to the ablation site. The flow of vapor is controlled by a microprocessor. The microprocessor uses a pre-programmed algorithm in an open-loop system or uses information from one or more sensors incorporated in the ablation system in a closed-loop system or both to control delivery of vapor.

In one embodiment the handle of the ablation device is made of a thermally insulating material to prevent thermal injury to the operator. The heating unit is enclosed in the handle. The handle locks into the channel of an endoscope after the catheter is passed through the channel of the endoscope. The operator can than manipulate the catheter by holding the insulated handle or by manipulating the catheter proximal to the insulating handle.

The present specification is also directed toward a vapor ablation system comprising: a container with a sterile liquid therein; a pump in fluid communication with said container; a first filter disposed between and in fluid communication with said container and said pump; a heating component in fluid communication with said pump; a valve disposed between and in fluid communication with said pump and heating container; a catheter in fluid communication with said heating component, said catheter comprising at least one opening at its operational end; and, a microprocessor in operable communication with said pump and said heating component, wherein said microprocessor controls the pump to control a flow rate of the liquid from said container, through said first filter, through said pump, and into said heating component, wherein said liquid is converted into vapor via the transfer of heat from said heating component to said fluid, wherein said conversion of said fluid into said vapor results is a volume expansion and a rise in pressure where said rise in pressure forces said vapor into said catheter and out said at least one opening, and wherein a temperature of said heating component is controlled by said microprocessor.

In one embodiment, the vapor ablation system further comprises at least one sensor on said catheter, wherein information obtained by said sensor is transmitted to said microprocessor, and wherein said information is used by said microprocessor to regulate said pump and said heating component and thereby regulate vapor flow. In one embodiment, the at least one sensor includes one or more of a temperature sensor, flow sensor, or pressure sensor.

In one embodiment, the vapor ablation system further comprises a screw cap on said liquid container and a puncture needle on said first filter, wherein said screw cap is punctured by said puncture needle to provide fluid communication between said container and said first filter.

In one embodiment, the liquid container and catheter are disposable and configured for a single use.

In one embodiment, the fluid container, first filter, pump, heating component, and catheter are connected by sterile tubing and the connections between said pump and said heating component and said heating component and said catheter are pressure resistant.

The present specification is also directed toward a tissue ablation system comprising: a catheter with a proximal end and a distal end and a lumen therebetween, said catheter comprising: a handle proximate the proximal end of said catheter and housing a fluid heating chamber and a heating element enveloping said chamber, a wire extending distally from said heating element and leading to a controller; an insulating sheath extending and covering the length of said catheter and disposed between said handle and said heating element at said distal end of said catheter; and, at least one opening proximate the distal end of said catheter for the passage of vapor; and, a controller operably connected to said heating element via said wire, wherein said controller is capable of modulating energy supplied to said heating element and further wherein said controller is capable of adjusting a flow rate of liquid supplied to said catheter; wherein liquid is supplied to said heating chamber and then converted to vapor within said heating chamber by a transfer of heat from said heating element to said chamber, wherein said conversion of said liquid to vapor results in a volume expansion and a rise in pressure within said catheter, and wherein said rise in pressure pushes said vapor through said catheter and out said at least one opening.

In one embodiment, the tissue ablation system further comprises a pressure resistant fitting attached to the fluid supply and a one-way valve in said pressure resistant fitting to prevent a backflow of vapor into the fluid supply.

In one embodiment, the tissue ablation system further comprises at least one sensor on said catheter, wherein information obtained by said sensor is transmitted to said microprocessor, and wherein said information is used by said microprocessor to regulate said pump and said heating component and thereby regulate vapor flow.

In one embodiment, the tissue ablation system further comprises a metal frame within said catheter, wherein said metal frame is in thermal contact with said heating chamber and conducts heat to said catheter lumen, thereby preventing condensation of said vapor. In various embodiments, the metal frame comprises a metal skeleton with outwardly extending fins at regularly spaced intervals, a metal spiral, or a metal mesh and the metal frame comprises at least one of copper, stainless steel, or another ferric material.

In one embodiment, the heating element comprises a heating block, wherein said heating block is supplied power by said controller.

In various embodiments, the heating element uses one of magnetic induction, microwave, high intensity focused ultrasound, or infrared energy to heat said heating chamber and the fluid therein.

BRIEF DESCRIPTION OF THE DRAWINGS

These and other features and advantages of the present invention will be further appreciated, as they become better understood by reference to the detailed description when considered in connection with the accompanying drawings, wherein.

DETAILED DESCRIPTION OF THE INVENTION

Figure 1:
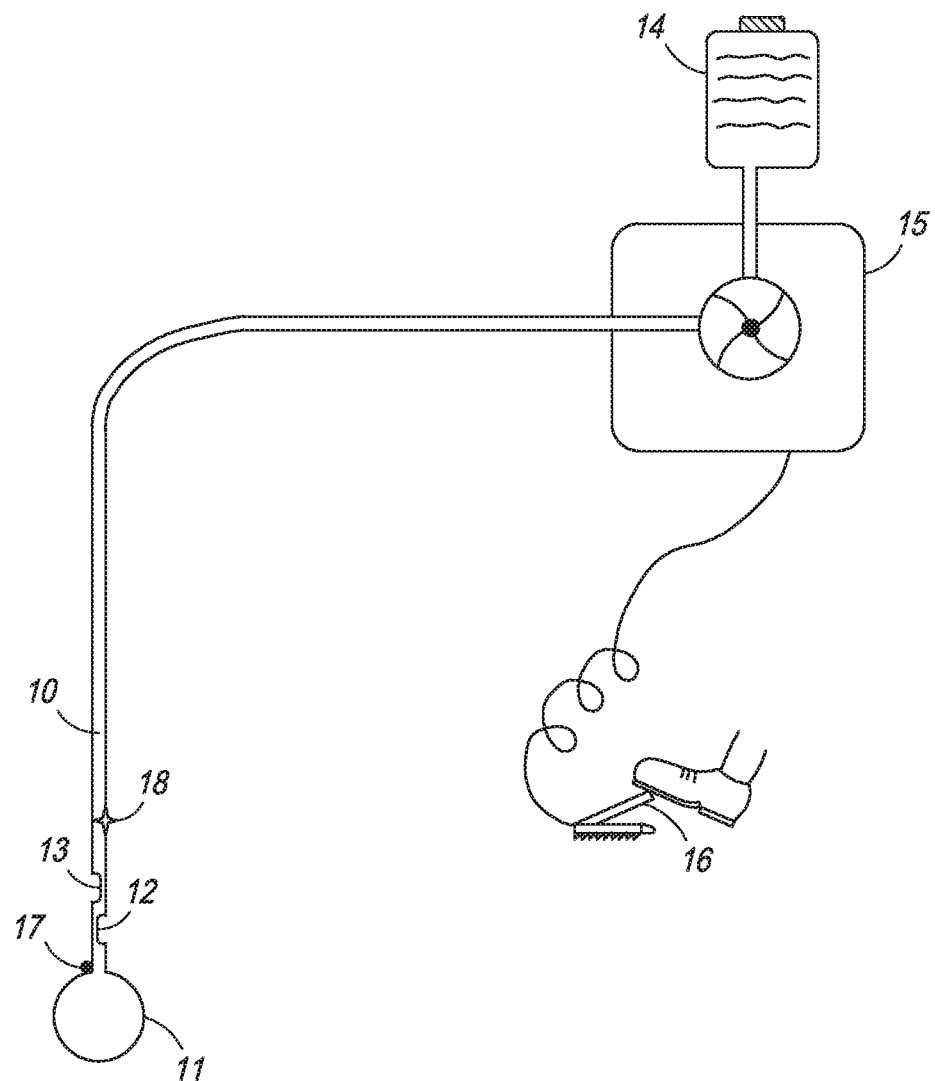
FIG. 1 illustrates an ablation device, in accordance with an embodiment of the present invention.

The present invention is directed toward an ablation device comprising a catheter with one or more centering or positioning attachments at one or more ends of the catheter to affix the catheter and its infusion port at a fixed distance from the ablative tissue which is not affected by the movements of the organ. The arrangement of one or more spray ports allows for uniform spray of the ablative agent producing a uniform ablation of a large area, such as encountered in Barrett's esophagus. The flow of ablative agent is controlled by the microprocessor and depends upon one or more of the length or area of tissue to be ablated, type and depth of tissue to be ablated, and distance of the infusion port from or in the tissue to be ablated.

The present invention is also directed toward a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated.

In one embodiment, the handle has one pressure-resistant port for the attachment of both an ablative agent inlet and an RF feed. In another embodiment, the handle has one separate pressure-resistant port for the attachment of an ablative agent inlet and one separate port for the attachment of an RF feed or an electrical feed.

The present invention is also directed toward a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated. In one embodiment, the distal end of said catheter is designed to puncture the target tissue to deliver ablative agent to the correct depth and location.

The present invention is also directed toward a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said esophageal probe, containing a shaft through which an ablative agent can travel and one or more ports along its length for the release of said ablative agent; and, one or more inflatable positioning balloons at either end of said catheter positioned beyond said one or more ports, wherein said positioning balloons are configured to position said catheter at a predefined distance from the tissue to be ablated.

In one embodiment, the catheter is dual lumen, wherein a first lumen facilitates the transfer of ablative agent and a second lumen contains an electrode for RF ablation.

In one embodiment, the catheter has differential insulation along its length.

The present invention is also directed toward a vapor delivery system used for supplying vapor to an ablation device, comprising: a liquid reservoir, wherein said reservoir includes a pressure-resistant outlet connector for the attachment of a reusable cord; a reusable cord connecting the outlet of said reservoir to the inlet of a heating component; a powered heating component containing a length of coiled tubing within for the conversion of liquid to vapor and pressure-resistant connections on both the inlet and outlet ends of said heating component; and, a single use cord connecting a pressure-resistant inlet port of a vapor based ablation device to the outlet of said heating component.

In one embodiment, the liquid reservoir is integrated within an operating room equipment generator.

In one embodiment, the liquid is water and resultant said vapor is steam.

In one embodiment, the pressure-resistant connections are of a luer lock type.

In one embodiment, the coiled tubing is copper.

In one embodiment, the vapor delivery system used for supplying vapor to an ablation device further comprises a foot pedal used by the operator to deliver more vapor to the ablation device.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present FIG. 1 illustrates an ablation device, in accordance with an embodiment of the present invention. The ablation device comprises a catheter 10 having a distal centering or positioning attachment which is an inflatable balloon 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. In one embodiment, the infusion ports 12 can direct the ablative agent at different angles. Ablative agent is stored in a reservoir 14 connected to the catheter 10. Delivery of the ablative agent is controlled by a microprocessor 15 and initiation of the treatment is controlled by a treating physician using an input device, such as a foot-paddle 16. In other embodiments, the input device could be a voice recognition system (that is responsive to commands such as "start", "more", "less", etc.), a mouse, a switch, footpad, or any other input device known to persons of ordinary skill in the art. In one embodiment, microprocessor 15 translates signals from the input device, such as pressure being placed on the foot-paddle or vocal commands to provide "more" or "less" ablative agent, into control signals that determine whether more or less ablative agent is dispensed. Optional sensor 17 monitors changes in an ablative tissue or its vicinity to guide flow of ablative agent. In one embodiment, optional sensor 17 also includes a temperature sensor. Optional infrared, electromagnetic, acoustic or radiofrequency energy emitters and sensors 18 measure the dimensions of the hollow organ.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

In one embodiment, the inflatable balloon has a diameter of between 1 mm and 10 cm. In one embodiment, the inflatable balloon is separated from the ports by a distance of 1 mm to 10 cm. In one embodiment, the size of the port openings is between 1 μm and 1 cm. It should be appreciated that the inflatable balloon is used to fix the device and therefore is configured to not contact the ablated area. The inflatable balloon can be any shape that contacts the hollow organ at 3 or more points. One of ordinary skill in the art will recognize that, using triangulation, one can calculate the distance of the catheter from the lesion. Alternatively, the infrared, electromagnetic, acoustic or radiofrequency energy emitters and sensors 18 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. It should be appreciated that the emitter and sensor 18 can be incorporated into a single transceiver that is capable of both emitting energy and detecting the reflected energy.

Figure 2B:
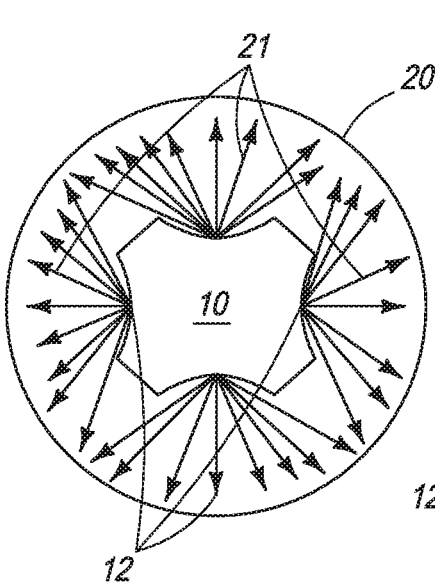
FIG. 2B illustrates a cross section of a port on the ablation device, in accordance with an embodiment of the present invention.
Figure 2C:
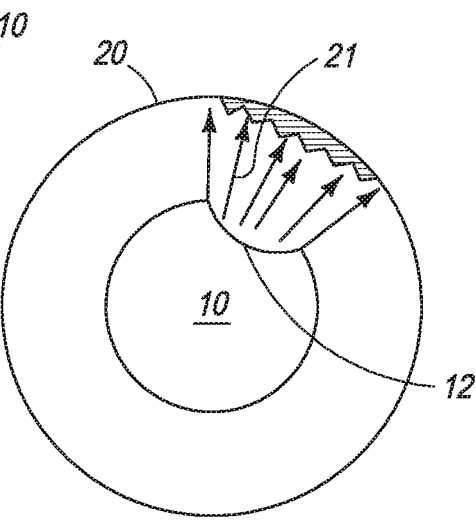
FIG. 2C illustrates a cross section of a port on the ablation device, in accordance with another embodiment of the present invention.
Figure 2A:
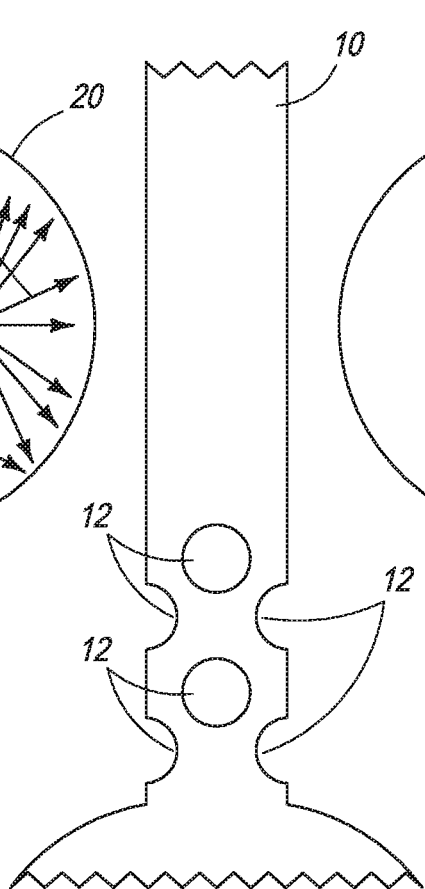
FIG. 2A illustrates a longitudinal section of an ablation device with ports distributed thereon.

FIG. 2A illustrates a longitudinal section of the ablation device, depicting a distribution of infusion ports. FIG. 2B illustrates a cross section of a distribution of infusion ports on the ablation device, in accordance with an embodiment of the present invention. The longitudinal and cross sectional view of the catheter 10 as illustrated in FIGS. 2A and 2B respectively, show one arrangement of the infusion ports 12 to produce a uniform distribution of ablative agent 21 (shown in FIG. 2B) in order to provide a circumferential area of ablation in a hollow organ 20. FIG. 2C illustrates a cross section of a distribution of infusion ports on the ablation device, in accordance with another embodiment of the present invention. The arrangement of the infusion ports 12 as illustrated in FIG. 2C produce a focal distribution of ablative agent 21 and a focal area of ablation in a hollow organ 20.

For all embodiments described herein, it should be appreciated that the size of the port, number of ports, and distance between the ports will be determined by the volume of ablative agent needed, pressure that the hollow organ can withstand, size of the hollow organ as measured by the distance of the surface from the port, length of the tissue to be ablated (which is roughly the surface area to be ablated), characteristics of the tissue to be ablated and depth of ablation needed. In one embodiment, there is at least one port opening that has a diameter between 1 μm and 1 cm. In another embodiment, there are two or more port openings that have a diameter between 1 μm and 1 cm and that are equally spaced around the perimeter of the device.

Figure 2D:
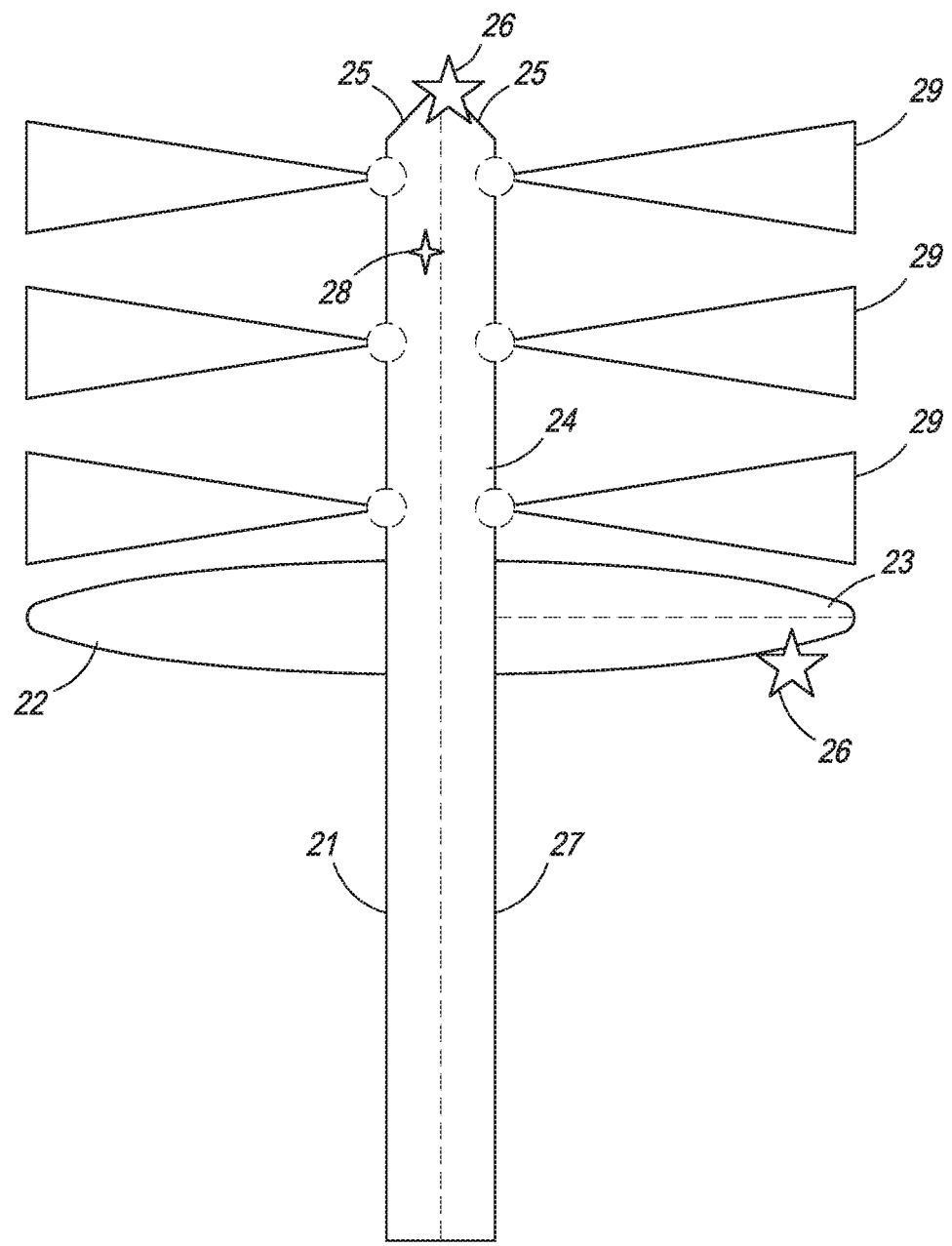
FIG. 2D illustrates a catheter of the ablation device, in accordance with an embodiment of the present invention.

FIG. 2D illustrates another embodiment of the ablation device. The vapor ablation catheter comprises an insulated catheter 21 with one or more positioning attachments 22 of known length 23. The vapor ablation catheter has one or more vapor infusion ports 25. The length 24 of the vapor ablation catheter 21 with infusion ports 25 is determined by the length or area of the tissue to be ablated. Vapor 29 is delivered through the vapor infusion ports 25. The catheter 21 is preferably positioned in the center of the positioning attachment 22, and the infusion ports 25 are arranged circumferentially for circumferential ablation and delivery of vapor. In another embodiment, the catheter 21 can be positioned toward the periphery of the positioning attachment 22 and the infusion ports 25 can be arranged non-circumferentially, preferably linearly on one side for focal ablation and delivery of vapor. The positioning attachment 22 is one of an inflatable balloon, a wire mesh disc with or without an insulated membrane covering the disc, a cone shaped attachment, a ring shaped attachment or a freeform attachment designed to fit the desired hollow body organ or hollow body passage, as further described below. Optional infrared, electromagnetic, acoustic or radiofrequency energy emitters and sensors 28 are incorporated to measure the dimensions of the hollow organ.

The vapor ablation catheter may also comprise an optional coaxial sheet 27 to restrain the positioning attachment 22 in a manner comparable to a coronary metal stent. In one embodiment, the sheet is made of memory metal or memory material with a compressed linear form and a non-compressed form in the shape of the positioning attachment. Alternatively, the channel of an endoscope may perform the function of restraining the positioning attachment 22 by, for example, acting as a constraining sheath. Optional sensor 26 is deployed on the catheter to measure changes associated with vapor delivery or ablation. The sensor is one of temperature, pressure, photo or chemical sensor.

Optionally, one or more, infrared, electromagnetic, acoustic or radiofrequency energy emitters and sensors 28 can measure the dimensions of the hollow organ. The infrared, electromagnetic, acoustic or radiofrequency energy is emitted from the emitter 28 and is reflected back from the tissue to the detector in the emitter 28. The reflected data can be used to determine the dimension of the hollow cavity. The measurement is performed at one or multiple points to get an accurate estimate of the dimension of the hollow organ. The data can also be used to create a topographic representation of the hollow organ. Additional data from diagnostic tests can be used to validate or add to the data from the above measurements.

Figure 2E:
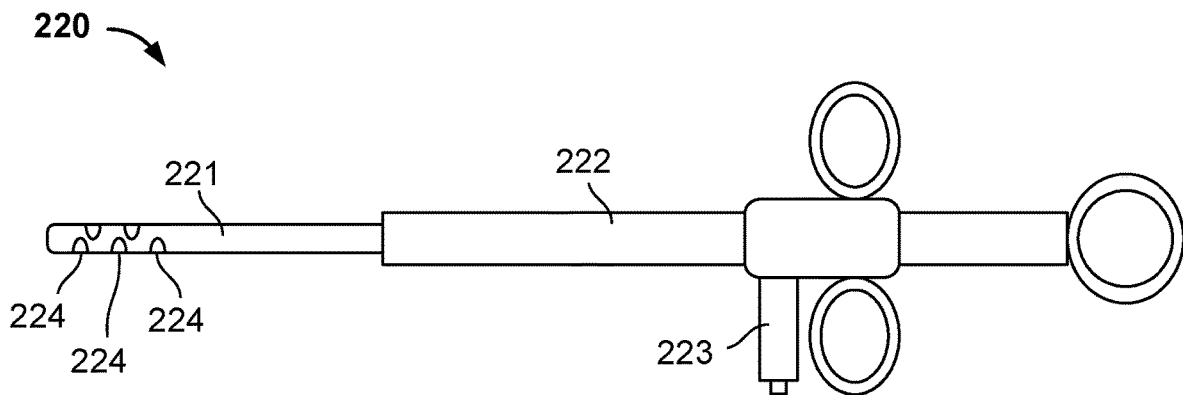
FIG. 2E illustrates an ablation device in the form of a catheter extending from a conventional snare handle, in accordance with an embodiment of the present invention.

FIG. 2E illustrates an ablation device 220 in the form of a catheter 221 extending from a conventional handle 222, in accordance with an embodiment of the present invention. The catheter 221 is of a type as described above and extends from and attaches to the handle 222. In one embodiment, the catheter 221 is insulated to protect the user from burns that could result from hot vapor heating the catheter. In one embodiment, the catheter is composed of a material that will ensure that the outer temperature of the catheter will remain below 60° C. during use. The handle 222 includes a pressure resistant port at the point of attachment with the catheter 221. The handle 222 also includes a flow channel within that directs vapor through to the catheter 221.

In one embodiment, the snare handle 222 includes a single attachment port 223 for the connection of a vapor stream and an RF feed. In another embodiment (not shown), the snare handle includes two separate attachment ports for the connection of a vapor stream and an RF feed. The attachment port 223 interfaces with the vapor supply cord via pressure-resistant connectors. In one embodiment, the connectors are of a luer lock type. In one embodiment, the catheter 221 is a dual lumen catheter. The first lumen serves to deliver vapor to the site of ablation. In one embodiment, the vapor is released through small ports 224 positioned proximate the distal end of the catheter 221. The distal end of the catheter 221 is designed so that it can puncture the tissue to deliver vapor to the desired depth and location within the target tissue. In one embodiment, the distal end of the catheter 221 tapers to a point. The second lumen houses the electrode used for RF ablation. In one embodiment, the delivery of vapor or RF waves is achieved through the use of a microprocessor. In another embodiment, the user can release vapor or subject the target tissue to RF waves by the use of actuators (not shown) on the handle 222. In one embodiment, the catheter has varying or differential insulation along its length. In one embodiment, the ablation device 220 includes a mechanism in which a snare to grasp the tissue to be ablated and sizing the tissue in the snare is used to determine the amount of vapor to be delivered.

Figure 2F:
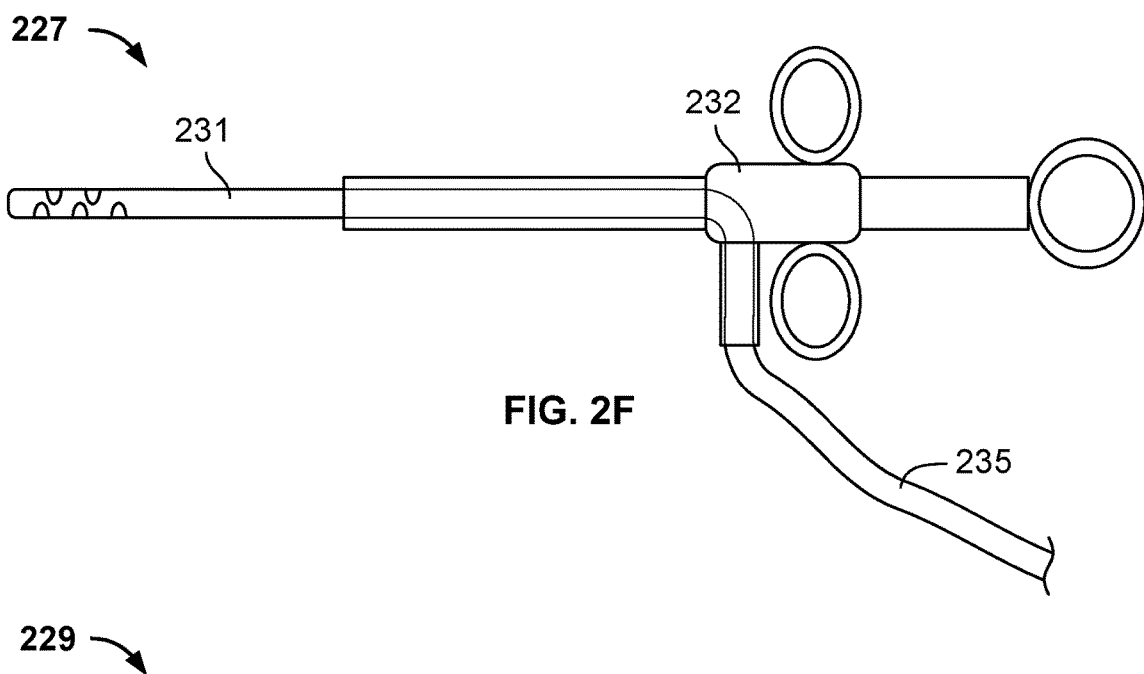
FIG. 2F illustrates a cross section of an ablation device in the form of a catheter extending from a conventional snare handle with a pre-attached cord, in accordance with another embodiment of the present invention.

FIG. 2F illustrates a cross section of an ablation device 227 in the form of a catheter 231 extending from a conventional handle 232 with a pre-attached cord 235, in accordance with another embodiment of the present invention. The cord 235 attaches directly to the vapor delivery system, eliminating one interface between the system and the ablation device and thereby decreasing the chance of system failure as a result of disconnection. In this embodiment, the handle 232 includes a separate attachment port (not shown) for the RF or an electric feed.

Figure 2G:
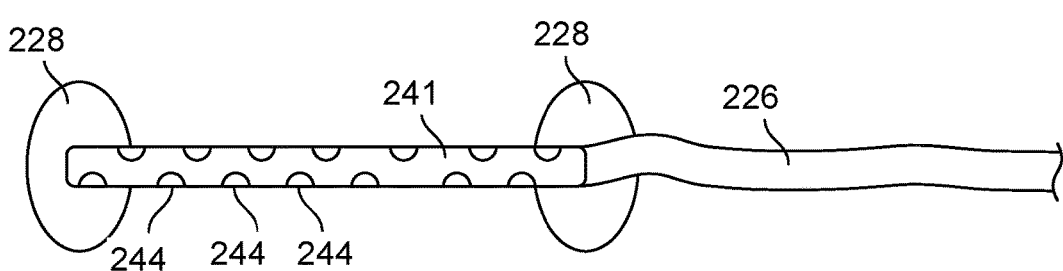
FIG. 2G illustrates an ablation device in the form of a catheter extending from a conventional esophageal probe, in accordance with an embodiment of the present invention.

FIG. 2G illustrates an ablation device 229 in the form of a catheter 241 extending from a conventional esophageal probe 226, in accordance with an embodiment of the present invention. In one embodiment, the catheter 241 is insulated and receives vapor from a flow channel contained within the probe 226. The catheter 241 includes a multitude of small ports 244 for the delivery of vapor to the target tissue. The delivery of vapor is controlled by a microprocessor. In one embodiment, the catheter 241 also includes two inflatable balloons 228, one at its distal end beyond the last vapor port 244, and one at its proximal end, proximate the catheter's 241 attachment to the probe 226. All vapor ports are positioned between these two balloons. Once the device 229 is inserted within the esophagus, the balloons 228 are inflated to keep the catheter 241 positioned and to contain the vapor within the desired treatment area. In one embodiment, the balloons must be separated from the ablation region by a distance of greater than 0 mm, preferably 1 mm and ideally 1 cm. In one embodiment, the diameter of each balloon when inflated is in the range of 10 to 100 mm, preferably 15-40 mm, although one of ordinary skill in the art would appreciate that the precise dimensions are dependent on the size of the patient's esophagus.

In one embodiment, the catheter 241 attached to the esophageal probe 226 is a dual lumen catheter. The first lumen serves to deliver vapor to the site of ablation as described above. The second lumen houses the electrode used for RF ablation.

Figure 3A:
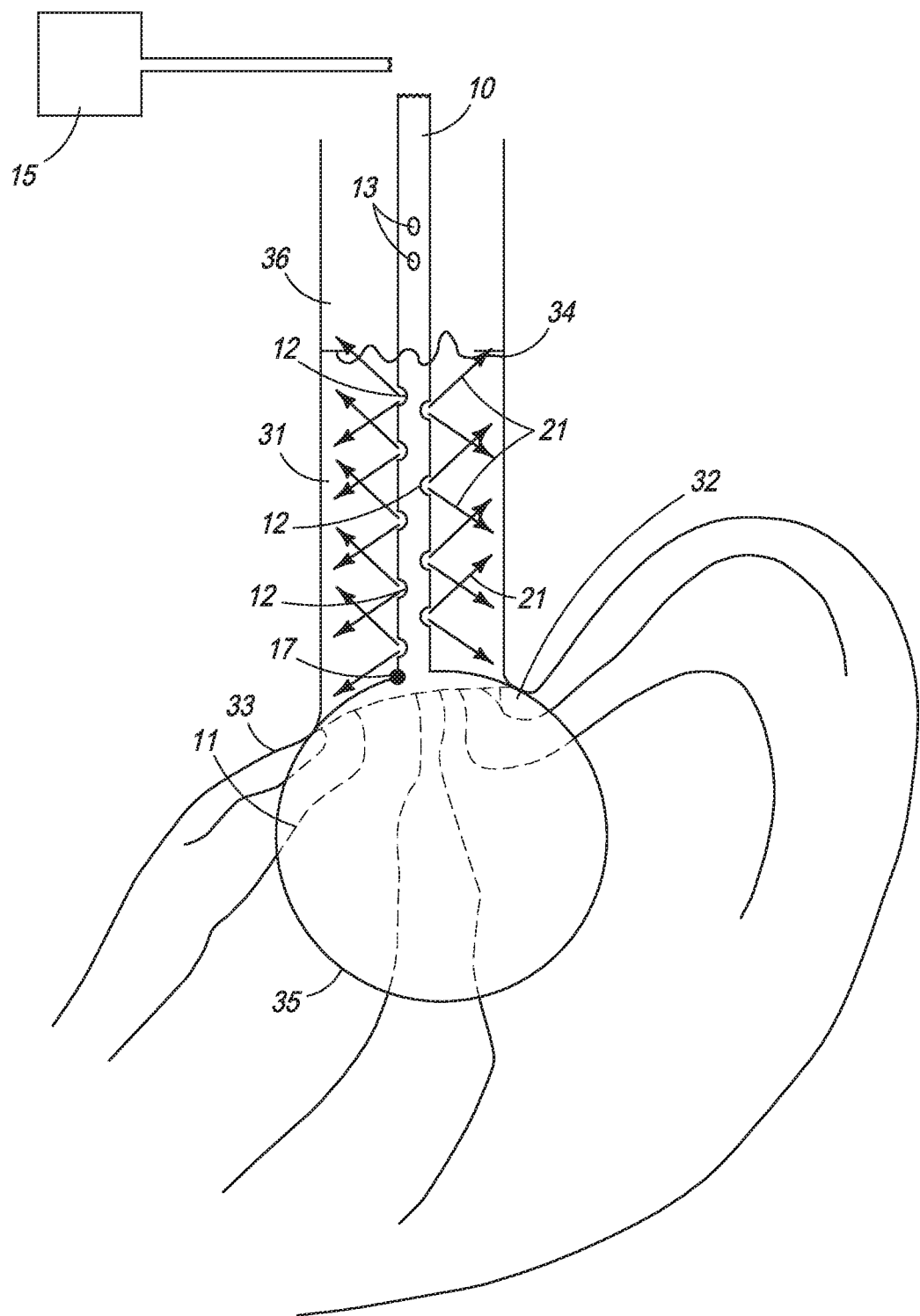
FIG. 3A illustrates the ablation device placed in an upper gastrointestinal tract with Barrett's esophagus to selectively ablate the Barrett's tissue, in accordance with an embodiment of the present invention.

FIG. 3A illustrates the ablation device placed in an upper gastrointestinal tract with Barrett's esophagus to selectively ablate the Barrett's tissue, in accordance with an embodiment of the present invention. The upper gastrointestinal tract comprises Barrett's esophagus 31, gastric cardia 32, gastroesophageal junction 33 and displaced squamo-columnar junction 34. The area between the gastroesophageal junction 33 and the displaced squamo-columnar junction 34 is Barrett's esophagus 31, which is targeted for ablation. Distal to the cardia 32 is the stomach 35 and proximal to the cardia 32 is the esophagus 36. The ablation device is passed into the esophagus 36 and the positioning device 11 is placed in the gastric cardia 32 abutting the gastroesophageal junction 33. This affixes the ablation catheter 10 and its ports 12 in the center of the esophagus 36 and allows for uniform delivery of the ablative agent 21 to the Barrett's esophagus 31.

In one embodiment, the positioning device is first affixed to an anatomical structure, not being subjected to ablation, before ablation occurs. Where the patient is undergoing circumferential ablation or first time ablation, the positioning attachment is preferably placed in the gastric cardia, abutting the gastroesophageal junction. Where the patient is undergoing a focal ablation of any residual disease, it is preferable to use the catheter system shown in FIG. 4B, as discussed below. In one embodiment, the positioning attachment must be separated from the ablation region by a distance of greater than 0 mm, preferably 1 mm and ideally 1 cm. In one embodiment, the size of the positioning device is in the range of 10 to 100 mm, preferably 20-40 mm, although one of ordinary skill in the art would appreciate that the precise dimensions are dependent on the size of the patient's esophagus.

The delivery of ablative agent 21 through the infusion port 12 is controlled by the microprocessor 15 coupled with the ablation device. The delivery of ablative agent is guided by predetermined programmatic instructions, depending on the tissue to be ablated and the depth of ablation required. In one embodiment, the target procedural temperature will need to be between −100 degrees Celsius and 200 degrees Celsius, preferably between 50 degrees Celsius and 75 degrees Celsius, as further shown in the dosimetery table below. In one embodiment, esophageal pressure should not exceed 5 atm, and is preferably below 0.5 atm. In one embodiment, the target procedural temperature is achieved in less than 1 minute, preferably in less than 5 seconds, and is capable of being maintained for up to 10 minutes, preferably 1 to 10 seconds, and then cooled to body temperature. One of ordinary skill in the art would appreciate that the treatment can be repeated until the desired ablation effect is achieved.

Figure 3B:
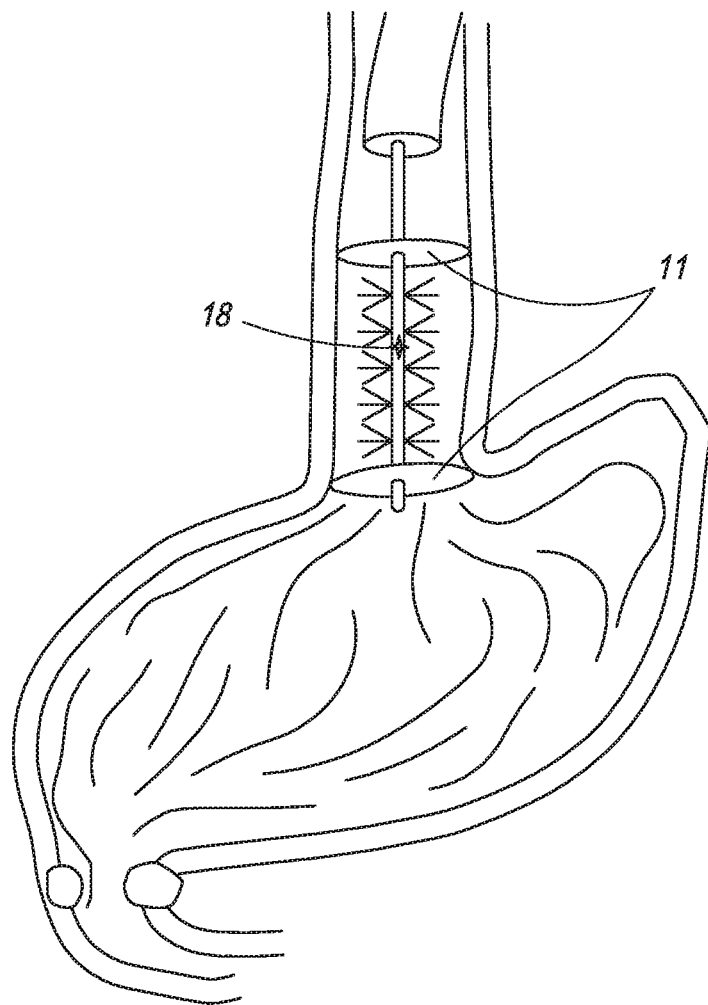
FIG. 3B illustrates the ablation device placed in an upper gastrointestinal tract with Barrett's esophagus to selectively ablate the Barrett's tissue, in accordance with another embodiment of the present invention.

Optional sensor 17 monitors intraluminal parameters such as temperature and pressure and can increase or decrease the flow of ablative agent 21 through the infusion port 12 to obtain adequate heating or cooling, resulting in adequate ablation. The sensor 17 monitors intraluminal parameters such as temperature and pressure and can increase or decrease the removal of ablative agent 21 through the optional suction port 13 to obtain adequate heating or cooling resulting in adequate ablation of Barrett's esophagus 31. FIG. 3B illustrates the ablation device placed in an upper gastrointestinal tract with Barrett's esophagus to selectively ablate the Barrett's tissue, in accordance with another embodiment of the present invention. As illustrated in FIG. 3B, the positioning device 11 is a wire mesh disc. In one embodiment, the positioning attachment must be separated from the ablation region by a distance of greater than 0 mm, preferably 1 mm and ideally 1 cm. In one embodiment, the positioning attachment is removably affixed to the cardia or gastroesophageal (EG) junction (for the distal attachment) or in the esophagus by a distance of greater than 0.1 mm, preferably around 1 cm, above the proximal most extent of the Barrett's tissue (for the proximal attachment).

FIG. 3B is another embodiment of the Barrett's ablation device where the positioning element 11 is a wire mesh disc. The wire mesh may have an optional insulated membrane to prevent the escape of the ablative agent. In the current embodiment, two wire mesh discs are used to center the ablation catheter in the esophagus. The distance between the two discs is determined by the length of the tissue to be ablated which, in this case, would be the length of the Barrett's esophagus. Optional infrared, electromagnetic, acoustic or radiofrequency energy emitters and sensors 18 are incorporated to measure the diameter of the esophagus.

Figure 3C:
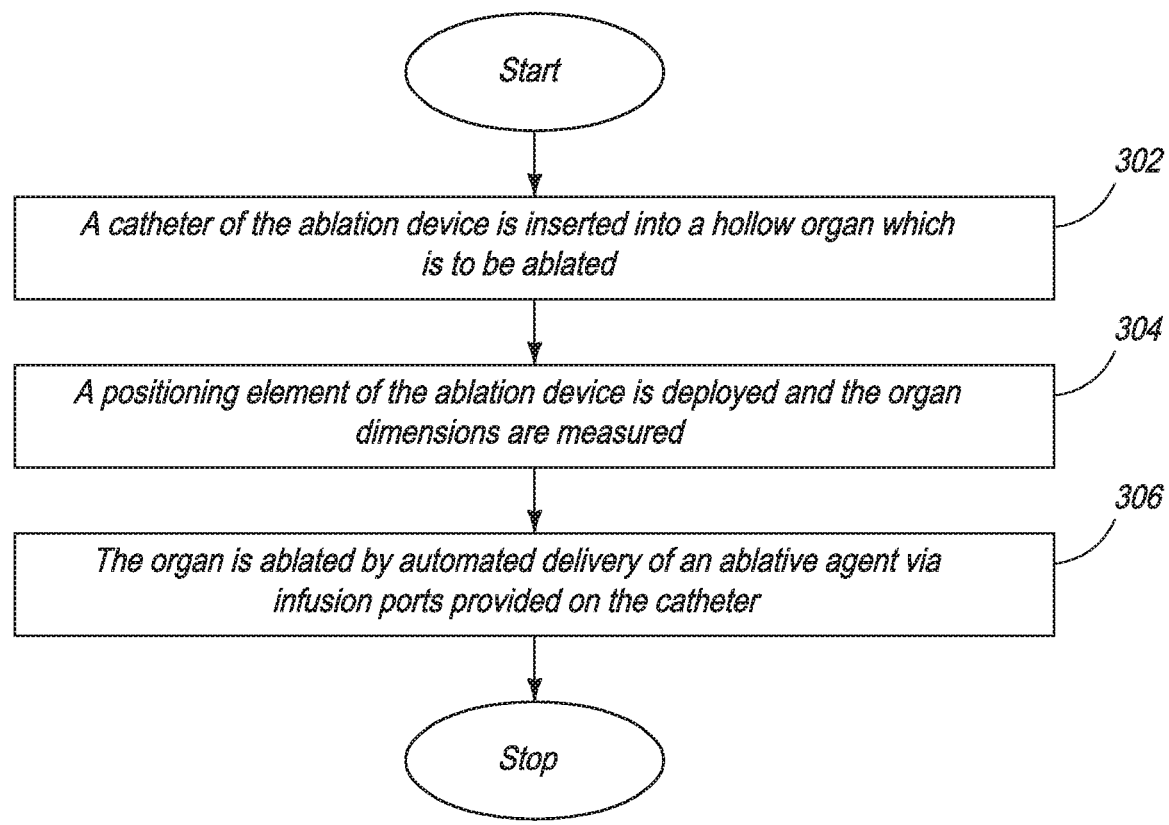
FIG. 3C is a flowchart illustrating the basic procedural steps for using the ablation device, in accordance with an embodiment of the present invention.

FIG. 3C is a flowchart illustrating the basic procedural steps for using the ablation device, in accordance with an embodiment of the present invention. At step 302, a catheter of the ablation device is inserted into an organ which is to be ablated. For example, in order to perform ablation in a Barrett's esophagus of a patient, the catheter is inserted into the Barrett's esophagus via the esophagus of the patient.

At step 304, a positioning element of the ablation device is deployed and organ dimensions are measured. In an embodiment, where the positioning element is a balloon, the balloon is inflated in order to position the ablation device at a known fixed distance from the tissue to be ablated. In various embodiments, the diameter of the hollow organ may be predetermined by using radiological tests such as barium X-rays or computer tomography (CT) scan, or by using pressure volume cycle, i.e. by determining volume needed to raise pressure to a fixed level (for example, 1 atm) in a fixed volume balloon. In another embodiment, where the positioning device is disc shaped, circumferential rings are provided in order to visually communicate to an operating physician the diameter of the hollow organ. In various embodiments of the present invention, the positioning device enables centering of the catheter of the ablation device in a non-cylindrical body cavity, and the volume of the cavity is measured by the length of catheter or a uterine sound.

Optionally, one or more infrared, electromagnetic, acoustic or radiofrequency energy emitters and sensors can be used to measure the dimensions of the hollow organ. The infrared, electromagnetic, acoustic or radiofrequency energy is emitted from the emitter and is reflected back from the tissue to a detector in the emitter. The reflected data can be used to determine the dimensions of the hollow cavity. The measurement can be performed at one or multiple points to get an accurate estimate of the dimensions of the hollow organ. The data from multiple points can also be used to create a topographic representation of the hollow organ or to calculate the volume of the hollow organ.

In one embodiment, the positioning attachment must be separated from the ports by a distance of 0 mm or greater, preferably greater than 0.1 mm, and more preferably 1 cm. The size of the positioning device depends on the hollow organ being ablated and ranges from 1 mm to 10 cm. In one embodiment, the diameter of the positioning element is between 0.01 mm and 100 mm. In one embodiment, the first positioning element comprises a circular body with a diameter between 0.01 mm and 10 cm.

At step 306, the organ is ablated by automated delivery of an ablative agent, such as steam, via infusion ports provided on the catheter. The delivery of the ablative agent through the infusion ports is controlled by a microprocessor coupled with the ablation device. The delivery of ablative agent is guided by predetermined programmatic instructions depending on the tissue to be ablated and the depth of ablation required. In an embodiment of the present invention where the ablative agent is steam, the dose of the ablative agent is determined by conducting dosimetery study to determine the dose to ablate endometrial tissue. The variable that enables determination of total dose of ablative agent is the volume (or mass) of the tissue to be treated which is calculated by using the length of the catheter and diameter of the organ (for cylindrical organs). The determined dose of ablative agent is then delivered using a micro-processor controlled steam generator. Optionally, the delivery of the ablative agent can be controlled by the operator using predetermined dosimetry parameters.

In one embodiment, the dose is provided by first determining what the disorder being treated is and what the desired tissue effect is, and then finding the corresponding temperature, as shown in Tables 1 and 2, below.

TABLE 1

| Temp in ° C. | Tissue Effect |
| --- | --- |
| 37-40 | No significant tissue effect |
| 41-44 | Reversible cell damage in few hours |
| 45-49 | Irreversible cell damage at shorter intervals |
| 50-69 | Irreversible cell damage -ablation necrosis at shorter intervals |
| 70 | Threshold temp for tissue shrinkage, H-bond breakage |
| 70-99 | Coagulation and Hemostasis |
| 100-200 | Desiccation and Carbonization of tissue |
| >200 | Charring of tissue glucose |

TABLE 2

| Disorder | Max. Temp in ° C. |
| --- | --- |
| ENT/Pulmonary | |
| Nasal Polyp | 60-80 |
| Turbinectomy | 70-85 |
| Bullous Disease | 70-85 |
| Lung Reduction | 70-85 |

TABLE 2-continued

| Disorder | Max. Temp in ° C. |
| --- | --- |
| Genitourinary | |
| Uterine Menorrhagia | 80-90 |
| Endometriosis | 80-90 |
| Uterine Fibroids | 90-100 |
| Benign Prostatic Hypertrophy | 90-100 |
| Gastroenterology | |
| Barrett's Esophagus | 60-75 |
| Esophageal Dysplasia | 60-80 |
| Vascular GI Disorders | 55-75 |
| Flat Polyps | 60-80 |

In addition, the depth of ablation desired determines the holding time at the maximum temperature. For superficial ablation (Barrett), the holding time at the maximum temperature is very short (flash burn) and does not allow for heat to transfer to the deeper layers. This will prevent damage to deeper normal tissue and hence prevent patient discomfort and complications. For deeper tissue ablation, the holding time at the maximum temperature will be longer, thereby allowing the heat to percolate deeper.

Figure 4A:
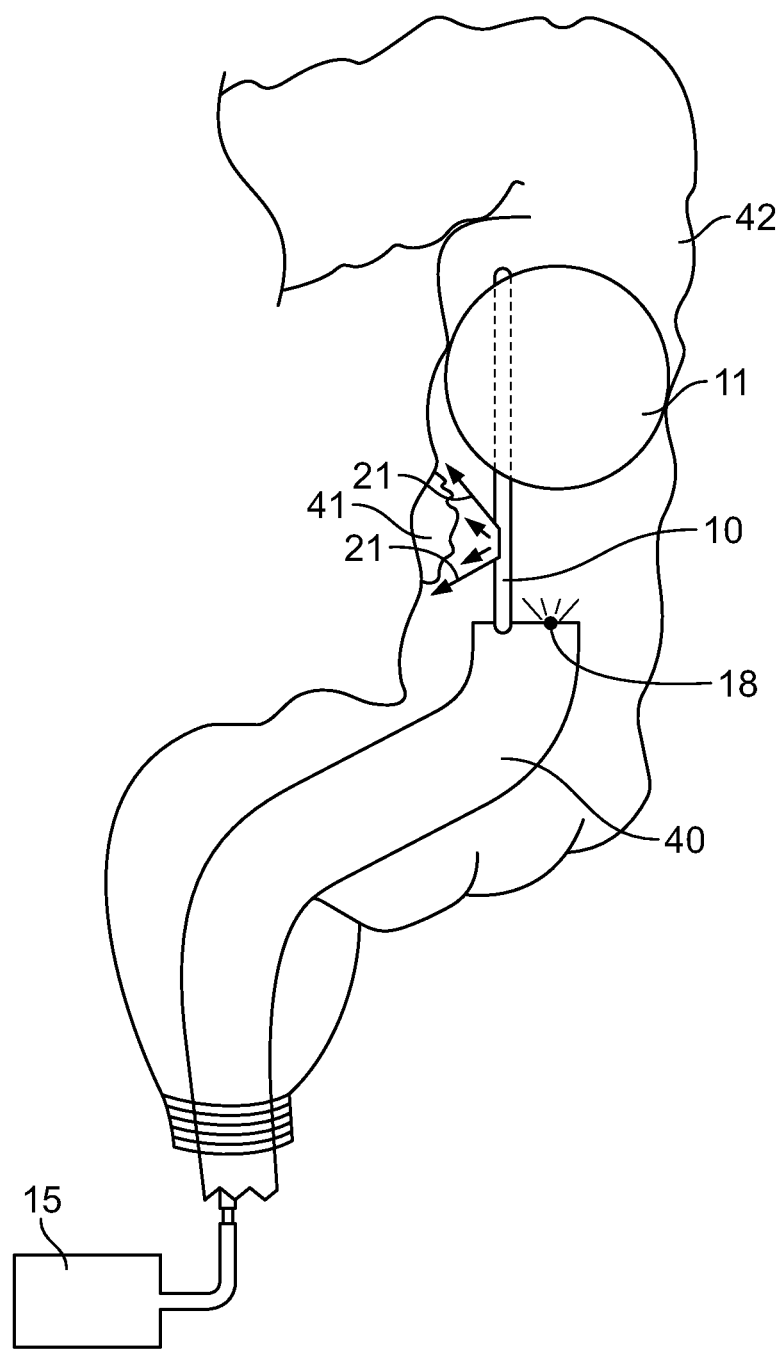
FIG. 4A illustrates the ablation device placed in a colon to ablate a flat colon polyp, in accordance with an embodiment of the present invention.

FIG. 4A illustrates the ablation device placed in a colon to ablate a flat colon polyp, in accordance with an embodiment of the present invention. The ablation catheter 10 is passed through a colonoscope 40. The positioning device 11 is placed proximal, with respect to the patient's GI tract, to a flat colonic polyp 41 which is to be ablated, in the normal colon 42. The positioning device 11 is one of an inflatable balloon, a wire mesh disc with or without an insulated membrane covering the disc, a cone shaped attachment, a ring shaped attachment or a freeform attachment designed to fit the colonic lumen. The positioning device 11 has the catheter 10 located toward the periphery of the positioning device 11 placing it closer to the polyp 41 targeted for non-circumferential ablation. Hence, the positioning device 11 fixes the catheter to the colon 42 at a predetermined distance from the polyp 41 for uniform and focused delivery of the ablative agent 21. The delivery of ablative agent 21 through the infusion port 12 is controlled by the microprocessor 15 attached to the ablation device and depends on tissue and the depth of ablation required. The delivery of ablative agent 21 is guided by predetermined programmatic instructions depending on the tissue to be ablated and the area and depth of ablation required. Optional infrared, electromagnetic, acoustic or radiofrequency energy emitters and sensors 18 are incorporated to measure the diameter of the colon. The ablation device allows for focal ablation of diseased polyp mucosa without damaging the normal colonic mucosa located away from the catheter ports.

In one embodiment, the positioning attachment must be separated from the ablation region by a distance of greater than 0.1 mm, ideally more than 5 mm. In one embodiment, the positioning element is proximal, with respect to the patient's GI tract, to the colon polyp.

Figure 4B:
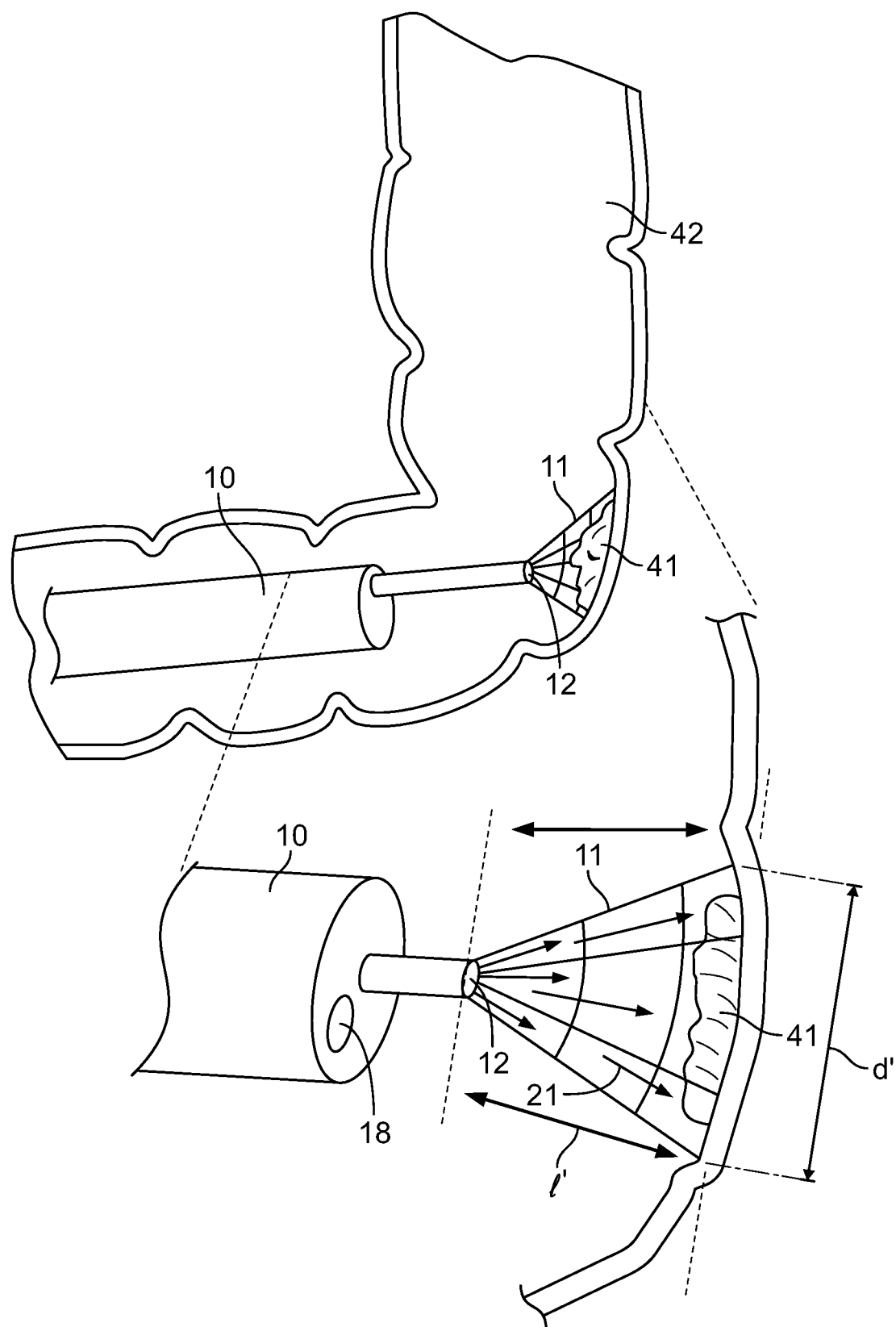
FIG. 4B illustrates the ablation device placed in a colon to ablate a flat colon polyp, in accordance with another embodiment of the present invention.

FIG. 4B illustrates the ablation device placed in a colon 42 to ablate a flat colon polyp 41, in accordance with another embodiment of the present invention. As illustrated in FIG. 4B, the positioning device 11 is a conical attachment at the tip of the catheter 10. The conical attachment has a known length 'l' and diameter 'd' that is used to calculate the amount of thermal energy needed to ablate the flat colon polyp 41. Ablative agent 21 is directed from the infusion port 12 to polyp 41 by the positioning device 11. In one embodiment, the positioning attachment 11 must be separated from the ablation region by a distance of greater than 0.1 mm, preferably 1 mm and more preferably 1 cm. In one embodiment, the length '1' is greater than 0.1 mm, preferably between 5 and 10 mm. In one embodiment, diameter 'd' depends on the size of the polyp and can be between 1 mm and 10 cm, preferably 1 to 5 cm. Optional infrared, electromagnetic, acoustic or radiofrequency energy emitters and sensors 18 are incorporated to measure the diameter of the colon. This embodiment can also be used to ablate residual neoplastic tissue at the edges after endoscopic snare resection of a large sessile colon polyp.

Figure 5A:
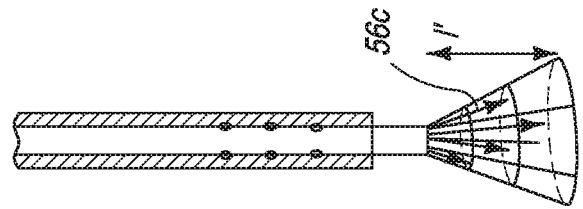
FIG. 5A illustrates the ablation device with a coaxial catheter design, in accordance with an embodiment of the present invention.
Figure 5B:
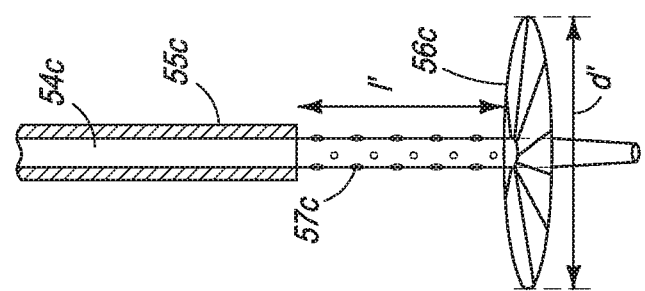
FIG. 5B illustrates a partially deployed positioning device, in accordance with an embodiment of the present invention.

FIG. 5A illustrates the ablation device with a coaxial catheter design, in accordance with an embodiment of the present invention. The coaxial design has a handle 52a, an infusion port 53a, an inner sheath 54a and an outer sheath 55a. The outer sheath 55a is used to constrain the positioning device 56a in the closed position and encompasses ports 57a. FIG. 5B shows a partially deployed positioning device 56b, with the ports 57b still within the outer sheath 55b. The positioning device 56b is partially deployed by pushing the catheter 54b out of sheath 55b.

Figure 5C:
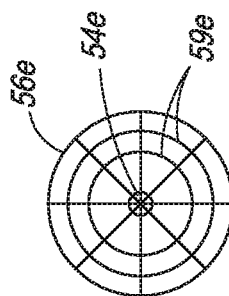
FIG. 5C illustrates a completely deployed positioning device, in accordance with an embodiment of the present invention.
Figure 5D:
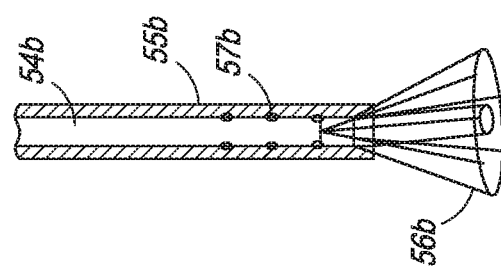
FIG. 5D illustrates the ablation device with a conical positioning element, in accordance with an embodiment of the present invention.
Figure 5E:
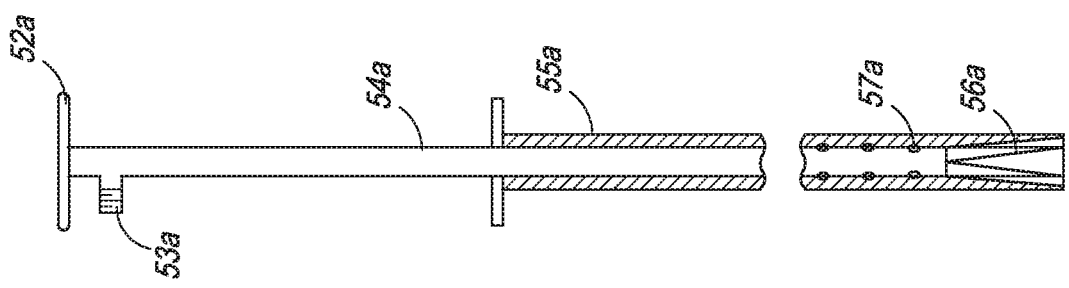
FIG. 5E illustrates the ablation device with a disc shaped positioning element, in accordance with an embodiment of the present invention.

FIG. 5C shows a completely deployed positioning device 56c. The infusion ports 57c are out of the sheath 55c. The length '1' of the catheter 54c that contains the infusion ports 57c and the diameter 'd' of the positioning element 56c are predetermined/known and are used to calculate the amount of thermal energy needed. FIG. 5D illustrates a conical design of the positioning element. The positioning element 56d is conical with a known length '1' and diameter 'd' that is used to calculate the amount of thermal energy needed for ablation. FIG. 5E illustrates a disc shaped design of the positioning element 56e comprising circumferential rings 59e. The circumferential rings 59e are provided at a fixed predetermined distance from the catheter 54e and are used to estimate the diameter of a hollow organ or hollow passage in a patient's body.

Figure 6:
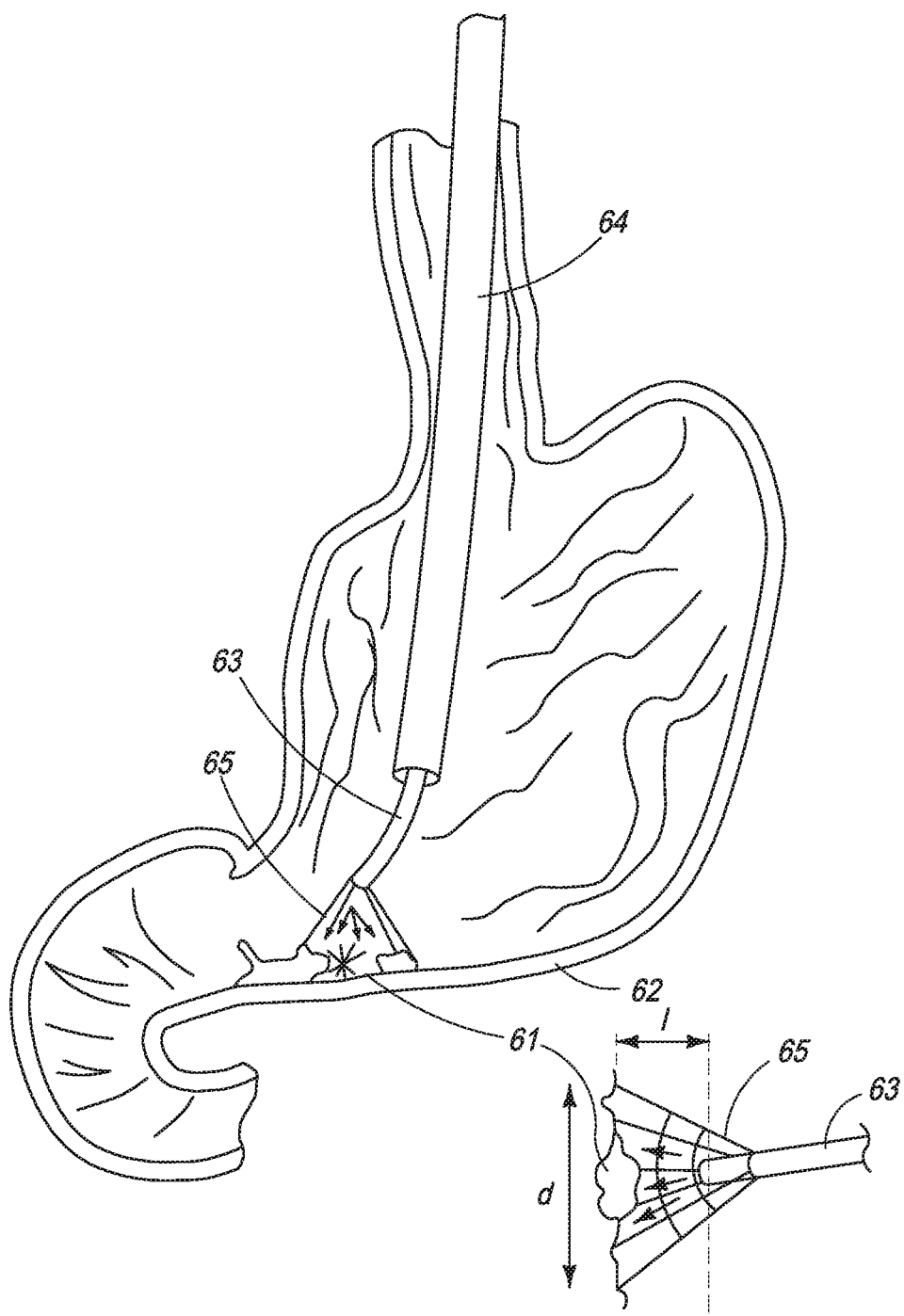
FIG. 6 illustrates an upper gastrointestinal tract with a bleeding vascular lesion being treated by the ablation device, in accordance with an embodiment of the present invention.

FIG. 6 illustrates an upper gastrointestinal tract with a bleeding vascular lesion being treated by the ablation device, in accordance with an embodiment of the present invention. The vascular lesion is a visible vessel 61 in the base of an ulcer 62. The ablation catheter 63 is passed through the channel of an endoscope 64. The conical positioning element 65 is placed over the visible vessel 61. The conical positioning element 65 has a known length '1' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length '1' is greater than 0.1 mm, preferably between 5 and 10 mm. In one embodiment, diameter 'd' depends on the size of the lesion and can be between 1 mm and 10 cm, preferably 1 to 5 cm.

Figure 7:
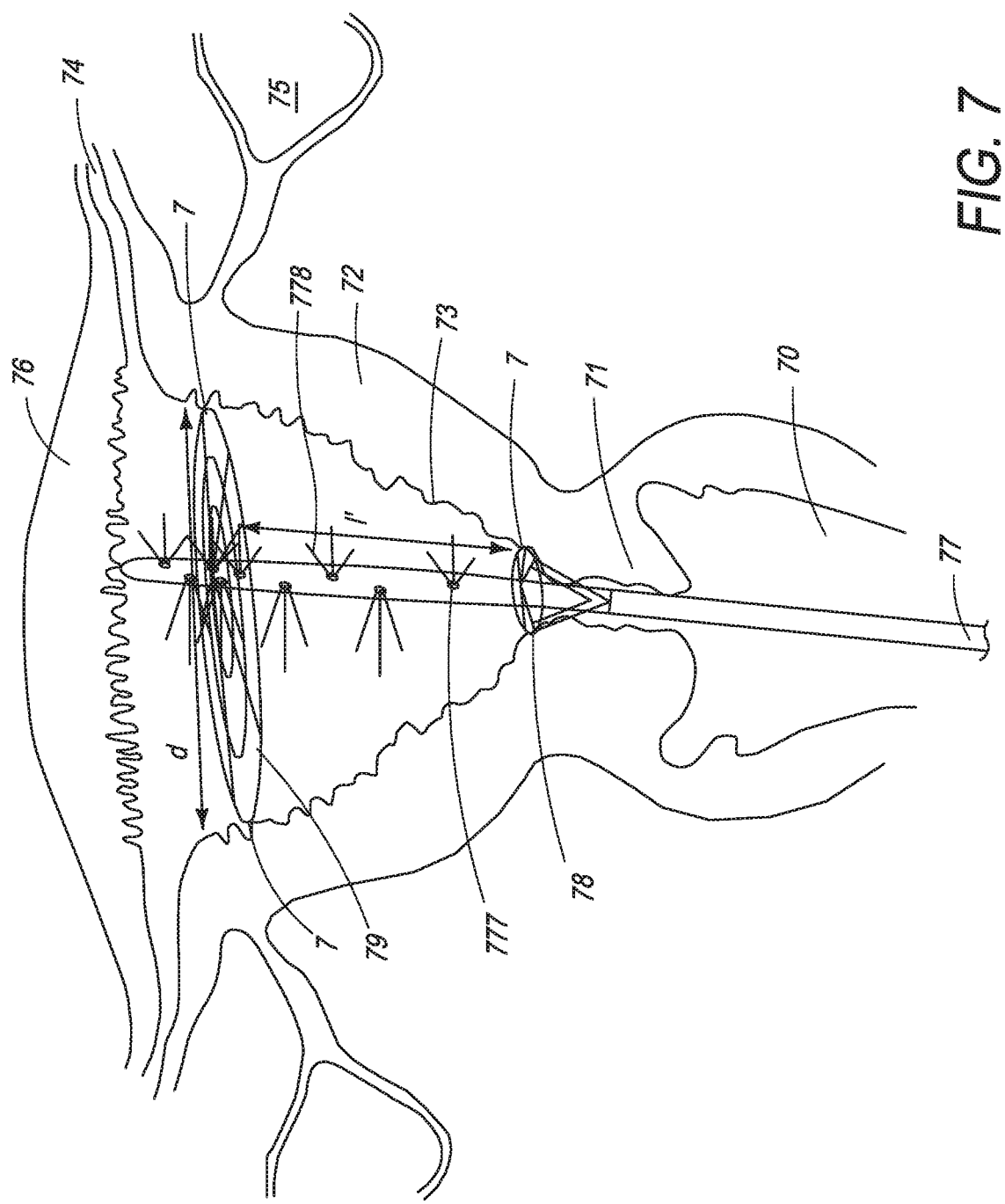
FIG. 7 illustrates endometrial ablation being performed in a female uterus by using the ablation device, in accordance with an embodiment of the present invention.

FIG. 7 illustrates endometrial ablation being performed in a female uterus by using the ablation device, in accordance with an embodiment of the present invention. A cross-section of the female genital tract comprising a vagina 70, a cervix 71, a uterus 72, an endometrium 73, fallopian tubes 74, ovaries 75 and the fundus of the uterus 76 is illustrated. A catheter 77 of the ablation device is inserted into the uterus 72 through the cervix 71. In an embodiment, the catheter 77 has two positioning elements, a conical positioning element 78 and a disc shaped positioning element 79. The positioning element 78 is conical with an insulated membrane covering the conical positioning element 78. The conical element 78 positions the catheter 77 in the center of the cervix 71 and the insulated membrane prevents the escape of thermal energy or ablative agent through the cervix 71. The second disc shaped positioning element 79 is deployed close to the fundus of the uterus 76 positioning the catheter 77 in the middle of the cavity. An ablative agent 778 is passed through infusion ports 777 for uniform delivery of the ablative agent 778 into the uterine cavity. Predetermined length "1" of the ablative segment of the catheter and diameter 'd' of the positioning element 79 allows for estimation of the cavity size and is used to calculate the amount of thermal energy needed to ablate the endometrial lining. Optional temperature sensors 7 deployed close to the endometrial surface are used to control the delivery of the ablative agent 778. Optional topographic mapping using multiple infrared, electromagnetic, acoustic or radiofrequency energy emitters and sensors can be used to define cavity size and shape in patients with an irregular or deformed uterine cavity due to conditions such as fibroids. Additionally data from diagnostic testing can be used to ascertain the uterine cavity size, shape or other characteristics.

In an embodiment, the ablative agent is vapor or steam which contracts on cooling. Steam turns to water which has a lower volume as compared to a cryogen that will expand or a hot fluid used in hydrothermal ablation whose volume stays constant. With both cryogens and hot fluids, increasing energy delivery is associated with increasing volume of the ablative agent which, in turn, requires mechanisms for removing the agent, otherwise the medical provider will run into complications, such as perforation. However, steam, on cooling, turns into water which occupies significantly less volume; therefore, increasing energy delivery is not associated with an increase in volume of the residual ablative agent, thereby eliminating the need for continued removal. This further decreases the risk of leakage of the thermal energy via the fallopian tubes 74 or the cervix 71, thus reducing any risk of thermal injury to adjacent healthy tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area. For endometrial ablation, 100% of the tissue does not need to be ablated to achieve the desired therapeutic effect.

In one embodiment, the preferred distal positioning attachment is an uncovered wire mesh that is positioned proximate to the mid body region. In one embodiment, the preferred proximal positioning device is a covered wire mesh that is pulled into the cervix, centers the device, and occludes the cervix. One or more such positioning devices may be helpful to compensate for the anatomical variations in the uterus. The proximal positioning device is preferably oval, with a long axis between 0.1 mm and 10 cm (preferably 1 cm to 5 cm) and a short axis between 0.1 mm and 5 cm (preferably 0.5 cm to 1 cm). The distal positioning device is preferably circular with a diameter between 0.1 mm and 10 cm, preferably 1 cm to 5 cm.

Figure 8:
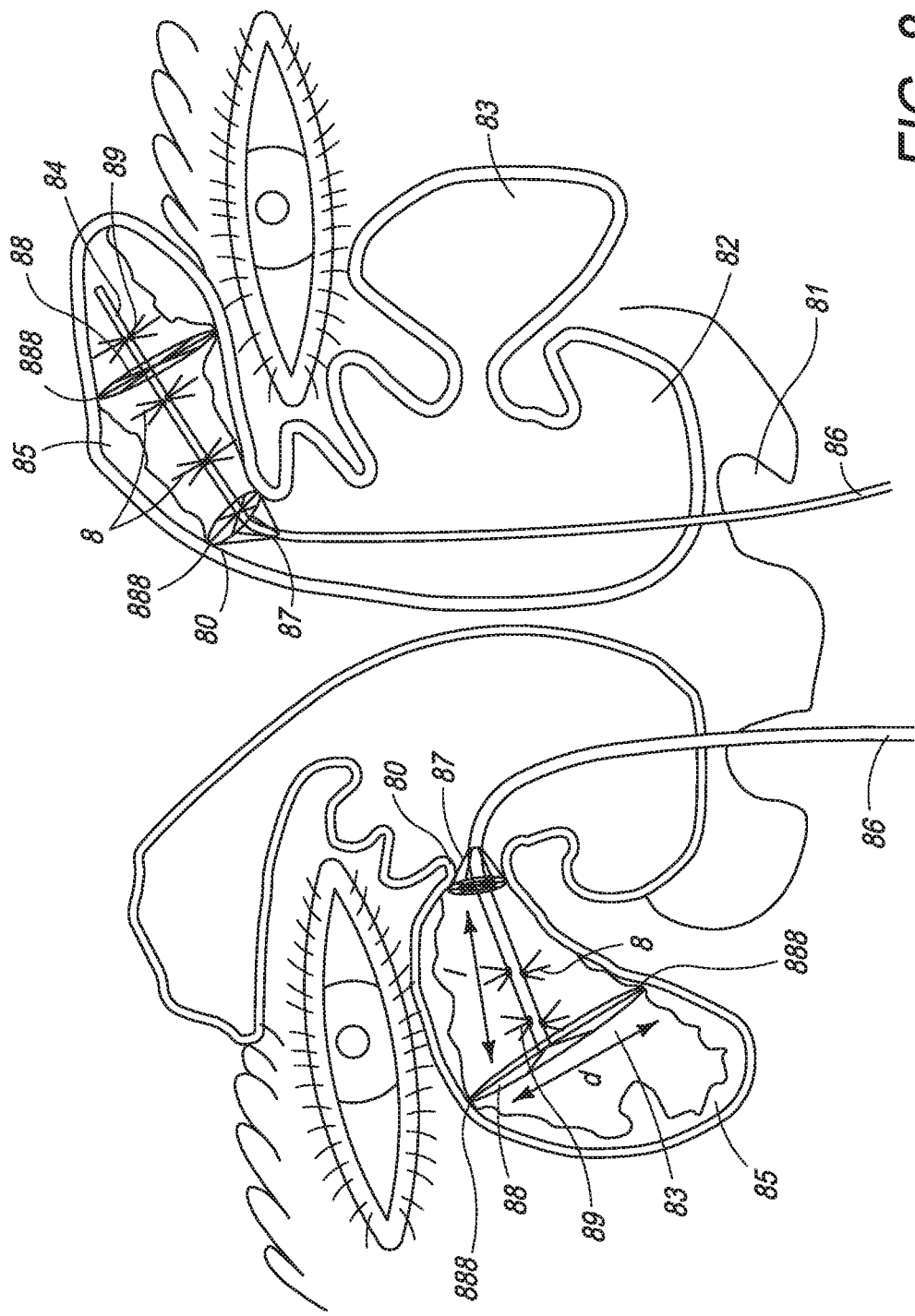
FIG. 8 illustrates sinus ablation being performed in a nasal passage by using the ablation device, in accordance with an embodiment of the present invention.

FIG. 8 illustrates sinus ablation being performed in a nasal passage by using the ablation device, in accordance with an embodiment of the present invention. A cross-section of the nasal passage and sinuses comprising nares 81, nasal passages 82, frontal sinus 83, ethmoid sinus 84, and diseased sinus epithelium 85 is illustrated. The catheter 86 is inserted into the frontal sinus 83 or the ethmoid sinus 84 through the nares 81 and nasal passages 82.

In an embodiment, the catheter 86 has two positioning elements, a conical positioning element 87 and a disc shaped positioning element 88. The positioning element 87 is conical and has an insulated membrane covering. The conical element 87 positions the catheter 86 in the center of the sinus opening 80 and the insulated membrane prevents the escape of thermal energy or ablative agent through the opening. The second disc shaped positioning element 88 is deployed in the frontal sinus cavity 83 or ethmoid sinus cavity 84, positioning the catheter 86 in the middle of either sinus cavity. The ablative agent 8 is passed through the infusion port 89 for uniform delivery of the ablative agent 8 into the sinus cavity. The predetermined length "l" of the ablative segment of the catheter and diameter 'd' of the positioning element 88 allows for estimation of the sinus cavity size and is used to calculate the amount of thermal energy needed to ablate the diseased sinus epithelium 85. Optional temperature sensors 888 are deployed close to the diseased sinus epithelium 85 to control the delivery of the ablative agent 8. In an embodiment, the ablative agent 8 is steam which contracts on cooling. This further decreases the risk of leakage of the thermal energy thus reducing any risk of thermal injury to adjacent healthy tissue. In one embodiment, the dimensional ranges of the positioning elements are similar to those in the endometrial application, with preferred maximum ranges being half thereof. Optional topographic mapping using multiple infrared, electromagnetic, acoustic or radiofrequency energy emitters and sensors can be used to define cavity size and shape in patients with an irregular or deformed nasal cavity due to conditions such as nasal polyps.

Figure 9:
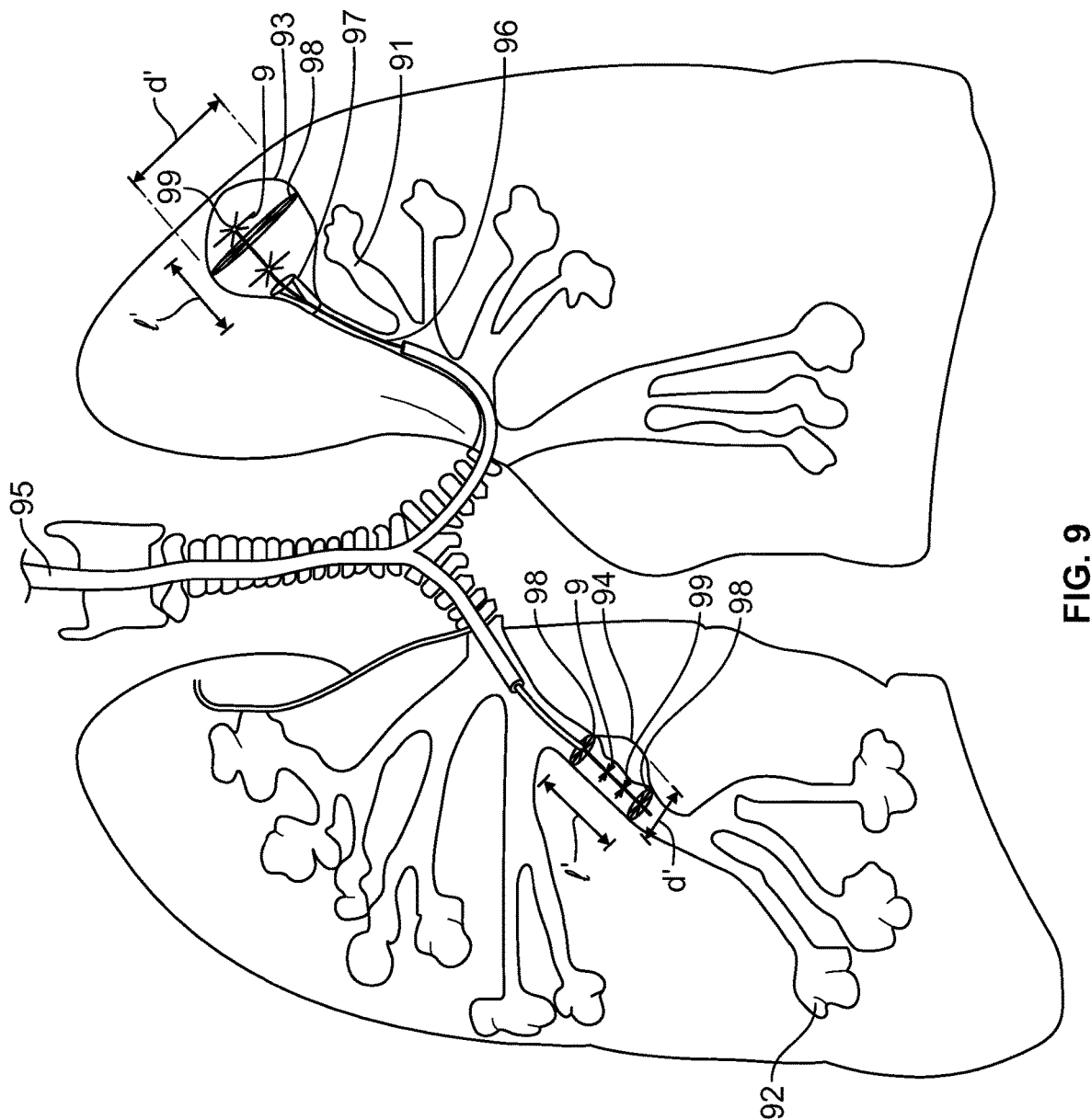
FIG. 9 illustrates bronchial and bullous ablation being performed in a pulmonary system by using the ablation device, in accordance with an embodiment of the present invention.

FIG. 9 illustrates bronchial and bullous ablation being performed in a pulmonary system by using the ablation device, in accordance with an embodiment of the present invention. A cross-section of the pulmonary system comprising bronchus 91, normal alveolus 92, bullous lesion 93, and a bronchial neoplasm 94 is illustrated.

In one embodiment, the catheter 96 is inserted through the channel of a bronchoscope 95 into the bronchus 91 and advanced into a bullous lesion 93. The catheter 96 has two positioning elements, a conical positioning element 97 and a disc shaped positioning element 98. The positioning element 97 is conical having an insulated membrane covering. The conical element 97 positions the catheter 96 in the center of the bronchus 91 and the insulated membrane prevents the escape of thermal energy or ablative agent through the opening into the normal bronchus. The second disc shaped positioning element 98 is deployed in the bullous cavity 93 positioning the catheter 96 in the middle of the bullous cavity 93. An ablative agent 9 is passed through the infusion port 99 for uniform delivery into the sinus cavity. Predetermined length "l" of the ablative segment of the catheter 96 and diameter of the positioning element 98 allow for estimation of the bullous cavity size and is used to calculate the amount of thermal energy needed to ablate the diseased bullous cavity 93. Optionally, the size of the cavity can be calculated from radiological evaluation using a chest CAT scan or MRI. Optional temperature sensors are deployed close to the surface of the bullous cavity 93 to control the delivery of the ablative agent 9. In an embodiment, the ablative agent is steam which contracts on cooling. This further decreases the risk of leakage of the thermal energy into the normal bronchus thus reducing any risk of thermal injury to adjacent normal tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area.

In one embodiment, there are preferably two positioning attachments. In another embodiment, the endoscope is used as one fixation point with one positioning element. The positioning device is between 0.1 mm and 5 cm (preferably 1 mm to 2 cm). The distal positioning device is preferably circular with a diameter between 0.1 mm and 10 cm, preferably 1 cm to 5 cm.

In another embodiment for the ablation of a bronchial neoplasm 94, the catheter 96 is inserted through the channel of a bronchoscope 95 into the bronchus 91 and advanced across the bronchial neoplasm 94. The positioning element 98 is disc shaped having an insulated membrane covering. The positioning element 98 positions the catheter in the center of the bronchus 91 and the insulated membrane prevents the escape of thermal energy or ablative agent through the opening into the normal bronchus. The ablative agent 9 is passed through the infusion port 99 in a non-circumferential pattern for uniform delivery of the ablative agent to the bronchial neoplasm 94. The predetermined length "l" of the ablative segment of the catheter and diameter 'd' of the positioning element 98 are used to calculate the amount of thermal energy needed to ablate the bronchial neoplasm 94.

The catheter could be advanced to the desired location of ablation using endoscopic, laparoscopic, stereotactic or radiological guidance. Optionally the catheter could be advanced to the desired location using magnetic navigation.

Figure 10:
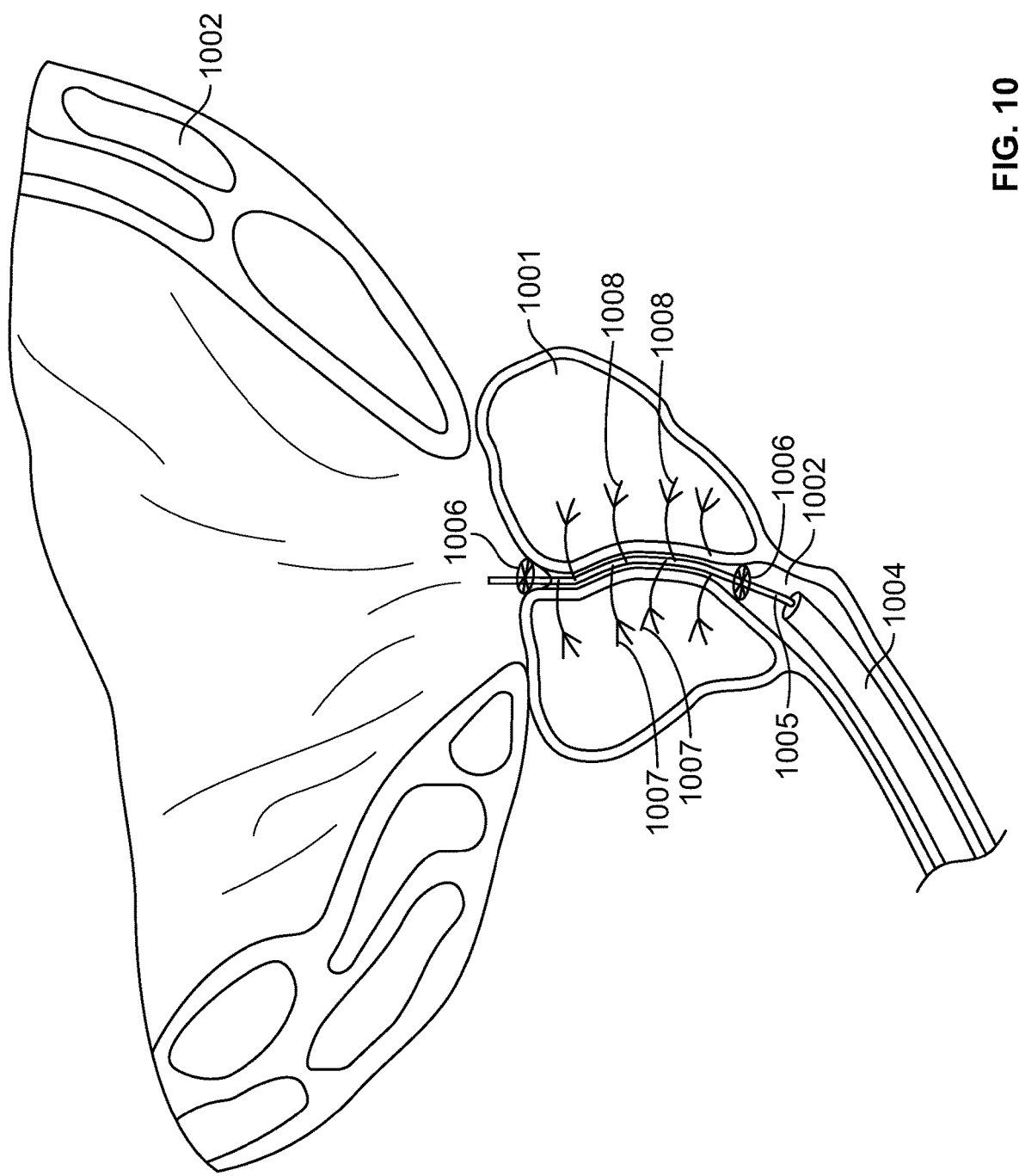
FIG. 10 illustrates prostate ablation being performed on an enlarged prostrate in a male urinary system by using the device, in accordance with an embodiment of the present invention.

FIG. 10 illustrates prostate ablation being performed on an enlarged prostrate in a male urinary system by using the device, in accordance with an embodiment of the present invention. A cross-section of a male genitourinary tract having an enlarged prostate 1001, bladder 1002, and urethra 1003 is illustrated. The urethra 1003 is compressed by the enlarged prostate 1001. The ablation catheter 1005 is passed through the cystoscope 1004 positioned in the urethra 1003 distal to the obstruction. The positioning elements 1006 are deployed to center the catheter in the urethra 1003 and one or more insulated needles 1007 are passed to pierce the prostate 1001. The vapor ablative agent 1008 is passed through the insulated needles 1007 thus causing ablation of the diseased prostatic tissue resulting in shrinkage of the prostate.

The size of the enlarged prostate could be calculated by using the differential between the extra-prostatic and intra-prostatic urethra. Normative values could be used as baseline. Additional ports for infusion of a cooling fluid into the urethra can be provided to prevent damage to the urethra while the ablative energy is being delivered to the prostrate for ablation, thus preventing complications such as stricture formation.

In one embodiment, the positioning attachment must be separated from the ablation region by a distance of greater than 0.1 mm, preferably 1 mm to 5 mm and no more than 2 cm. In another embodiment, the positioning attachment can be deployed in the bladder and pulled back into the urethral opening/neck of the bladder thus fixing the catheter. In one embodiment, the positioning device is between 0.1 mm and 10 cm in diameter.

Figure 11:
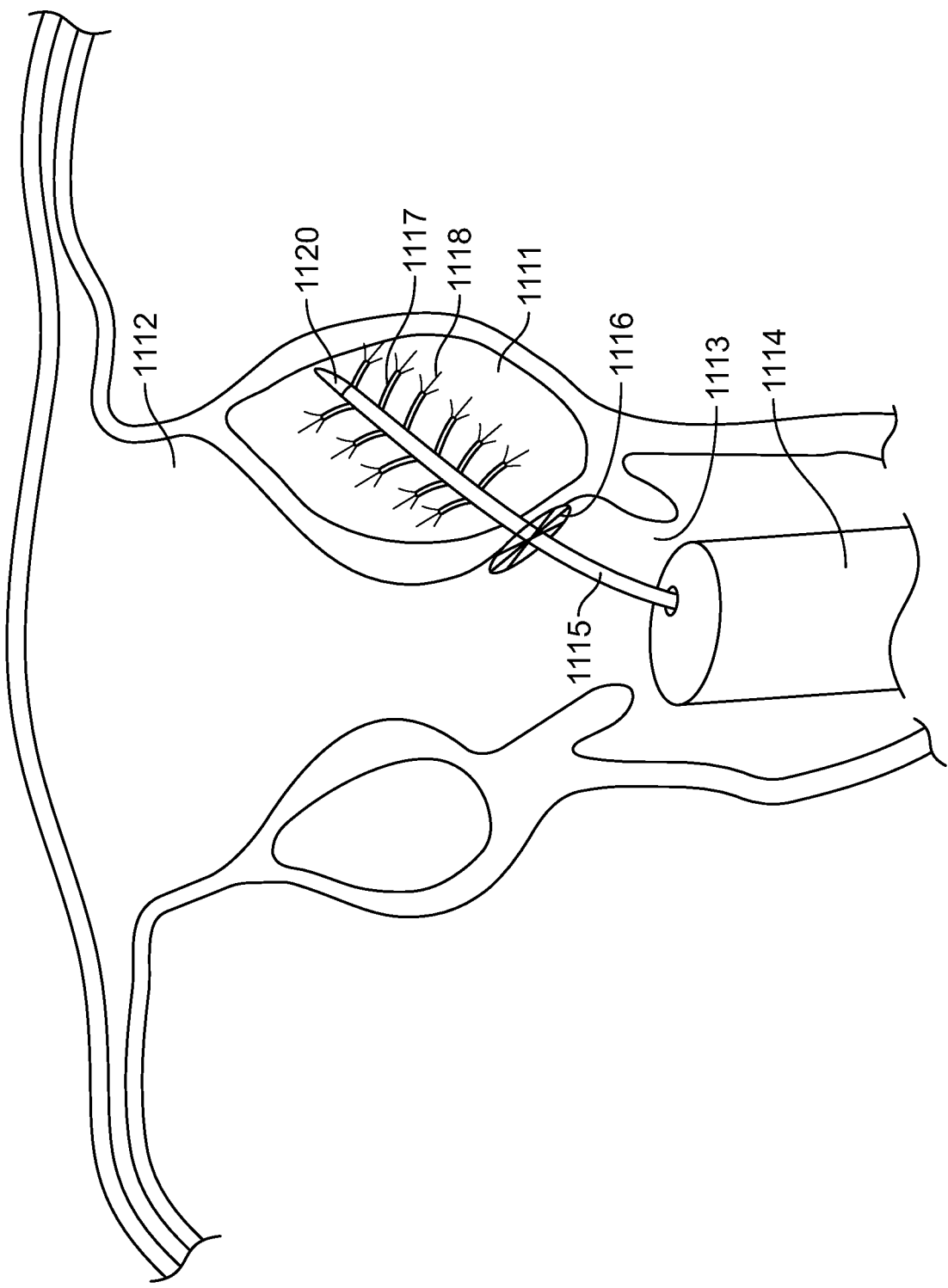
FIG. 11 illustrates fibroid ablation being performed in a female uterus by using the ablation device, in accordance with an embodiment of the present invention.

FIG. 11 illustrates fibroid ablation being performed in a female uterus by using the ablation device, in accordance with an embodiment of the present invention. A cross-section of a female genitourinary tract comprising a uterine fibroid 1111, uterus 1112, and cervix 1113 is illustrated. The ablation catheter 1115 is passed through the hysteroscope 1114 positioned in the uterus distal to the fibroid 1111. The ablation catheter 1115 has a puncturing tip 1120 that helps puncture into the fibroid 1111. The positioning elements 1116 are deployed to center the catheter in the fibroid and insulated needles 1117 are passed to pierce the fibroid tissue 1111. The vapor ablative agent 1118 is passed through the needles 1117 thus causing ablation of the uterine fibroid 1111 resulting in shrinkage of the fibroid.

Figure 12:
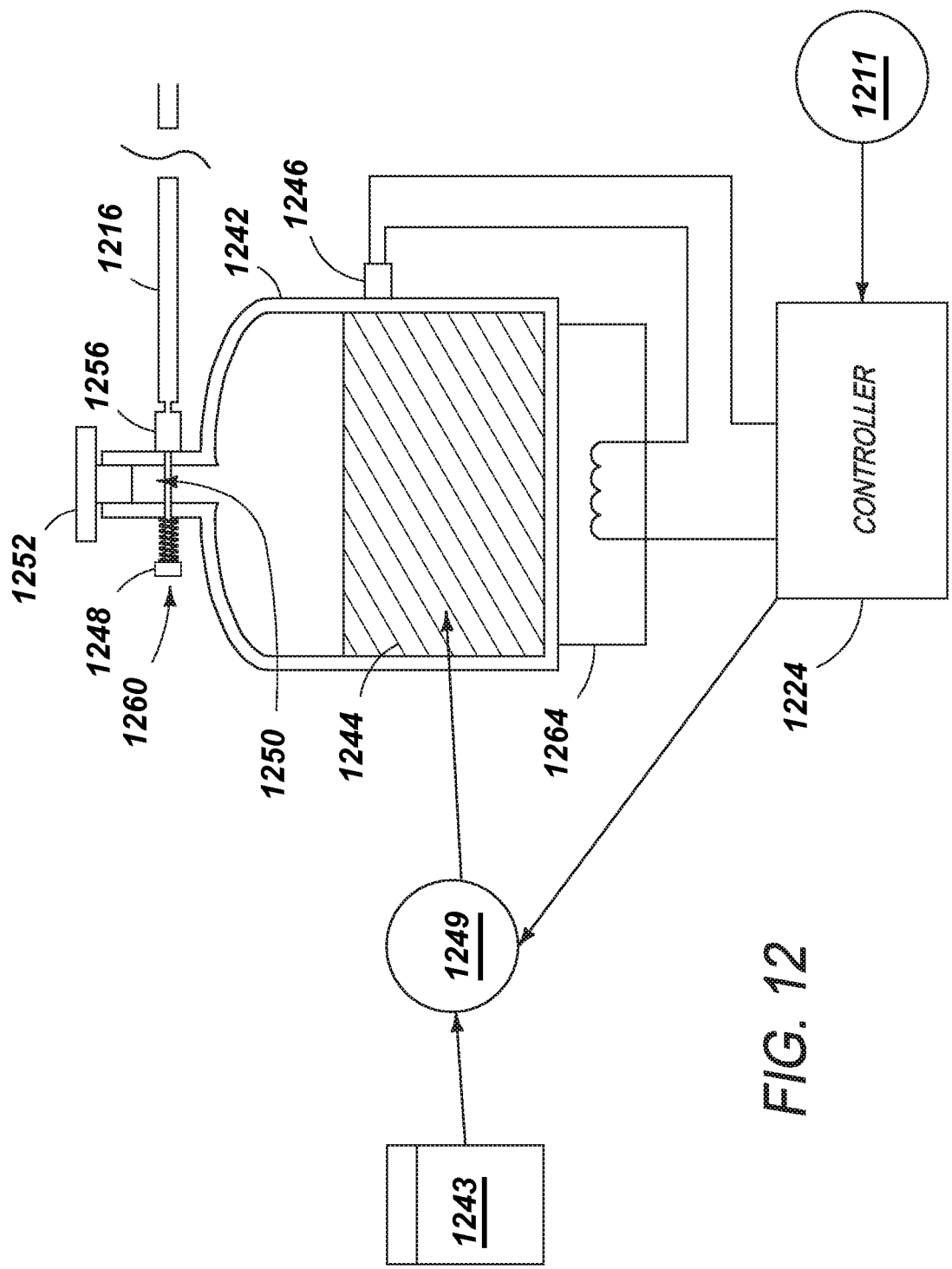
FIG. 12 illustrates a vapor delivery system using an RF heater for supplying vapor to the ablation device, in accordance with an embodiment of the present invention.

FIG. 12 illustrates a vapor delivery system using an RF heater for supplying vapor to the ablation device, in accordance with an embodiment of the present invention. In an embodiment, the vapor is used as an ablative agent in conjunction with the ablation device described in the present specification. RF heater 1264 is located proximate a pressure vessel 1242 containing a liquid 1244. RF heater 1264 heats vessel 1242, in turn heating the liquid 1244. The liquid 1244 heats up and begins to evaporate causing an increase in pressure inside the vessel 1242. The pressure inside vessel 1242 can be kept fairly constant by providing a thermal switch 1246 that controls resistive heater 1264. Once the temperature of the liquid 1244 reaches a predetermined temperature, the thermal switch 1246 shuts off RF heater 1264. The vapor created in pressure vessel 1242 may be released via a control valve 1250. As the vapor exits vessel 1242, a pressure drop is created in the vessel resulting in a reduction in temperature. The reduction of temperature is measured by thermal switch 1246, and RF heater 1264 is turned back on to heat liquid 1244. In one embodiment, the target temperature of vessel 1242 may be set to approximately 108° C., providing a continuous supply of vapor. As the vapor is released, it undergoes a pressure drop, which reduces the temperature of the vapor to a range of approximately 90-100° C. As liquid 1244 in vessel 1242 evaporates and the vapor exits vessel 1242, the amount of liquid 1244 slowly diminishes. The vessel 1242 is optionally connected to reservoir 1243 containing liquid 1244 via a pump 1249 which can be turned on by the controller 1224 upon sensing a fall in pressure or temperature in vessel 1242, delivering additional liquid 1244 to the vessel 1242.

Vapor delivery catheter 1216 is connected to vessel 1242 via a fluid connector 1256. When control valve 1250 is open, vessel 1242 is in fluid communication with delivery catheter 1216 via connector 1256. Control switch 1260 may serve to turn vapor delivery on and off via actuator 1248. For example, control switch 1260 may physically open and close the valve 1250, via actuator 1248, to control delivery of vapor stream from the vessel 1242. Switch 1260 may be configured to control other attributes of the vapor such as direction, flow, pressure, volume, spray diameter, or other parameters.

Instead of, or in addition to, physically controlling attributes of the vapor, switch 1260 may electrically communicate with a controller 1224. Controller 1224 controls the RF heater 1264, which in turn controls attributes of the vapor, in response to actuation of switch 1260 by the operator. In addition, controller 1224 may control valves temperature or pressure regulators associated with catheter 1216 or vessel 1242. A flow meter 1252 may be used to measure the flow, pressure, or volume of vapor delivery via the catheter 1216. The controller 1224 controls the temperature and pressure in the vessel 1242 and the time, rate, flow, and volume of vapor flow through the control valve 1250. These parameters are set by the operator 1211. The pressure created in vessel 1242, using the target temperature of 108° C., may be in the order of 25 pounds per square inch (psi) (1.72 bars).

Figure 13:
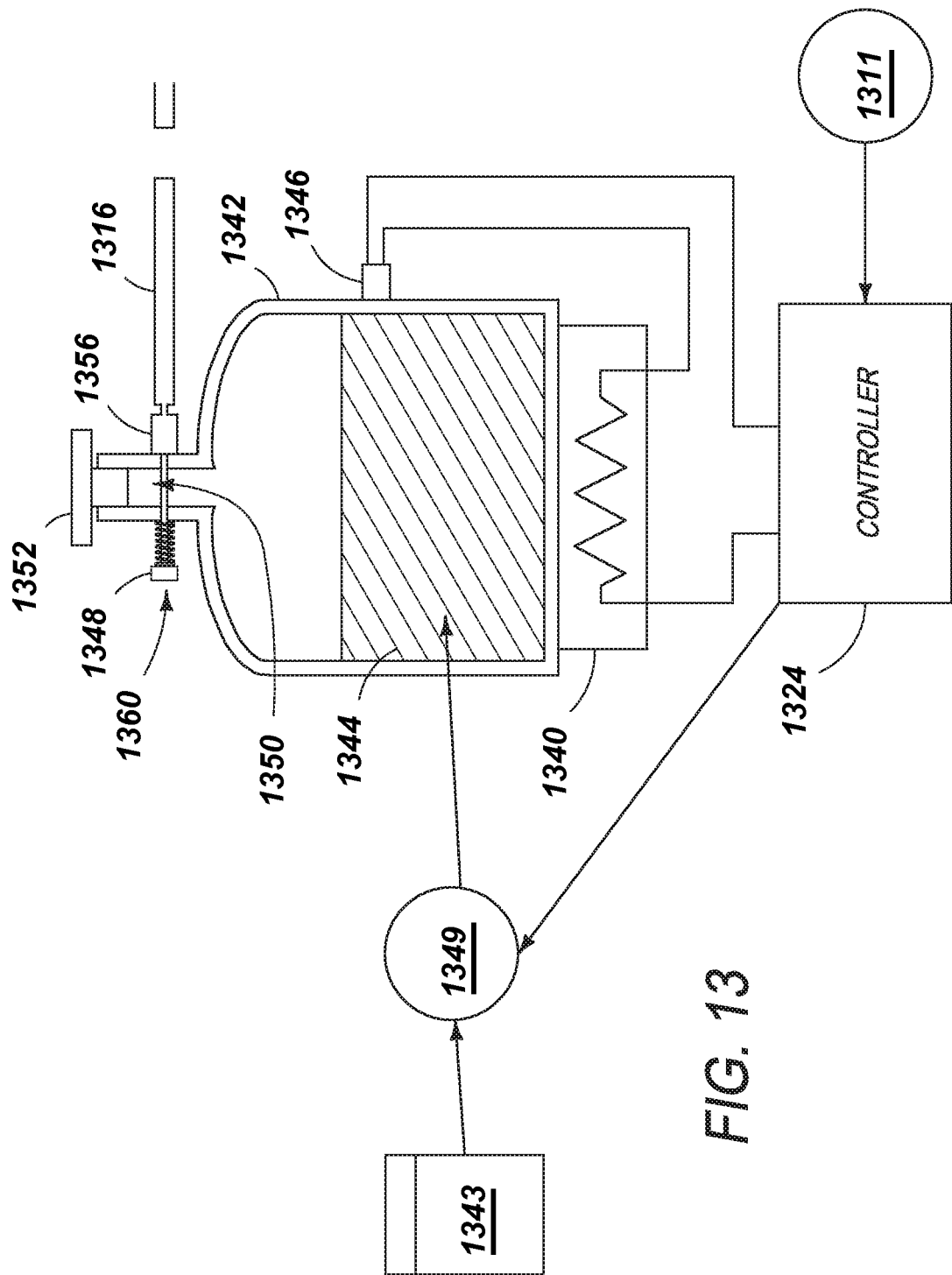
FIG. 13 illustrates a vapor delivery system using a resistive heater for supplying vapor to the ablation device, in accordance with an embodiment of the present invention.

FIG. 13 illustrates a vapor delivery system using a resistive heater for supplying vapor to the ablation device, in accordance with an embodiment of the present invention. In an embodiment, the generated vapor is used as an ablative agent in conjunction with the ablation device described in the present specification. Resistive heater 1340 is located proximate a pressure vessel 1342. Vessel 1342 contains a liquid 1344. Resistive heater 1340 heats vessel 1342, in turn heating liquid 1344. Accordingly, liquid 1344 heats and begins to evaporate. As liquid 1344 begins to evaporate, the vapor inside vessel 1342 causes an increase in pressure in the vessel. The pressure in vessel 1342 can be kept fairly constant by providing a thermal switch 1346 that controls resistive heater 1340. When the temperature of liquid 1344 reaches a predetermined temperature, thermal switch 1346 shuts off resistive heater 1340. The vapor created in pressure vessel 1342 may be released via a control valve 1350. As the vapor exits vessel 1342, vessel 1342 experiences a pressure drop. The pressure drop of vessel 1342 results in a reduction of temperature. The reduction of temperature is measured by thermal switch 1346, and resistive heater 1340 is turned back on to heat liquid 1344. In one embodiment, the target temperature of vessel 1342 may be set to approximately 108° C., providing a continuous supply of vapor. As the vapor is released, it undergoes a pressure drop, which reduces the temperature of the vapor to a range of approximately 90-100° C. As liquid 1344 in vessel 1342 evaporates and the vapor exits vessel 1342, the amount of liquid 1344 slowly diminishes. The vessel 1342 is connected to another vessel 1343 containing liquid 1344 via a pump 1349 which can be turned on by the controller 1324 upon sensing a fall in pressure or temperature in vessel 1342 delivering additional liquid 1344 to the vessel 1342.

Vapor delivery catheter 1316 is connected to vessel 1342 via a fluid connector 1356. When control valve 1350 is open, vessel 1342 is in fluid communication with delivery catheter 1316 via connector 1356. Control switch 1360 may serve to turn vapor delivery on and off via actuator 1348. For example, control switch 1360 may physically open and close the valve 1350, via actuator 1348, to control delivery of vapor stream from the vessel 1342. Switch 1360 may be configured to control other attributes of the vapor such as direction, flow, pressure, volume, spray diameter, or other parameters. Instead of, or in addition to, physically controlling attributes of the vapor, switch 1360 may electrically communicate with a controller 1324. Controller 1324 controls the resistive heater 1340, which in turn controls attributes of the vapor, in response to actuation of switch 1360 by the operator. In addition, controller 1324 may control valves temperature or pressure regulators associated with catheter 16 or vessel 1342. A flow meter 1352 may be used to measure the flow, pressure, or volume of vapor delivery via the catheter 1316. The controller 1324 controls the temperature and pressure in the vessel 1342 as well as time, rate, flow, and volume of vapor flow through the control valve 1350. These parameters are set by the operator 1311. The pressure created in vessel 1342, using the target temperature of 108° C., may be on the order of 25 pounds per square inch (psi) (1.72 bars).

Figure 14:
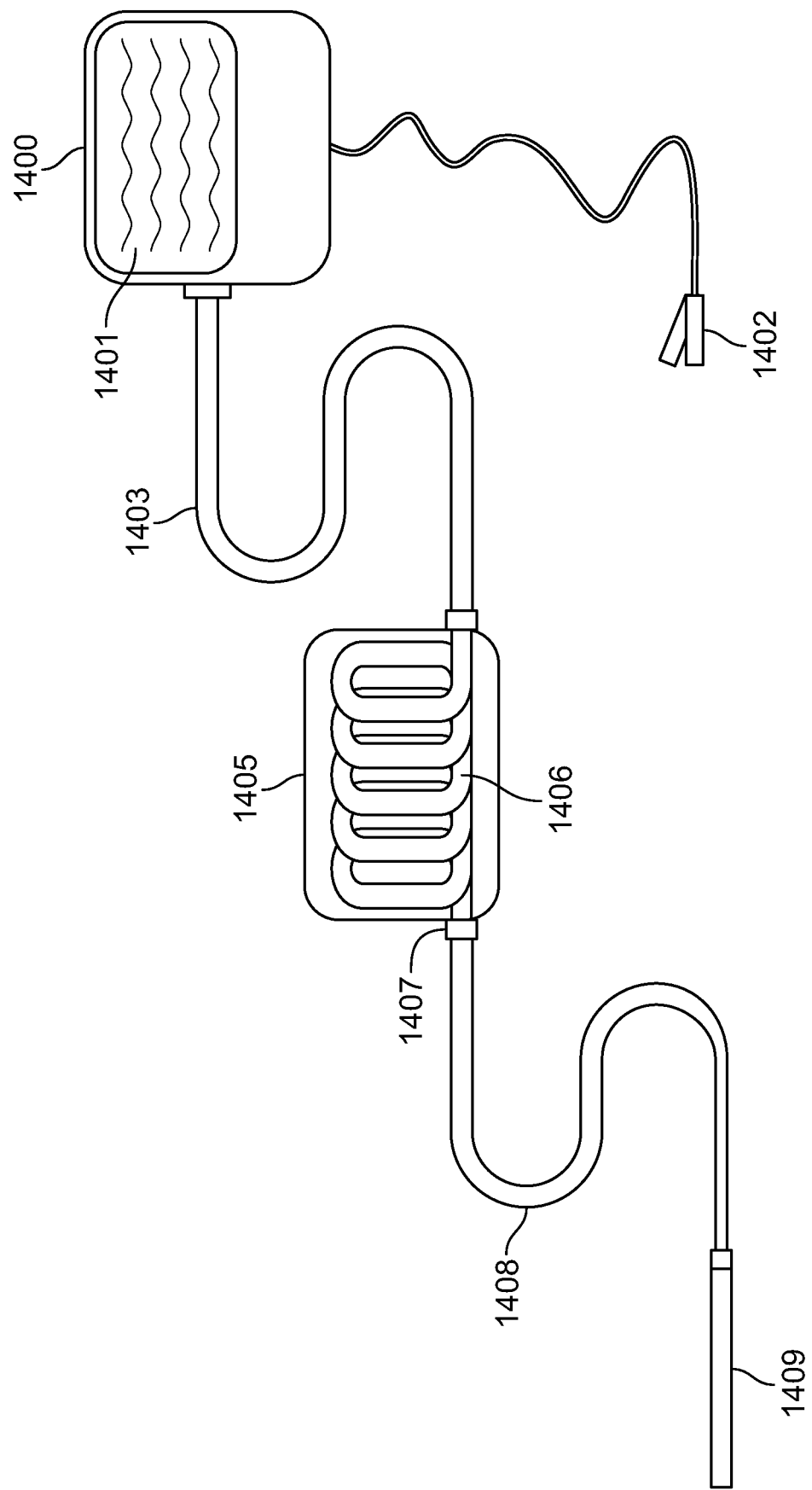
FIG. 14 illustrates a vapor delivery system using a heating coil for supplying vapor to the ablation device, in accordance with an embodiment of the present invention.

FIG. 14 illustrates a vapor delivery system using a heating coil for supplying vapor to the ablation device, in accordance with an embodiment of the present invention. In an embodiment, the generated vapor is used as an ablative agent in conjunction with the ablation device described in the present invention. The vapor delivery system includes a conventional generator 1400 that is commonly used in operating rooms to provide power to specialized tools, i.e., cutters. The generator 1400 is modified to include an integrated liquid reservoir 1401. In one embodiment, the reservoir 1401 is filled with room temperature pure water. The reservoir 1401 portion of the generator 1400 is connected to the heating component 1405 via a reusable active cord 1403. In one embodiment, the reusable active cord 1403 may be used up to 200 times. The cord 1403 is fixedly attached via connections at both ends to withstand operational pressures, and preferably a maximum pressure, such that the cord does not become disconnected. In one embodiment, the connections can resist at least 1 atm of pressure. In one embodiment, the connections are of a luer lock type. The cord 1403 has a lumen through which liquid flows to the heating component 1405. In one embodiment, the heating component 1405 contains a coiled length of tubing 1406. As liquid flows through the coiled tubing 1406, it is heated by the surrounding heating component 1405 in a fashion similar to a conventional heat exchanger. As the liquid is heated, it becomes vaporized. The heating component contains a connector 1407 that accommodates the outlet of vapor from the coiled tubing 1406. One end of a single use cord 1408 attaches to the heating component 1405 at the connector 1407. The connector 1407 is designed to withstand pressures generated by the vapor inside the coiled tubing 1406 during operation. In one embodiment, the connector 1407 is of a luer lock type. An ablation device 1409 is attached to the other end of the single use cord 1408 via a connection able to withstand the pressures generated by the system. In one embodiment, the ablation device is integrated with a catheter. In another embodiment, the ablation device is integrated with a probe. The single use cord 1408 has a specific luminal diameter and is of a specific length to ensure that the contained vapor does not condense into liquid while simultaneously providing the user enough slack to operate. In addition, the single use cord 1408 provides sufficient insulation so that personnel will not suffer burns when coming into contact with the cord. In one embodiment, the single use cord has a luminal diameter of less than 3 mm, preferably less than 2.6 mm, and is longer than 1 meter in length.

In one embodiment, the system includes a foot pedal 1402 by which the user can supply more vapor to the ablation device. Depressing the foot pedal 1402 allows liquid to flow from the reservoir 1401 into the heating component 1405 where it changes into vapor within the coiled tubing 1406. The vapor then flows to the ablation device via the single use tube 1408. The ablation device includes an actuator by which the user can open small ports on the device, releasing the vapor and ablating the target tissue.

Figure 15:
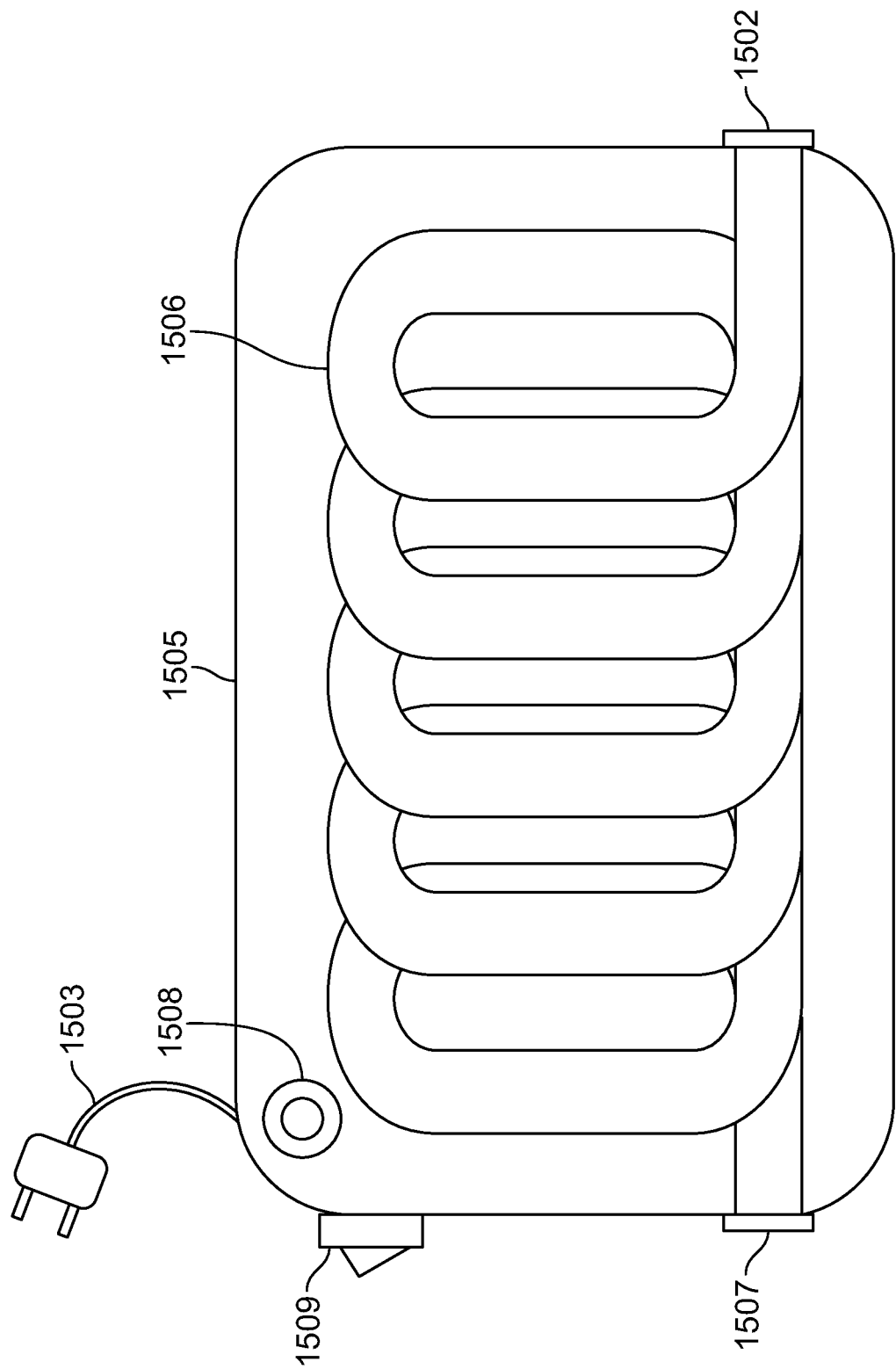
FIG. 15 illustrates the heating component and coiled tubing of the heating coil vapor delivery system of FIG. 14, in accordance with an embodiment of the present invention.

FIG. 15 illustrates the heating component 1505 and coiled tubing 1506 of the heating coil vapor delivery system of FIG. 14, in accordance with an embodiment of the present invention. Liquid arrives through a reusable active cord (not shown) at a connection 1502 on one side of the heating component 1505. The liquid then travels through the coiled tubing 1506 within the heating component 1505. The coiled tubing is composed of a material and configured specifically to provide optimal heat transfer to the liquid. In one embodiment, the coiled tubing 1506 is copper. The temperature of the heating component 1505 is set to a range so that the liquid is converted to vapor as it passes through the coiled tubing 1506. In one embodiment, the temperature of the heating component 1505 can be set by the user through the use of a temperature setting dial 1508. In one embodiment, the heating component contains an on/off switch 1509 and is powered through the use of an attached AC power cord 1503. In another embodiment, the heating component receives power through an electrical connection integrated into and/or facilitated by the active cord connection to the reservoir. The vapor passes through the end of the coiled tubing 1506 and out of the heating component 1505 through a connector 1507. In one embodiment, the connector 1507 is located on the opposite side of the heating component 1505 from the inlet connection 1502. A single use cord (not shown) attaches to the connector 1507 and supplies vapor to the ablation device.

Figure 16A:
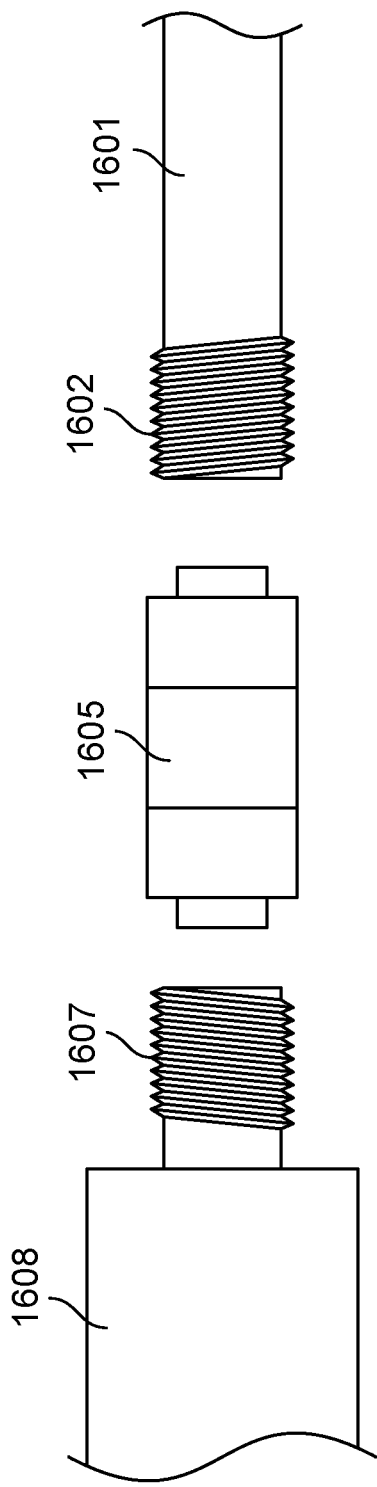
FIG. 16A illustrates the unassembled interface connection between the ablation device and the single use cord of the heating coil vapor delivery system of FIG. 14, in accordance with an embodiment of the present invention.

FIG. 16A illustrates the unassembled interface connection between the ablation device 1608 and the single use cord 1601 of the heating coil vapor delivery system of FIG. 14, in accordance with an embodiment of the present invention. In this embodiment, the ablation device 1608 and single use cord 1601 are connected via a male-to-male double luer lock adapter 1605. The end of the single use cord 1601 is threaded to form a female end 1602 of a luer lock interface and connects to one end of the adapter 1605. The ablation device 1608 includes a small protrusion at its non-operational end which is also threaded to form a female end 1607 of a luer lock interface and connects to the other end of the adapter 1605. The threading luer lock interface provides a secure connection and is able to withstand the pressures generated by the heating coil vapor delivery system without becoming disconnected.

Figure 16B:
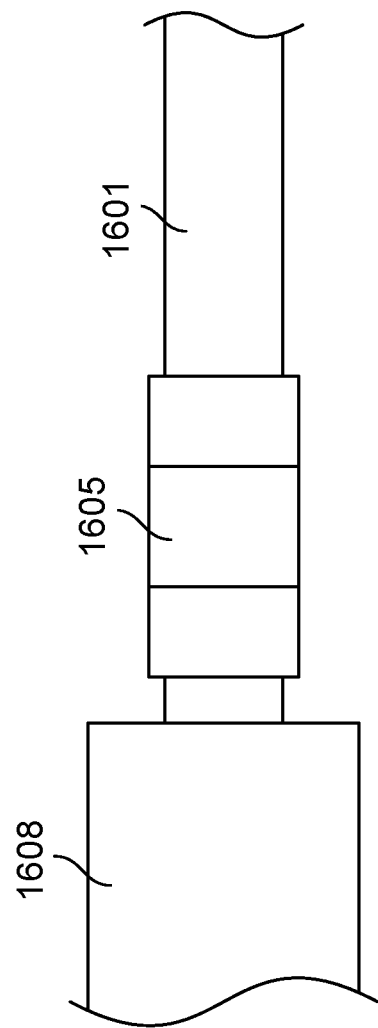
FIG. 16B illustrates the assembled interface connection between the ablation device and the single use cord of the heating coil vapor delivery system of FIG. 14, in accordance with an embodiment of the present invention.

FIG. 16B illustrates the assembled interface connection between the ablation device 1608 and the single use cord 1601 of the heating coil vapor delivery system of FIG. 14, in accordance with an embodiment of the present invention. The male-to-male double luer lock adapter 1605 is pictured securing the two components together. The double luer lock interface provides a stable seal, allows interchangeability between ablation devices, and enables users to quickly replace single use cords.

Figure 17:
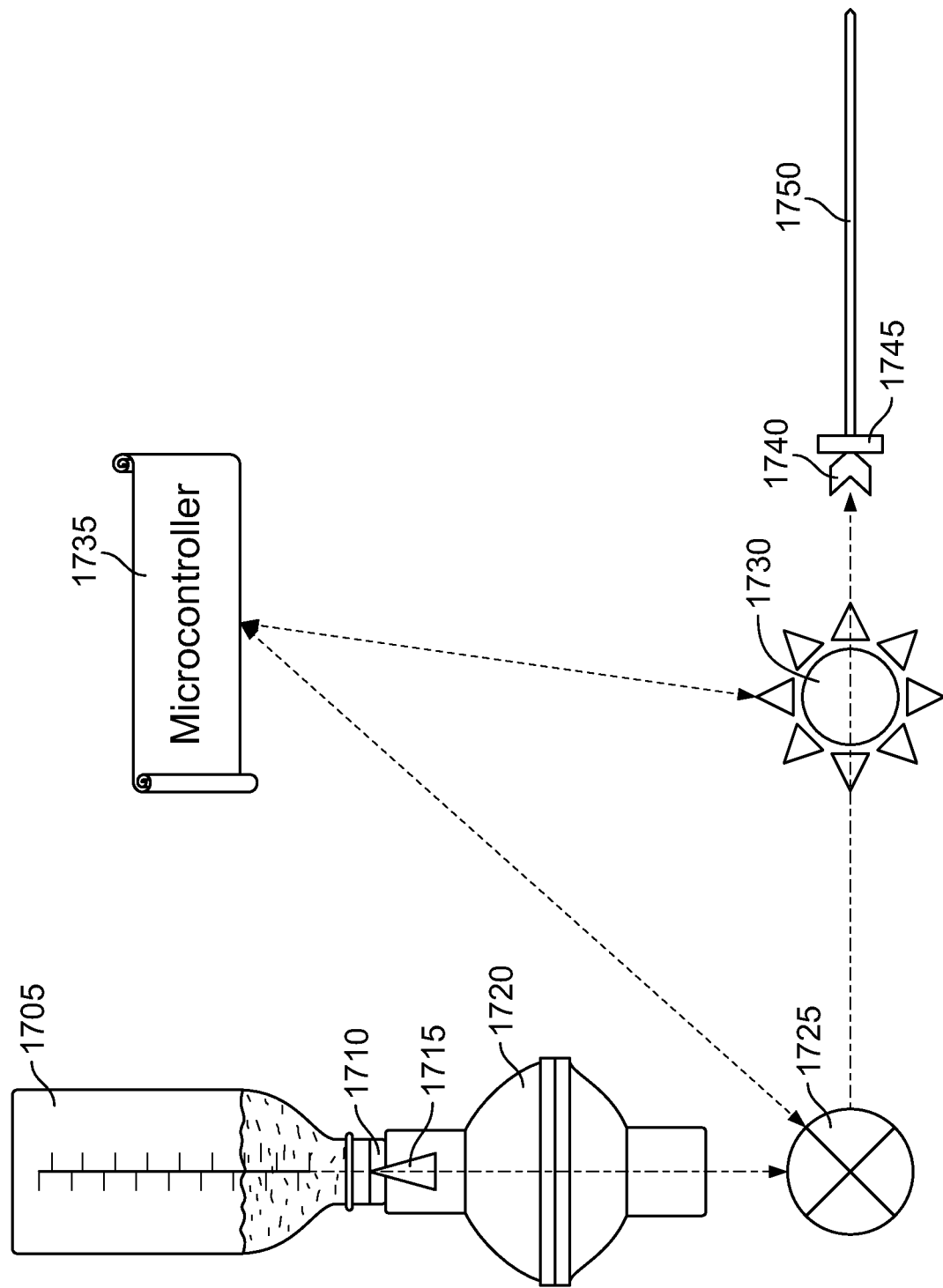
FIG. 17 illustrates a vapor ablation system using a heater or heat exchange unit for supplying vapor to the ablation device, in accordance with another embodiment of the present invention.

FIG. 17 illustrates a vapor ablation system using a heater or heat exchange unit for supplying vapor to the ablation device, in accordance with another embodiment of the present invention. In the pictured embodiment, water for conversion to vapor is supplied in a disposable, single use sterile fluid container 1705. The container 1705 is sealed with a sterile screw top 1710 that is punctured by a needle connector 1715 provided on a first end of a first filter member 1720. The second end of the first filter member 1720, opposite the first end, is connected to a pump 1725 for drawing the water from the fluid container 1705, through the first filter member 1720, and into the heater or heat exchange unit 1730. The system includes a microcontroller or microprocessor 1735 for controlling the actions of the pump 1725 and heater or heat exchange unit 1730. The heater or heat exchange unit 1730 converts the water into vapor (steam). The increase in pressure generated during the heating step drives the vapor through an optional second filter member 1740 and into the ablation catheter 1750. In one embodiment, the heater or heat exchange unit 1730 includes a one-way valve at its proximal end to prevent the passage of vapor back toward the pump 1725. In various embodiments, optional sensors 1745 positioned proximate the distal end of the catheter 1750 measure one or more of temperature, pressure, or flow of vapor and transmit the information to the microcontroller 1735, which in turn controls the rate of the pump 1725 and the level of vaporizing energy provided by the heater or heat exchange unit 1730.

Figure 18:
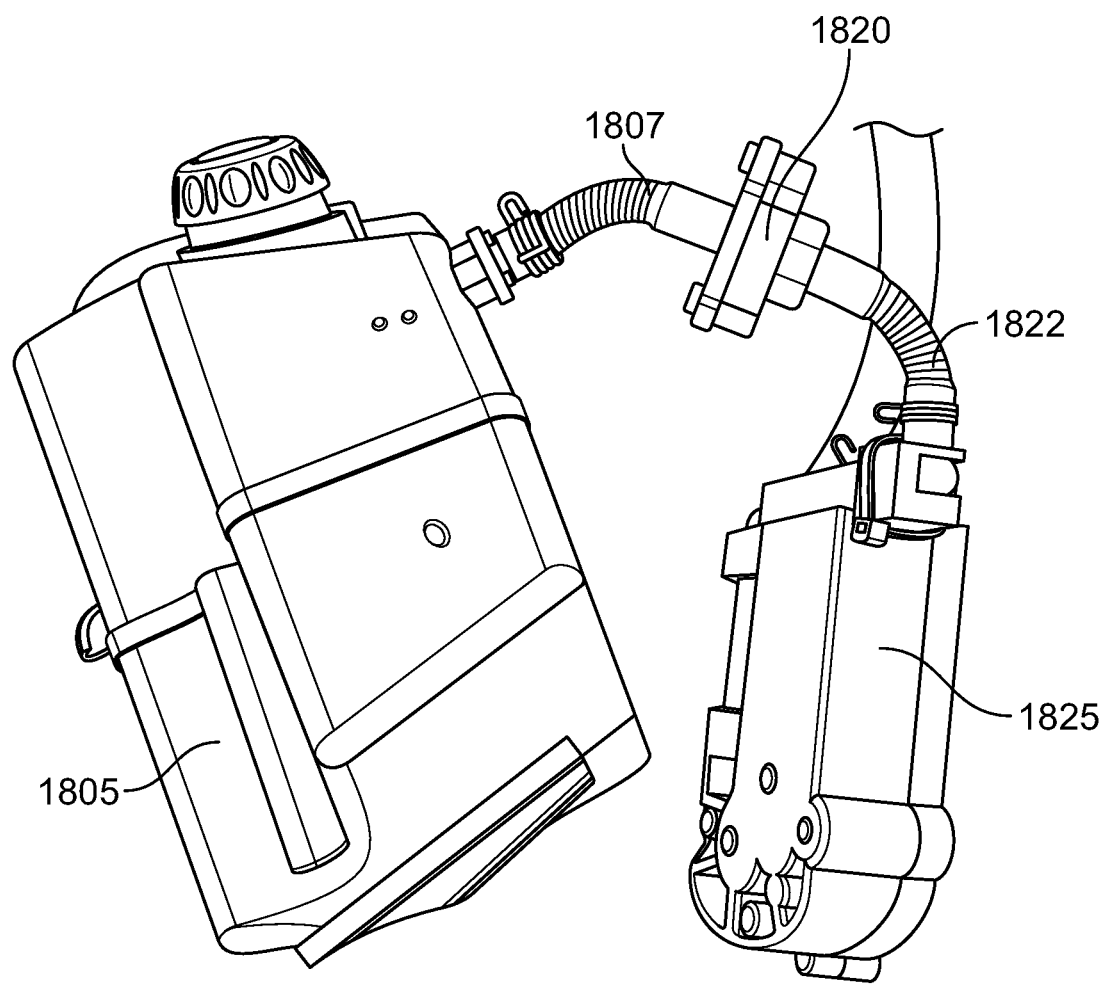
FIG. 18 illustrates the fluid container, filter member, and pump of the vapor ablation system of FIG. 17.

FIG. 18 illustrates the fluid container 1805, first filter member 1820, and pump 1825 of the vapor ablation system of FIG. 17. As can be seen in the pictured embodiment, the system includes a water-filled, disposable, single use sterile fluid container 1805 and a pump 1825 with a first filter member 1820 disposed therebetween. The first filter member 1820 is connected to the container 1805 and pump 1825 by two first and second lengths of sterile tubing 1807, 1822 respectively, and includes a filter for purifying the water used in the ablation system.

Figure 19:
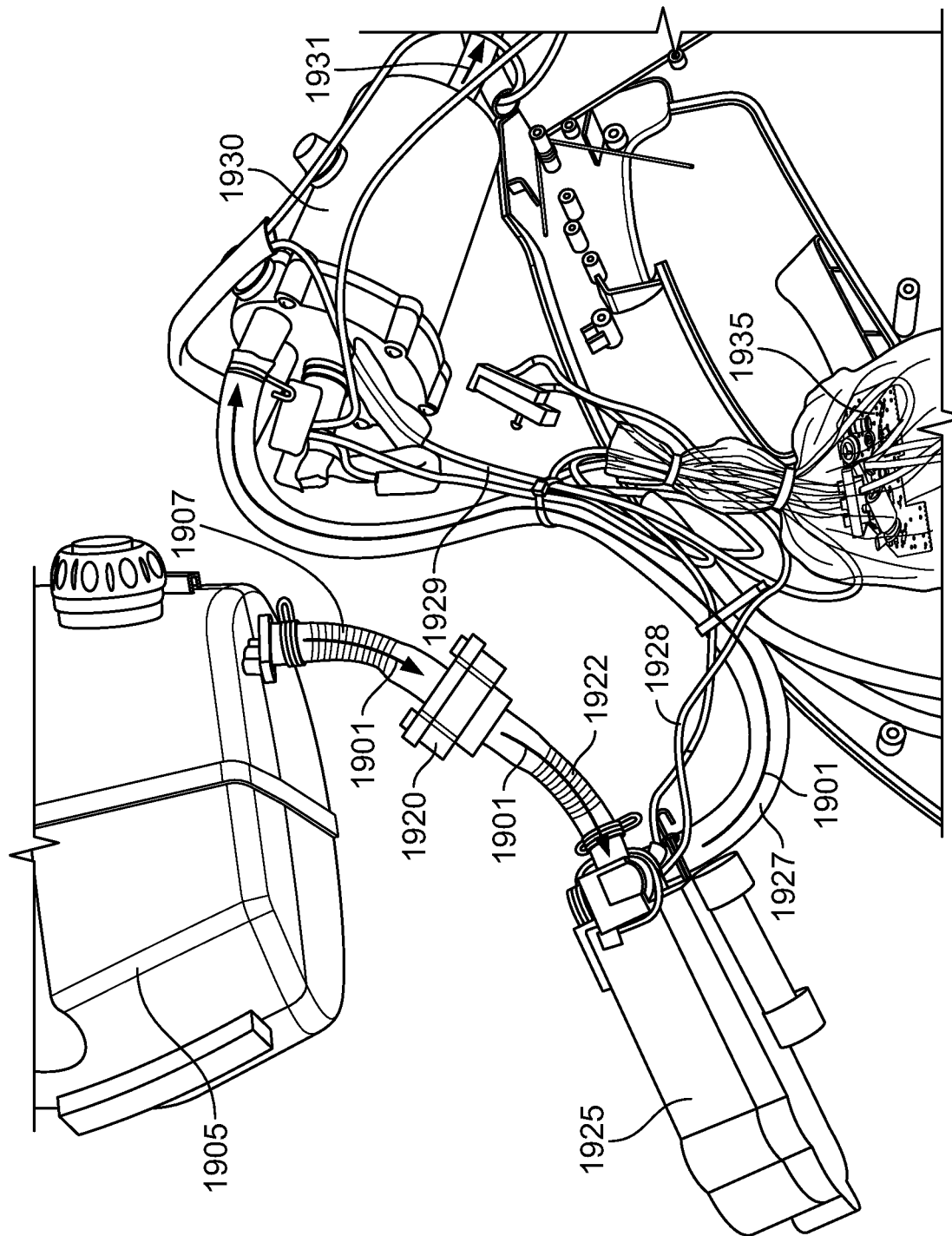
FIG. 19 illustrates a first view of the fluid container, filter member, pump, heater or heat exchange unit, and microcontroller of the vapor ablation system of FIG. 17.
Figure 20:
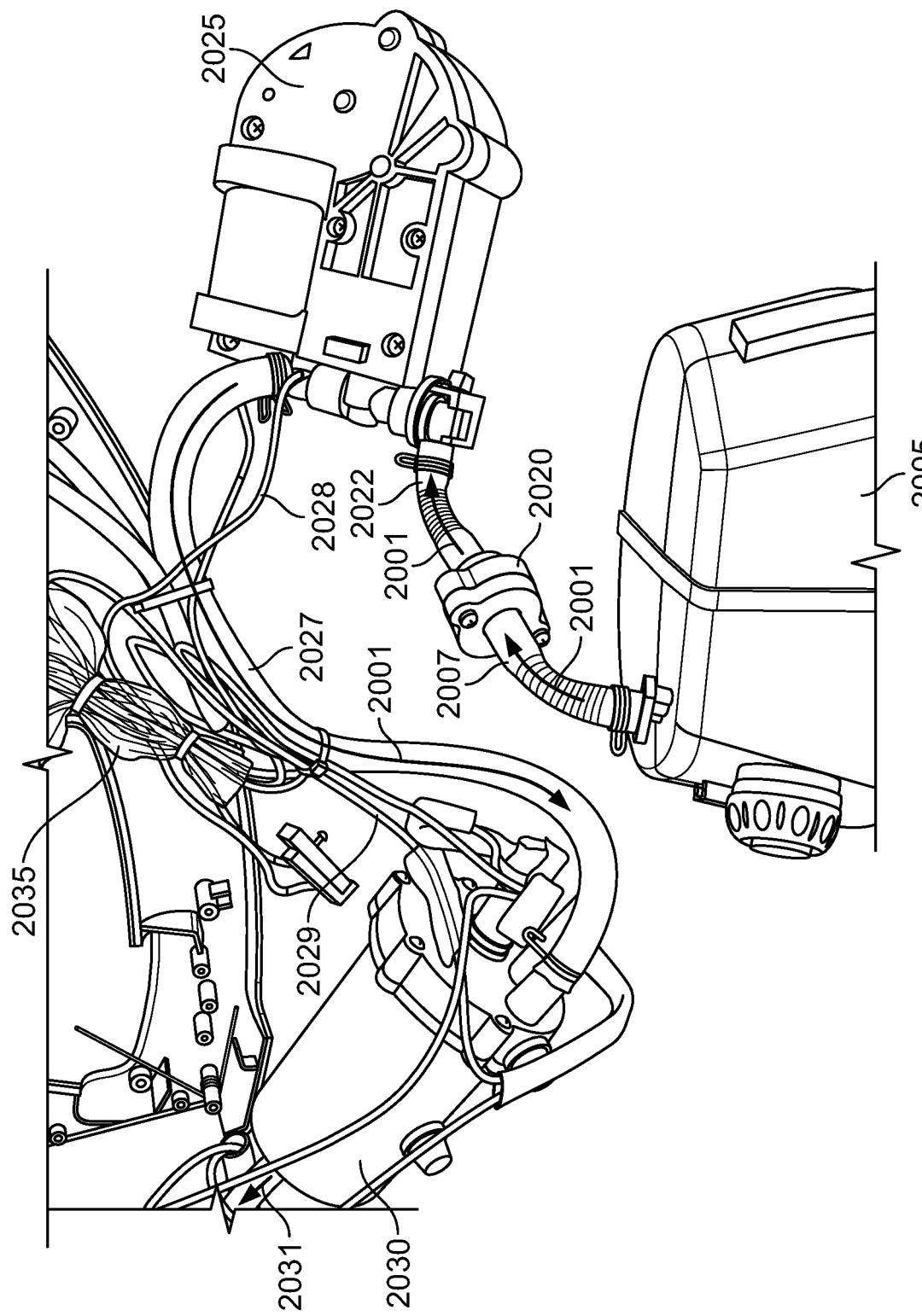
FIG. 20 illustrates a second view of the fluid container, filter member, pump, heater or heat exchange unit, and microcontroller of the vapor ablation system of FIG. 17.

FIGS. 19 and 20 illustrate first and second views respectively, of the fluid container 1905, 2005, first filter member 1920, 2020, pump 1925, 2025, heater or heat exchange unit 1930, 2030, and microcontroller 1935, 2035 of the vapor ablation system of FIG. 17. The container 1905, 2005 is connected to the first filter member 1920, 2020 by a first length of sterile tubing 1907, 2007 and the first filter member 1920, 2020 is connected to the pump 1925, 2025 by a second length of sterile tubing 1922, 2022. A third length of sterile tubing 1927, 2027 connects the pump 1925, 2025 to the heater or heat exchange unit 1930, 2030. The microcontroller 1935, 2035, is operably connected to the pump 1925, 2025 by a first set of control wires 1928, 2028 and to the heater or heat exchange unit 1930, 2030 by a second set of control wires 1929, 2029. The arrows 1901, 2001 depict the direction of the flow of water from the container 1905, 2005, through the first filter member 1920, 2020 and pump 1925, 2025 and into the heater or heat exchange member 1930, 2030 where it is converted to vapor. Arrow 1931, 2031 depicts the direction of flow of vapor from the heater or heat exchange unit 1930, 2030 into the ablation catheter (not shown) for use in the ablation procedure.

Figure 21:
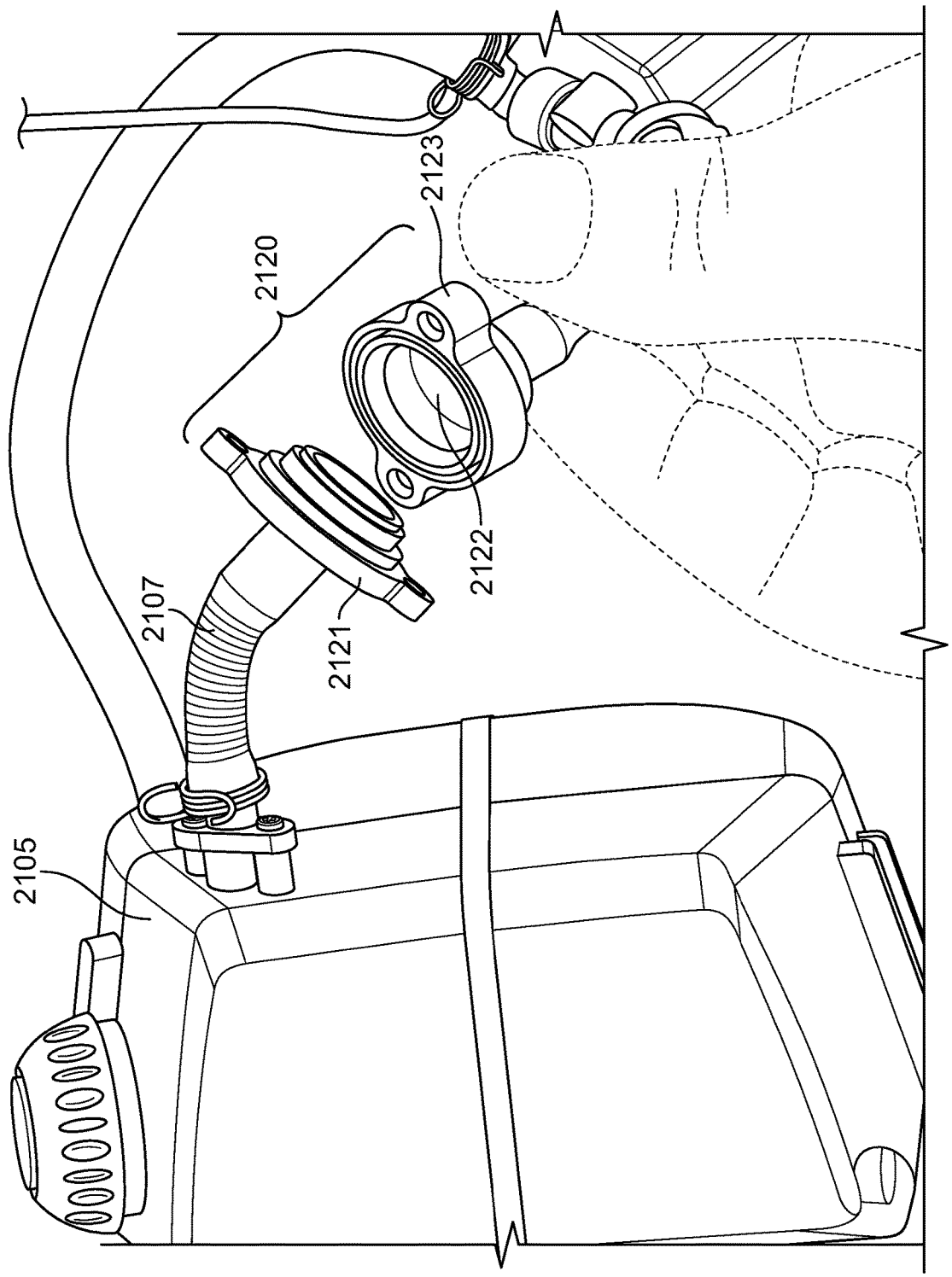
FIG. 21 illustrates the unassembled filter member of the vapor ablation system of FIG. 17, depicting the filter positioned within.

FIG. 21 illustrates the unassembled first filter member 2120 of the vapor ablation system of FIG. 17, depicting the filter 2122 positioned within. In one embodiment, the first filter member 2120 includes a proximal portion 2121, a distal portion 2123, and a filter 2122. The proximal portion 2121 and distal portion 2123 secure together and hold the filter 2122 within. Also depicted in FIG. 21 are the disposable, single use sterile fluid container 2105 and the first length of sterile tubing 2107 connecting the container 2105 to the proximal portion 2121 of the first filter member 2120.

Figure 22:
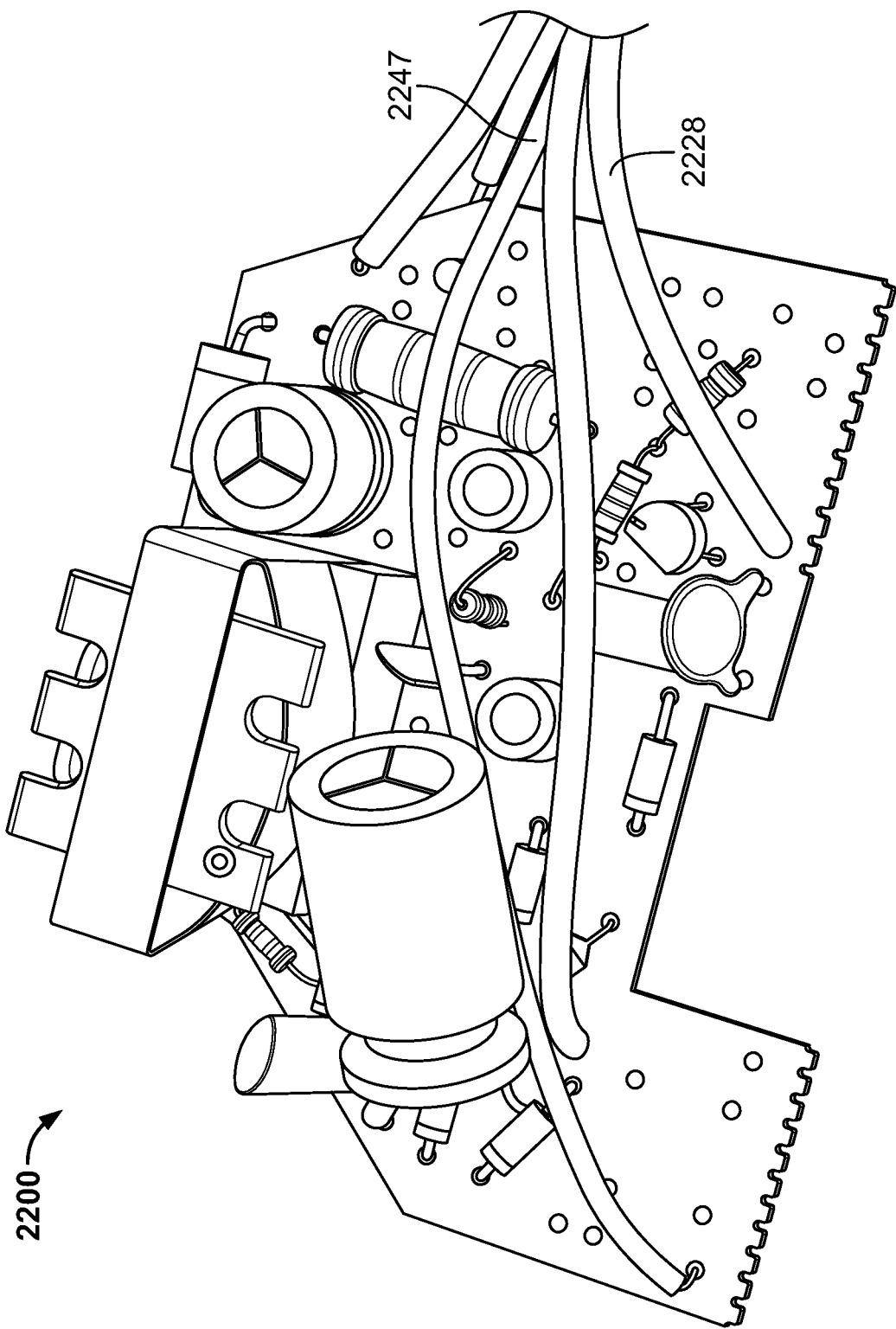
FIG. 22 illustrates one embodiment of the microcontroller of the vapor ablation system of FIG. 17.

FIG. 22 illustrates one embodiment of the microcontroller 2200 of the vapor ablation system of FIG. 17. In various embodiments, the microcontroller 2200 includes a plurality of control wires 2228 connected to the pump and heater or heat exchange unit for controlling said components and a plurality of transmission wires 2247 for receiving flow, pressure, and temperature information from optional sensors positioned proximate the distal end of the ablation catheter.

Figure 23:
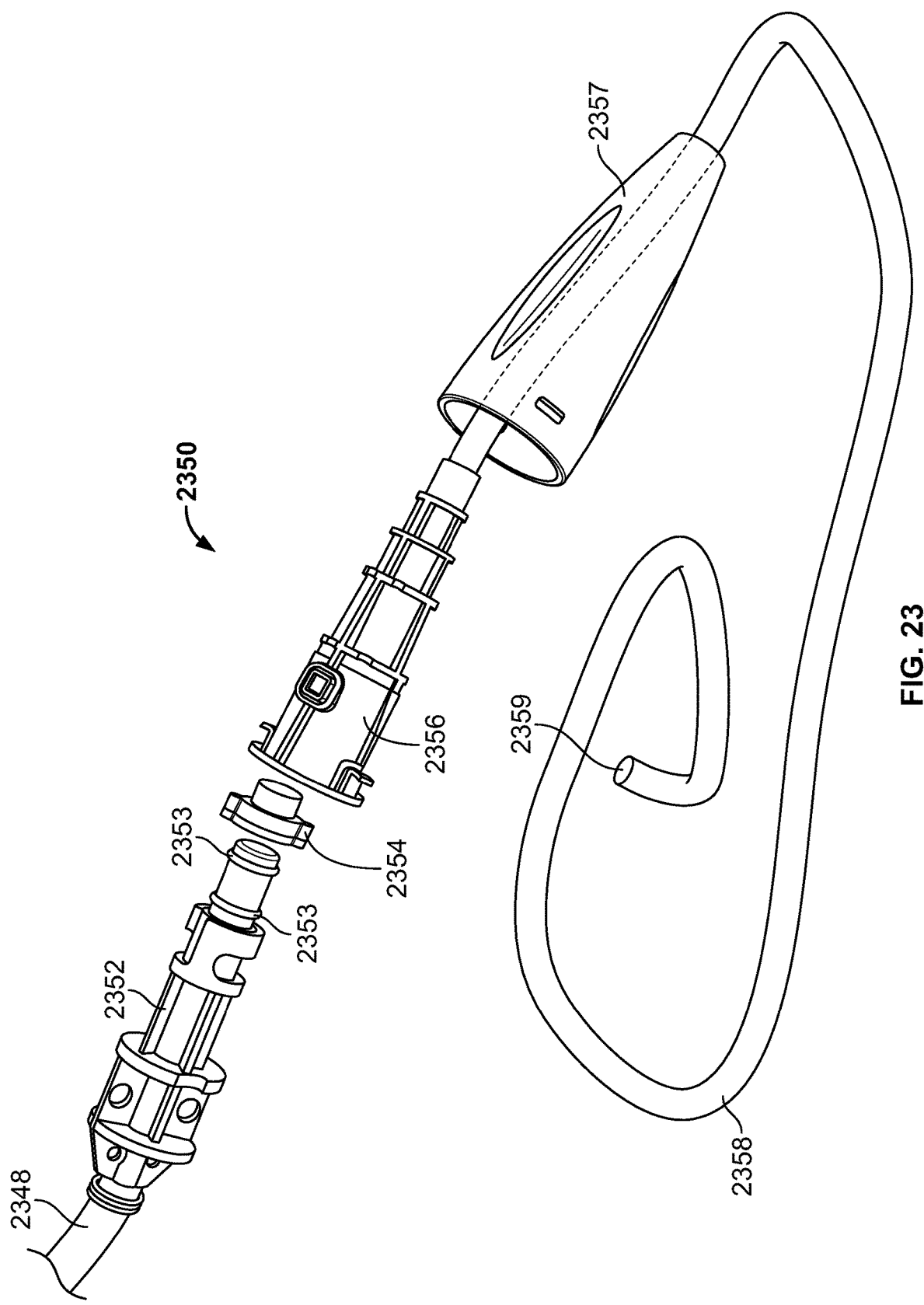
FIG. 23 illustrates one embodiment of a catheter assembly for use with the vapor ablation system of FIG. 17.

FIG. 23 illustrates one embodiment of a catheter assembly 2350 for use with the vapor ablation system of FIG. 17. Vapor is delivered from the heater or heat exchange unit to the catheter assembly 2350 via a tube 2348 attached to the proximal end of a connector component 2352 of the assembly 2350. A disposable catheter 2356 with a fixedly attached disposable length of flexible tubing 2358 at its distal end is fitted over the connector component 2352. A second filter member 2354 is positioned between the connector component 2352 and the disposable catheter 2356 for purifying the vapor supplied by the heater or heat exchange unit. The connector component 2352 includes two washers 2353 positioned apart a short distance at its distal end to engage the overlaying disposable catheter 2356 and form a double-stage seal, thereby preventing vapor leakage between the components. Once the disposable catheter 2356 has been fitted to the distal end of the connector component 2352, a catheter connector 2357 is slid over the disposable flexible tubing 2358 and disposable catheter 2356 and is then snapped into place onto the connector component 2352. The catheter connector 2357 acts to keep the disposable catheter 2356 in place and also assists in preventing vapor leakage. In various embodiments, the disposable flexible tubing 2358 includes one or more holes or ports 2359 at or proximate its distal end for the delivery of ablative vapor to target tissues.

Figure 24:
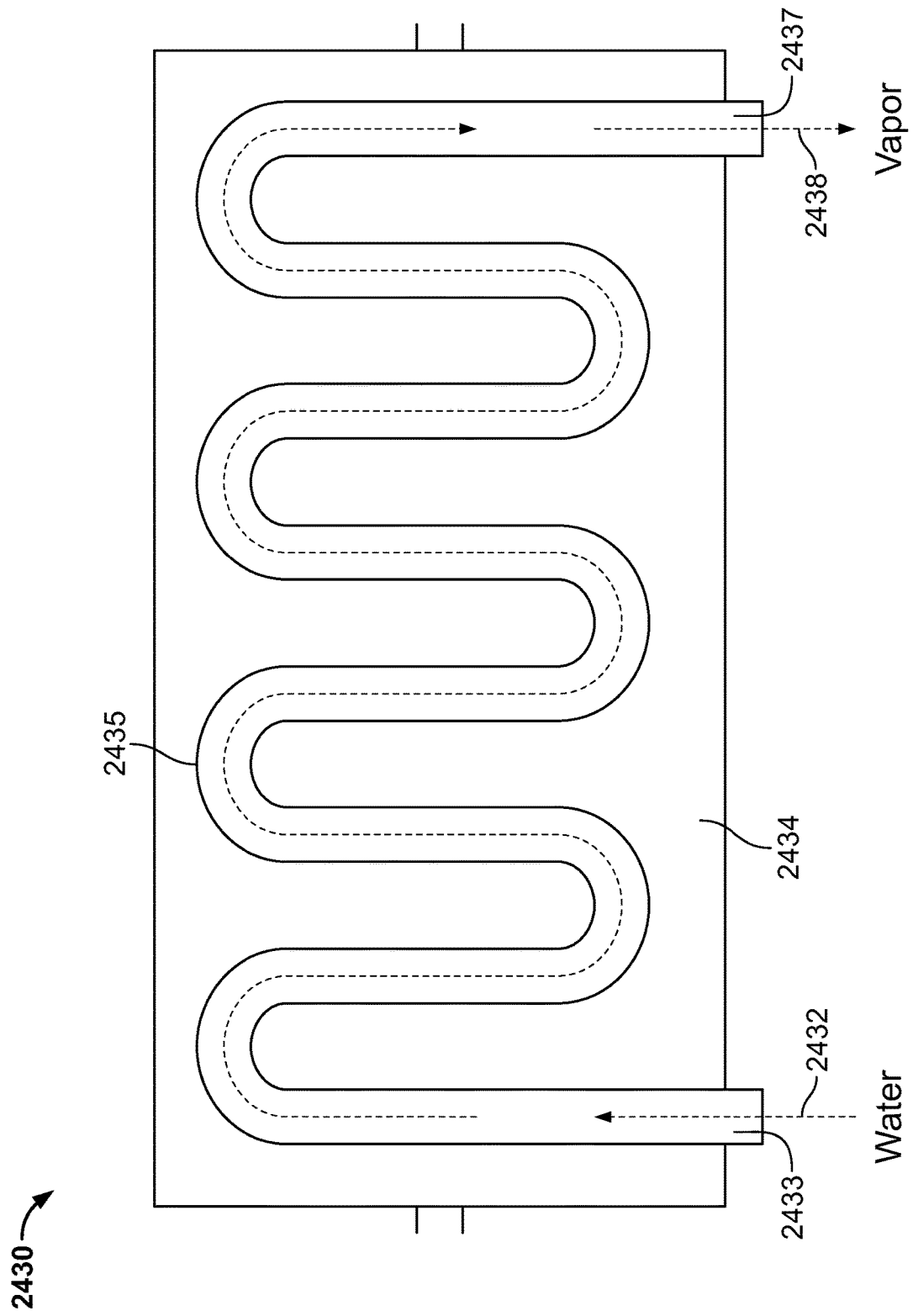
FIG. 24 illustrates one embodiment of a heat exchange unit for use with the vapor ablation system of FIG. 17.

FIG. 24 illustrates one embodiment of a heat exchange unit 2430 for use with the vapor ablation system of FIG. 17. The heat exchange unit 2430 comprises a length of coiled tubing 2435 surrounded by a heating element 2434. Water 2432 enters the coiled tubing 2435 of the heat exchange unit 2430 at an entrance port 2433 proximate a first end of said heat exchange unit 2430. As the water 2432 flows within the coiled tubing 2435, it is converted into vapor (steam) 2438 by the heat emanating from said coiled tubing 2435 which has been heated by the heating element 2434. The vapor 2438 exits the coiled tubing 2435 of the heat exchange unit 2430 at an exit port 2437 proximate a second end of said heat exchange unit 2430 and is then delivered to the ablation catheter (not shown) for use in the ablation procedure.

Figure 25:
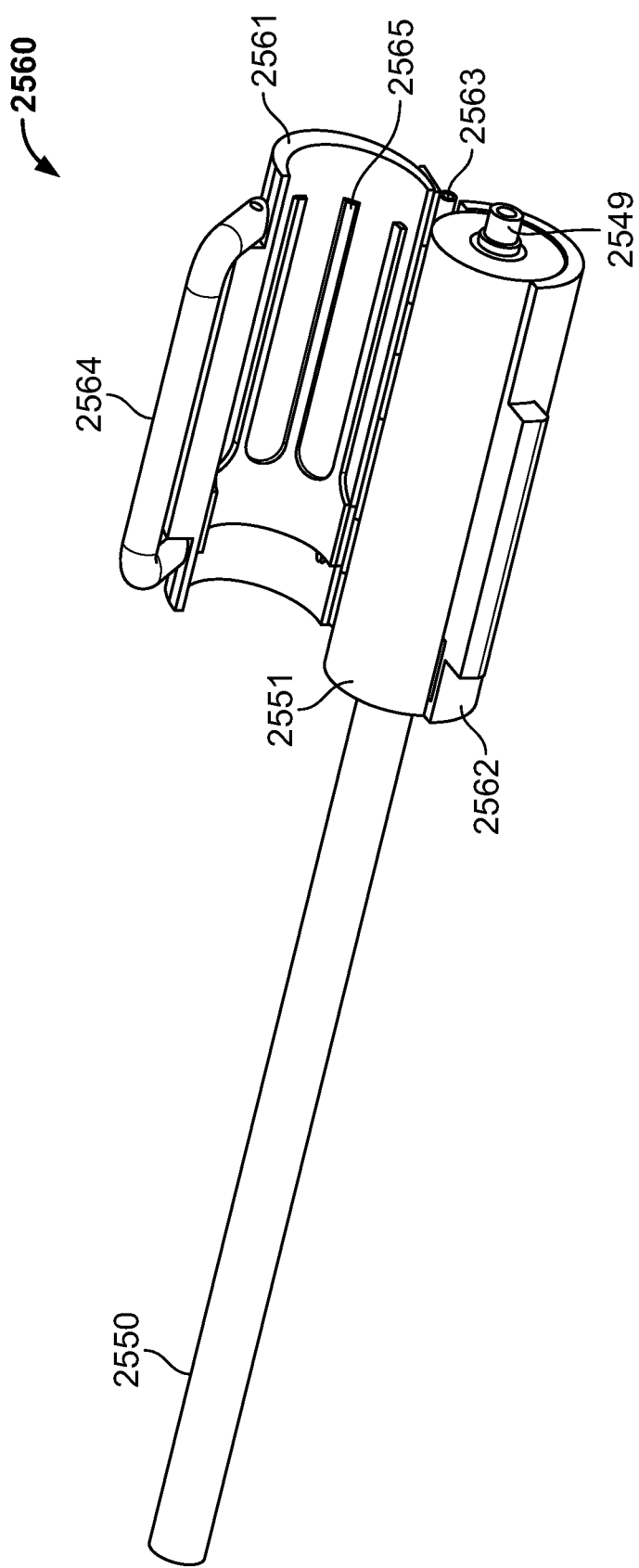
FIG. 25 illustrates another embodiment of a heat exchange unit for use with the vapor ablation system of the present invention.

FIG. 25 illustrates another embodiment of a heat exchange unit 2560 for use with the vapor ablation system of the present invention. In the pictured embodiment, the heat exchange unit 2560 comprises a cylindrically shaped, pen sized 'clamshell' style heating block. The heating block of the heat exchange unit 2560 includes a first half 2561 and a second half 2562 fixedly attached by a hinge 2563 along one side, wherein the halves 2561, 2562 fold together and connect on the opposite side. In one embodiment, the sides of the halves opposite sides with the hinge include a clasp for holding the two halves together. In one embodiment, one of the halves includes a handle 2564 for manipulating the heat exchange unit 2560. When the halves are folded together, the heat exchange unit 2560 snugly envelopes a cylindrically shaped catheter fluid heating chamber 2551 attached to, in-line and in fluid communication with, the proximal end of the ablation catheter 2550. Each half 2561, 2562 of the heat exchange unit 2560 includes a plurality of heating elements 2565 for heating the block. The positioning and fit of the heating block place it in close thermal contact with the catheter fluid heating chamber 2551. When in operation, the heating elements 2565 heat the heating block which transfers heat to the catheter fluid heating chamber 2551, which in turn heats the water inside the chamber 2551, converting said water to vapor. The heating block does not directly contact the water. In one embodiment, the catheter fluid heating chamber 2551 comprises a plurality of linear indentations 2591 stretching along the length of the component and in parallel with the heating elements 2565. Upon closing the halves 2561, 2562, the heating elements 2565, which optionally protrude from the internal surfaces of the halves 2561, 2562 contact, and fit within, the linear indentations 2591. This also increases the surface area of contact between the heating block and the heating chamber, improving the efficiency of heat exchange.

A luer fitting coupler 2549 is provided at the proximal end of the catheter fluid heating chamber 2551 for connecting a tube supplying sterile water. In one embodiment, a one-way valve is included at the proximal end of the catheter fluid heating chamber 2551, distal to the luer fitting 2549, to prevent the passage of vapor under pressure toward the water supply.

As described above, the catheter fluid heating chamber is designed as part of the ablation catheter and, along with the remainder of the catheter, is single use and disposable. In another embodiment, the chamber is reusable, in which case the luer fitting is positioned in between the catheter shaft and the chamber. The heating block is designed to be axially aligned with the heating chamber when in use, is reusable, and will not be damaged in the event that it falls to the floor. In one embodiment, the weight and dimensions of the heating block are designed such that it can be integrated into a pen-sized and shaped handle of the ablation catheter. The handle is thermally insulated to prevent injury to the operator.

In one embodiment, the heating block receives its power from a console which is itself line powered and designed to provide 700-1000 W of power, as determined by the fluid vaporization rate. The heating block and all output connections are electrically isolated from line voltage. In one embodiment, the console includes a user interface allowing adjustment of power with a commensurate fluid flow rate. In addition, in one embodiment, a pump, such as a syringe pump, is used to control the flow of fluid to the heating chamber and heating element. In one embodiment, the volume of the syringe is at least 10 ml and is ideally 60 ml.

In the above embodiment, the catheter to be used with the vapor ablation system is designed using materials intended to minimize cost. In one embodiment, the tubing used with the catheter is able to withstand a temperature of at least 125° C. and can flex through an endoscope's bend radius (approximately 1 inch) without collapse. In one embodiment, the section of the catheter that passes through an endoscope is 7 French (2.3 mm) diameter and has a minimum length of 215 cm. In one embodiment, thermal resistance is provided by the catheter shaft material which shields the endoscope from the super-heated vapor temperature. In one embodiment, the heat exchange unit is designed to interface directly with, or in very close proximity to, an endoscope's biopsy channel to minimize the likelihood of a physician handling heated components. Having the heat exchange unit in close proximity to the endoscope handle also minimizes the length of the catheter through which the vapor needs to travel, thus minimizing heat loss and premature condensation.

Figure 26:
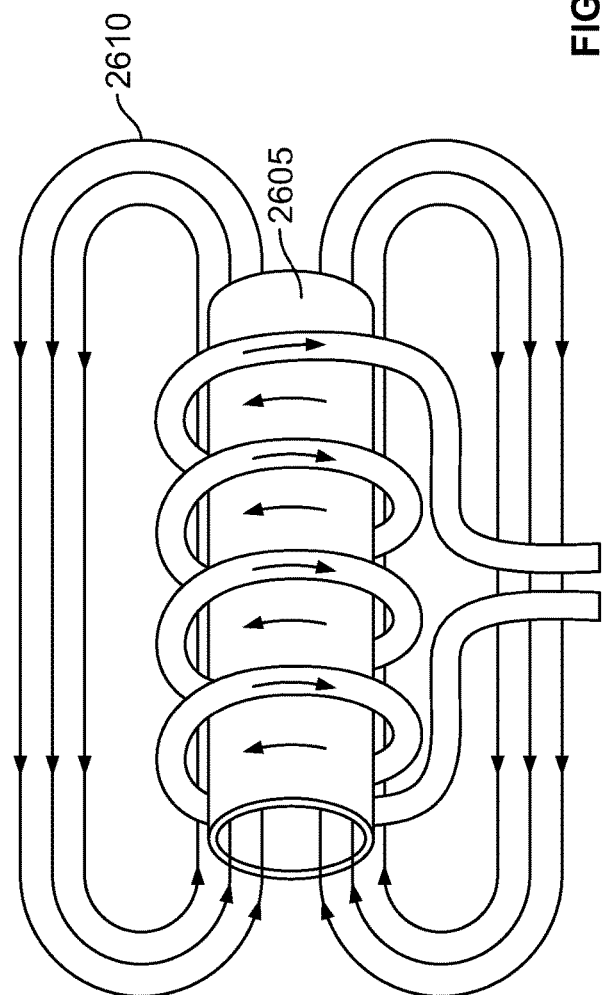
FIG. 26 illustrates the use of induction heating to heat a chamber.

In various embodiments, other means are used to heat the fluid within the catheter fluid heating chamber. FIG. 26 illustrates the use of induction heating to heat a chamber 2605. When an alternating electric current is passed through a coil of wire within the chamber 2605, the coil creates a magnetic field. The magnetic lines of flux 2610 cut through the air around the coil. When the chamber 2605 is composed of a ferrous material, such as, iron, stainless steel, or copper, electrical currents known as eddy currents are induced to flow in the chamber 2605, resulting in localized heating of the chamber 2605.

Figure 27A:
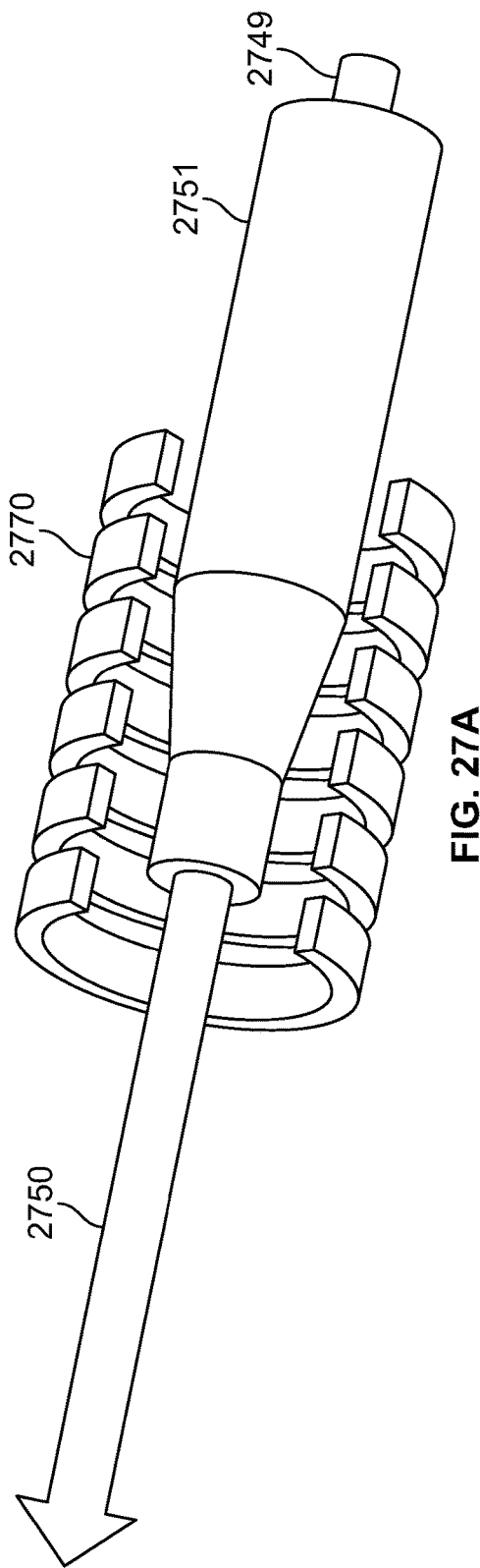
FIG. 27A illustrates one embodiment of a coil used with induction heating in the vapor ablation system of the present invention.

FIG. 27A illustrates one embodiment of a coil 2770 used with induction heating in the vapor ablation system of the present invention. The coil is positioned surrounding the catheter fluid heating chamber 2751. An alternating current passing through the coil creates a magnetic field and results in heating of the catheter fluid heating chamber 2751. The heated chamber heats the fluid within, converting it into a vapor, which passes into the catheter 2750 for use in the ablation procedure. The coil itself does not heat, making it safe to touch. A luer fitting coupler 2749 is provided at the proximal end of the catheter fluid heating chamber 2751 for connecting a tube supplying sterile water. In one embodiment, a one-way valve (not shown) is included at the proximal end of the catheter fluid heating chamber 2751, distal to the luer fitting 2749, to prevent the passage of vapor toward the water supply. In one embodiment, thermal insulating material (not shown) is positioned between the coil 2770 and the heating chamber 2751. In another embodiment, the chamber 2751 is suspended in the center of the coil 2770 with no physical contact between the two. In this embodiment, the intervening air acts as a thermally insulating material. The design of the chamber is optimized to increase its surface area to maximize contact and heat transfer, in turn resulting in more efficient vapor generation.

Figure 27B:
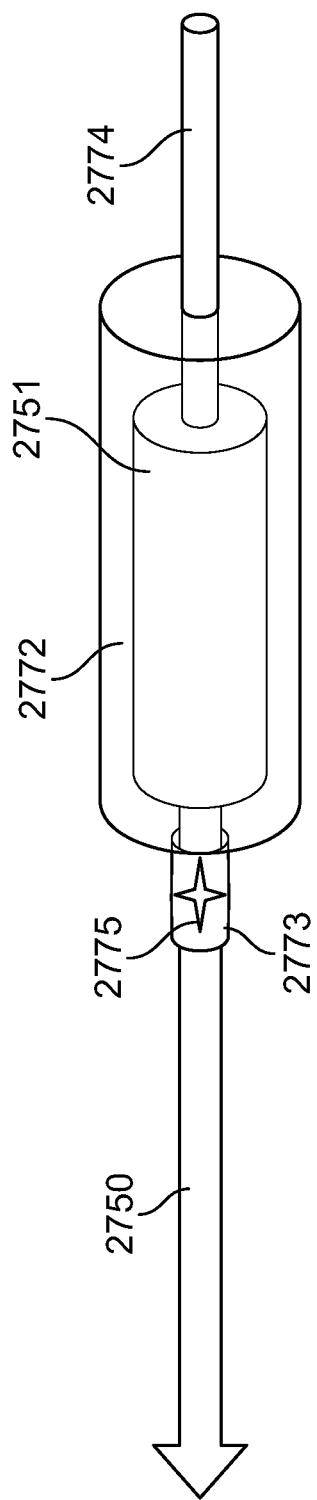
FIG. 27B illustrates one embodiment of a catheter handle used with induction heating in the vapor ablation system of the present invention.

FIG. 27B illustrates one embodiment of a catheter handle 2772 used with induction heating in the vapor ablation system of the present invention. The handle 2772 is thermally insulated and incorporates an induction coil. In one embodiment, the handle 2772 includes an insulated tip 2773 at its distal end that engages with an endoscope channel after the catheter is inserted into the endoscope. The catheter 2750 is connected to the heating chamber 2751 which in turn is connected with the pump via an insulated connector 2774. In one embodiment, the heating chamber 2751 length and diameter are less than those of the handle 2772 and the induction coil, thus the heating chamber 2751 can slide inside the handle 2772 in a coaxial fashion while maintaining a constant position within the magnetic field generated by the induction coil. The operator can manipulate the catheter 2750 by grasping on the insulated connector 2774 and moving it in and out of the handle 2772 which in turn moves the catheter tip in and out of the distal end of the endoscope. In this design, the heated portions of the catheter 2750 are within the channel of the endoscope and in the insulated handle 2772, thus not coming into contact with the operator at anytime during the operation. An optional sensor 2775 on the insulated tip 2773 can sense when the catheter is not engaged with the endoscope and temporarily disable the heating function of the catheter to prevent accidental activation and thermal injury to the operator. With respect to FIG. 27B, the catheter 2750 and heating chamber 2751 are the heated components of the system while the handle 2772, insulated tip 2773, and insulated connector 2774 are the cool components and therefore safe to touch by the user.

Figure 28A:
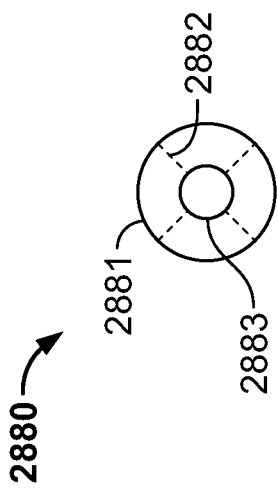
FIG. 28A is a front view cross sectional diagram illustrating one embodiment of a catheter used with induction heating in the vapor ablation system of the present invention.
Figure 28B:
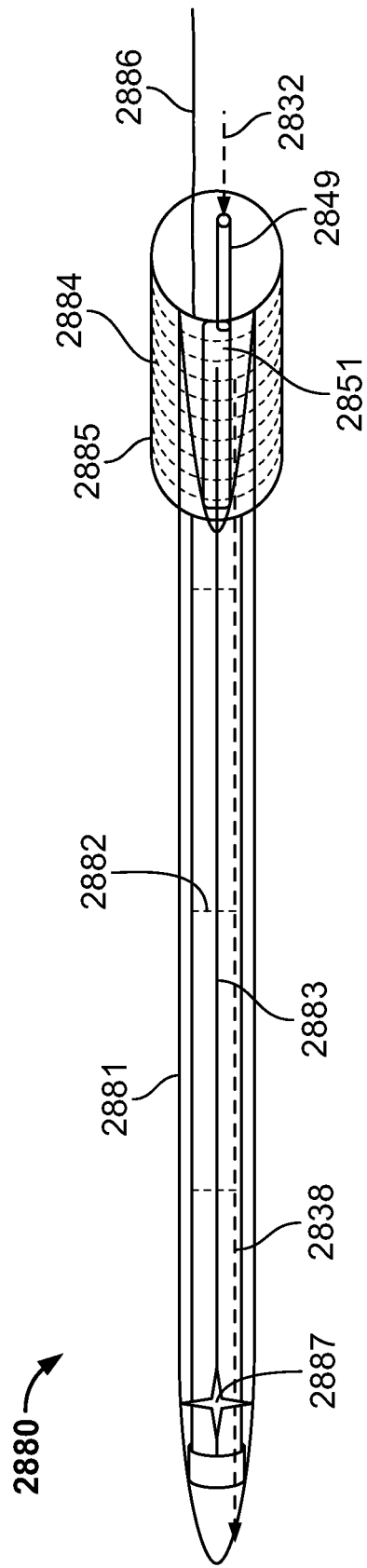
FIG. 28B is a longitudinal view cross sectional diagram illustrating one embodiment of a catheter used with induction heating in the vapor ablation system of the present invention.

FIGS. 28A and 28B are front and longitudinal view cross sectional diagrams respectively, illustrating one embodiment of a catheter 2880 used with induction heating in the vapor ablation system of the present invention. The catheter 2880 includes an insulated handle 2886 that contains a heating chamber 2851 and an induction coil 2884. The heating chamber 2851 includes a luer lock 2849 at its proximal end. The luer lock 2849 has a one-way valve that prevents the backward flow of vapor from the chamber 2851. Vaporization of fluid in the chamber results in volume expansion and an increase in pressure which pushes the vapor out of the chamber 2849 and into the catheter body. The induction coil 2884 includes a wire 2886 that extends from the proximal end of the catheter 2880 for the delivery of an alternating current. The handle 2886 is connected to the catheter 2880 with an outer insulating sheath 2881 made of a thermally insulating material.

In various embodiments, the insulating material is polyether ether ketone (PEEK), polytetrafluoroethylene (PTFE), fluorinated ethylene propylene (FEP), polyether block amide (PEBA), polyimide, or a similar material. In various embodiments, optional sensors 2887 positioned proximate the distal end of the catheter 2880 measure one or more of temperature, pressure, or flow of vapor and transmit the information to a microprocessor, which in turn controls the flow rate of the fluid and the level of vaporizing energy provided to the chamber 2851. The microcontroller adjusts fluid flow rate and chamber temperature based on the sensed information, thereby controlling the flow of vapor and in turn, the flow of ablative energy to the target tissue.

In one embodiment, the catheter 2880 includes an inner flexible metal skeleton 2883. In various embodiments, the skeleton 2883 is composed of copper, stainless steel, or another ferric material. The skeleton 2883 is in thermal contact with the heating chamber 2851 so that the heat from the chamber 2851 is passively conducted through the metal skeleton 2883 to heat the inside of the catheter 2880, thus maintaining the steam in a vaporized state and at a relatively constant temperature. In various embodiments, the skeleton 2883 extends through a particular portion or the entire length of the catheter 2880. In one embodiment, the skeleton 2883 includes fins 2882 at regular intervals that keep the skeleton 2883 in the center of the catheter 2880 for uniform heating of the catheter lumen.

Figure 28C:
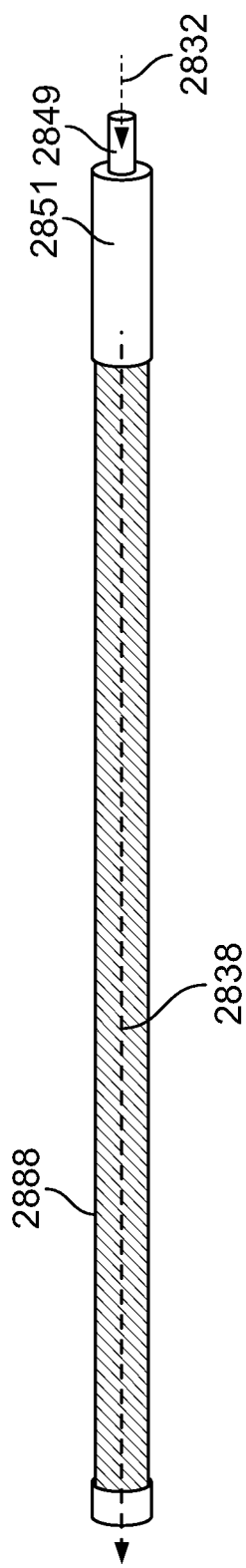
FIG. 28C is a longitudinal view cross sectional diagram illustrating another embodiment of a catheter with a metal spiral used with induction heating in the vapor ablation system of the present invention.
Figure 28D:
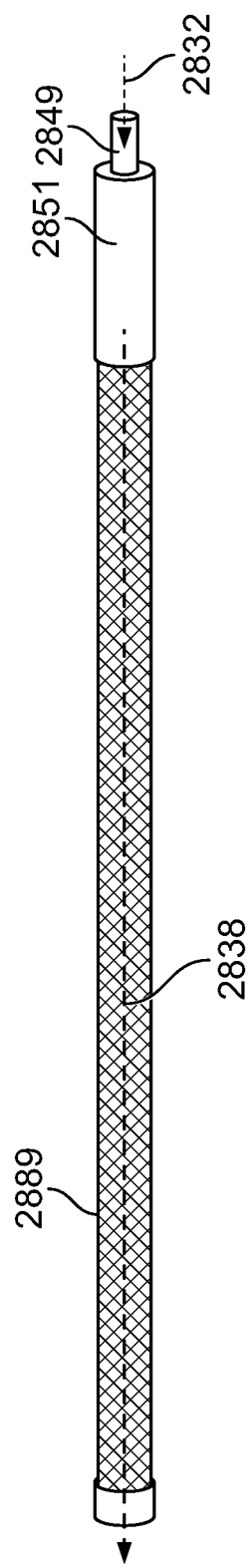
FIG. 28D is a longitudinal view cross sectional diagram illustrating another embodiment of a catheter with a mesh used with induction heating in the vapor ablation system of the present invention; and, FIG. 29 illustrates one embodiment of a heating unit using microwaves to convert fluid to vapor in the vapor ablation system of the present invention.

In another embodiment, as seen in FIG. 28C, the catheter includes an inner metal spiral 2888 in place of the skeleton. In yet another embodiment, as seen in FIG. 28D, the catheter includes an inner metal mesh 2889 in place of the skeleton. Referring to FIGS. 28B, 28C, and 28D simultaneously, water 2832 enters the luer lock 2849 at a predetermined rate. It is converted to vapor 2838 in the heating chamber 2851. The metal skeleton 2883, spiral 2888, and mesh 2889 all conduct heat from the heating chamber 2851 into the catheter lumen to prevent condensation of the vapor in the catheter and insure that ablating vapor will exit the catheter from one or more holes or ports at its distal end.

Figure 29:
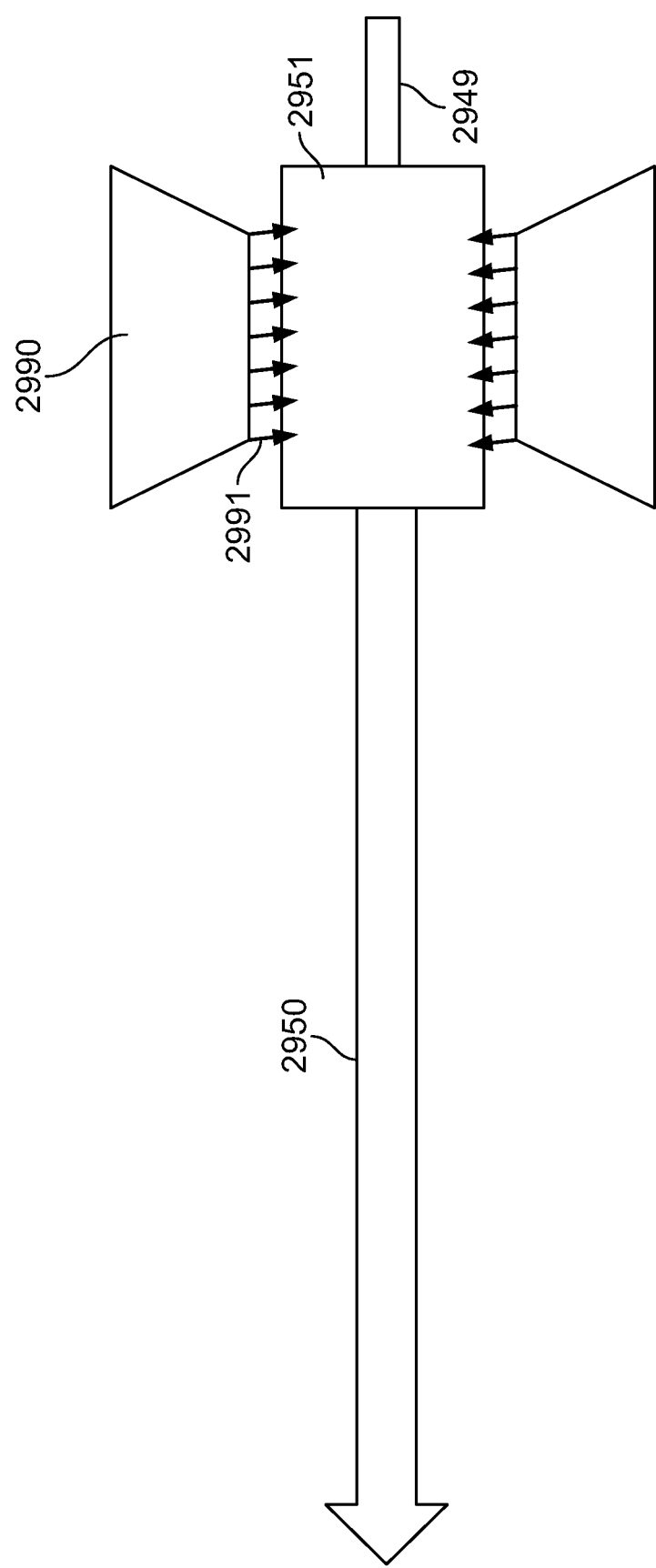

FIG. 29 illustrates one embodiment of a heating unit 2990 using microwaves 2991 to convert fluid to vapor in the vapor ablation system of the present invention. The microwaves 2991 are directed toward the catheter fluid heating chamber 2951, heating the chamber 2951 and converting the fluid within into vapor. The vapor passes into the catheter 2950 for use in the ablation procedure. A luer fitting coupler 2949 is provided at the proximal end of the catheter fluid heating chamber 2951 for connecting a tube supplying sterile water. In one embodiment, a one-way valve (not shown) is included at the proximal end of the catheter fluid heating chamber 2951, distal to the luer fitting 2949, to prevent the passage of vapor toward the water supply.

In various embodiments, other energy sources, such as, High Intensity Focused Ultrasound (HIFU) and infrared energy, are used to heat the fluid in the catheter fluid heating chamber.

One advantage of a vapor delivery system utilizing a heating coil is that the vapor is generated closer to the point of use. Traditional vapor delivery systems often generate vapor close to or at the point in the system where the liquid is stored. The vapor must then travel through a longer length of tubing, sometimes over 2 meters, before reaching the point of use. As a result of the distance traveled, the system can sometimes deliver hot liquid as the vapor cools in the tubing from the ambient temperature.

The device and method of the present invention can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferrimagnetic materials can be incorporated into the catheter to help with magnetic navigation.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A vapor ablation system configured to ablate tissue in a gastrointestinal (GI) tract of a patient, comprising:
   a pump in pressure communication with a source of fluid;
   a heating component in fluid communication with the source of fluid, wherein the heating component is configured to apply heat to the fluid to convert the fluid to a vapor ablative agent;
   a controller in operable communication with the pump and the heating component;
   a catheter in fluid communication with the heating component, wherein the catheter comprises:
      a hollow shaft through which the vapor ablative agent can travel;
      a first positioning element attached to the shaft at a proximal end of the shaft, wherein the first positioning element is configured to position the catheter at a first fixed distance from the tissue to be ablated, wherein the first positioning element is defined by a first disc shaped wire mesh structure and wherein the first disc shaped wire mesh structure is at least partially covered by a membrane;
      a second positioning element attached to the shaft at a distal end of the shaft and separated from the first positioning element by a length, wherein the second positioning element is configured to position the catheter at a second fixed distance from the tissue to be ablated and wherein the second positioning element is defined by a second disc shaped wire mesh structure and wherein the second disc shaped wire mesh structure is at least partially covered by a membrane; and
      more than one port distributed along circumferentially positioned around the shaft and configured to deliver the vapor ablative agent toward at least a portion of the GI tract, wherein the controller is programmed to limit an amount of the vapor ablative agent delivered through the more than one port such that a pressure within the patient's GI tract does not exceed 5 atm and programmed to generate the vapor ablative agent such that it is delivered from more than one port for a treatment period that is less than 1 minute.

2. The vapor ablation system of claim 1, wherein the controller is programmed to determine an amount of the fluid needed to ablate the tissue.

3. The vapor ablation system of claim 1, wherein the controller is programmed to limit a maximum dose of the vapor ablative agent based on a type of disorder being treated.

4. The vapor ablation system of claim 3, wherein the disorder is at least one of Barrett's esophagus, dysplasia, vascular GI disorders, lesions, inflammatory lesions, tumors, vascular lesions, or polyps.

5. The vapor ablation system of claim 1, further comprising a first filter disposed between, and in fluid communication with, the container and the catheter.

6. The vapor ablation system of claim 1, wherein the controller is programmed to determine an amount of the fluid needed to ablate the tissue as a function of an amount of thermal energy required to ablate the tissue.

7. The vapor ablation system of claim 1, wherein the controller is programmed to adjust a flow rate of the fluid supplied to the catheter.

8. The vapor ablation system of claim 1, wherein the pump is a syringe pump.

9. The vapor ablation system of claim 1, wherein the syringe pump has a volume of at least 10 ml.

10. The vapor ablation system of claim 1, wherein the first positioning element has a diameter that is greater than a diameter of the second positioning element.

11. The vapor ablation system of claim 1, wherein the first positioning element has a diameter that is equal to a diameter of the second positioning element.

12. The vapor ablation system of claim 1, wherein the catheter is disposable and configured for a single use.

13. The vapor ablation system of claim 1, wherein the heating element uses one of magnetic induction, microwave, high intensity focused ultrasound, resistance, radiofrequency or infrared energy to convert the fluid into the vapor ablative agent.

14. A vapor ablation system configured to ablate tissue in a gastrointestinal (GI) tract of a patient, comprising:
  a container with fluid;
  a pump configured to pump the fluid from the container;
  a heating component in fluid communication with the container, wherein the heating component is configured to apply heat to the fluid to convert the fluid to a vapor ablative agent;
  a catheter in fluid communication with the heating component, wherein the catheter comprises:
    a hollow shaft through which the vapor ablative agent can travel;
    a first positioning element attached to the shaft at a proximal end of the shaft, wherein the first positioning element is configured to position the catheter at a first fixed distance from the tissue to be ablated, wherein the first positioning element is defined by a first disc shaped wire mesh structure and wherein the first disc shaped wire mesh structure is at least partially covered by a membrane;
    a second positioning element attached to the shaft at a distal end of the shaft and separated from the first positioning element by a length, wherein the second positioning element is configured to position the catheter at a second fixed distance from the tissue to be ablated and wherein the second positioning element is defined by a second disc shaped wire mesh structure and wherein the second disc shaped wire mesh structure is at least partially covered by a membrane; and
    more than one port distributed along circumferentially positioned around the shaft and configured to release the vapor ablative agent toward at least a portion of the GI tract; and
  a controller programmed to limit an amount of the vapor ablative agent delivered through the more than one port such that a pressure within the patient's GI tract does not exceed 5 atm and programmed to determine an amount of the fluid needed to ablate the tissue based on a type of disorder being treated.

15. The vapor ablation system of claim 14, wherein the disorder is at least one of Barrett's esophagus, dysplasia, vascular GI disorders, lesions, inflammatory lesions, tumors, vascular lesions, or polyps.

16. The vapor ablation system of claim 14, further comprising a first filter disposed between, and in fluid communication with, the container and the catheter.

17. The vapor ablation system of claim 14, wherein the controller is programmed to determine the amount of the fluid needed to ablate the tissue as a function of an amount of thermal energy required to ablate the tissue.

18. The vapor ablation system of claim 14, wherein the controller is programmed to adjust a flow rate of the fluid supplied to the catheter.

19. The vapor ablation system of claim 14, wherein the pump is a syringe pump.

20. The vapor ablation system of claim 19, wherein the syringe pump has a volume of at least 10 ml.

21. The vapor ablation system of claim 14, wherein the first positioning element has a diameter that is greater than a diameter of the second positioning element.

22. The vapor ablation system of claim 14, wherein the first positioning element has a diameter that is equal to a diameter of the second positioning element.

23. The vapor ablation system of claim 14, wherein the catheter is disposable and configured for a single use.

24. The vapor ablation system of claim 14, wherein the heating element uses one of magnetic induction, microwave, high intensity focused ultrasound, radiofrequency, resistance, or infrared energy to convert the fluid into the vapor ablative agent.

* * * * *